United States Patent
Chun et al.

(10) Patent No.: US 9,724,360 B2
(45) Date of Patent: Aug. 8, 2017

(54) METHODS FOR TREATING FILOVIRIDAE VIRUS INFECTIONS

(71) Applicant: Gilead Sciences, Inc., Foster City, CA (US)

(72) Inventors: Byoung Kwon Chun, Pleasanton, CA (US); Michael O' Neil Hanrahan Clarke, Redwood City, CA (US); Edward Doerffler, Foster City, CA (US); Hon Chung Hui, Foster City, CA (US); Robert Jordan, Foster City, CA (US); Richard L. Mackman, Millbrae, CA (US); Jay P. Parrish, El Dorado Hills, CA (US); Adrian S. Ray, Burlingame, CA (US); Dustin Siegel, San Carlos, CA (US)

(73) Assignee: GILEAD SCIENCES, INC., Foster City, CA (US)

(*) Notice: Subject to any disclaimer, the term of this patent is extended or adjusted under 35 U.S.C. 154(b) by 0 days.

(21) Appl. No.: 14/926,062

(22) Filed: Oct. 29, 2015

(65) Prior Publication Data
US 2016/0122374 A1    May 5, 2016

Related U.S. Application Data

(60) Provisional application No. 62/105,619, filed on Jan. 20, 2015, provisional application No. 62/072,331, filed on Oct. 29, 2014.

(51) Int. Cl.
| | |
|---|---|
| C07H 15/18 | (2006.01) |
| C07H 7/06 | (2006.01) |
| A61K 31/685 | (2006.01) |
| C07D 487/04 | (2006.01) |
| C07D 519/00 | (2006.01) |
| C07F 9/24 | (2006.01) |
| C07F 9/6561 | (2006.01) |
| A61K 31/675 | (2006.01) |
| A61K 45/06 | (2006.01) |
| A61K 31/00 | (2006.01) |
| A61K 31/53 | (2006.01) |
| C07H 1/00 | (2006.01) |
| C07H 1/02 | (2006.01) |
| C07H 11/00 | (2006.01) |

(52) U.S. Cl.
CPC ........... *A61K 31/685* (2013.01); *A61K 31/00* (2013.01); *A61K 31/53* (2013.01); *A61K 31/675* (2013.01); *A61K 45/06* (2013.01); *C07D 487/04* (2013.01); *C07D 519/00* (2013.01); *C07F 9/2429* (2013.01); *C07F 9/65616* (2013.01); *C07H 1/00* (2013.01); *C07H 1/02* (2013.01); *C07H 11/00* (2013.01); *C07H 15/18* (2013.01)

(58) Field of Classification Search
None
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,105,493 B2 | 9/2006 | Sommadossi et al. | |
| 7,125,855 B2 | 10/2006 | Bhat et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |

(Continued)

FOREIGN PATENT DOCUMENTS

| | | |
|---|---|---|
| CA | 2367921 C | 7/2009 |
| CN | 1291994 A | 4/2001 |

(Continued)

OTHER PUBLICATIONS

Alessandrini, et al., "Synthesis of Differently Protected 1-C-methyl-ribofuranoses Intermediates for the Preparation of Biologically Active 1'-C-methyl-ribonucleosides," Journal of Carbohydrate Chemistry, 27(5):; 332-344, 2008.

Ali, et al., "Quantitative structure-activity relationships (QSAR) of two series of O-aryl or N-acyl O-ethyl phosphoramidate and phosphorodiamidate fungicides incorporating amino acid ethyl esters," Bulletin of Environmental Contamination and Toxicology, 65(4):415-420, 2000.

(Continued)

*Primary Examiner* — Traviss C McIntosh, III

(57) ABSTRACT

Provided are compounds, methods, and pharmaceutical compositions for treating Filoviridae virus infections by administering ribosides, riboside phosphates and prodrugs thereof, of Formula IV:

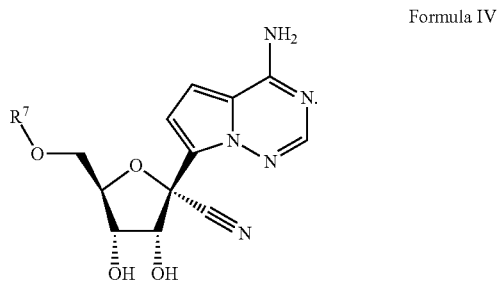

Formula IV

The compounds, compositions, and methods provided are particularly useful for the treatment of Marburg virus, Ebola virus and Cueva virus infections.

**8 Claims, No Dr

(56) References Cited

U.S. PATENT DOCUMENTS

| | | |
|---|---|---|
| 7,429,571 B2 | 9/2008 | Chand et al. |
| 7,514,410 B2 | 4/2009 | Babu et al. |
| 7,560,434 B2 | 7/2009 | Babu et al. |
| 7,598,230 B2 | 10/2009 | Cook et al. |
| 7,608,597 B2 | 10/2009 | Sommadossi et al. |
| 7,713,941 B2 | 5/2010 | Cook et al. |
| 7,807,653 B2 | 10/2010 | Cook et al. |
| 7,842,672 B2 | 11/2010 | Boojamra et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,568 B2 | 12/2011 | Narjes et al. |
| 8,119,607 B2 | 2/2012 | Francom et al. |
| 8,242,085 B2 | 8/2012 | Babu et al. |
| 8,318,682 B2 | 11/2012 | Butler et al. |
| 8,415,308 B2 | 4/2013 | Cho et al. |
| 8,455,451 B2 | 6/2013 | Cho et al. |
| 2003/0050229 A1 | 3/2003 | Sommadossi et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0203015 A1 | 8/2010 | Butler et al. |
| 2010/0234584 A1 | 9/2010 | Chang |
| 2010/0291031 A2 | 11/2010 | Francom et al. |
| 2010/0298257 A1 | 11/2010 | Ross et al. |
| 2011/0070194 A1 | 3/2011 | Cho et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0344028 A2 | 12/2013 | Butler et al. |
| 2015/0111839 A1 | 4/2015 | Mackman et al. |
| 2015/0152116 A1 | 6/2015 | Mackman et al. |

FOREIGN PATENT DOCUMENTS

| | | |
|---|---|---|
| CN | 1443189 A | 9/2003 |
| CN | 1498221 A | 5/2004 |
| CN | 1852915 A | 10/2006 |
| CN | 101043893 A | 9/2007 |
| CN | 101611046 A | 12/2009 |
| CN | 102906102 A | 1/2013 |
| EA | 201071170 A1 | 8/2011 |
| EA | 201171417 A1 | 5/2012 |
| EA | 201200525 A1 | 9/2012 |
| EP | 2 396 340 B1 | 12/2013 |
| JP | 41017629 | 10/1966 |
| JP | 2004520367 A | 7/2004 |
| JP | 2008502685 A | 1/2008 |
| JP | 2008518934 A | 6/2008 |
| TW | 1401084 B | 7/2013 |
| WO | WO-91/19721 A1 | 12/1991 |
| WO | WO-00/56734 A1 | 9/2000 |
| WO | WO-01/32153 A2 | 5/2001 |
| WO | WO-01/60315 A2 | 8/2001 |
| WO | WO-01/90121 A2 | 11/2001 |
| WO | WO-02/08241 | 1/2002 |
| WO | WO-02/18404 A2 | 3/2002 |
| WO | WO-02/32920 A2 | 4/2002 |
| WO | WO-02/057287 A2 | 7/2002 |
| WO | WO-02/057425 A2 | 7/2002 |
| WO | WO-03/093272 A1 | 11/2003 |
| WO | WO-03/093273 A1 | 11/2003 |
| WO | WO-03/100009 A2 | 12/2003 |
| WO | WO-2004/046331 A2 | 6/2004 |
| WO | WO-2005/009418 A2 | 2/2005 |
| WO | WO-2005/123087 A2 | 12/2005 |
| WO | WO-2006/031725 A2 | 3/2006 |
| WO | WO-2006/050161 A2 | 5/2006 |
| WO | WO-2006/065335 A2 | 6/2006 |
| WO | WO-2006/121820 A1 | 11/2006 |
| WO | WO-2007/027248 A2 | 3/2007 |
| WO | WO-2007/056170 A2 | 5/2007 |
| WO | WO-2007/064883 A2 | 6/2007 |
| WO | WO-2007/064931 A2 | 6/2007 |
| WO | WO-2007/065289 A2 | 6/2007 |
| WO | WO-2007/097991 A2 | 8/2007 |
| WO | WO-2007/135134 A1 | 11/2007 |
| WO | WO-2008/005542 A2 | 1/2008 |
| WO | WO-2008/079206 A1 | 7/2008 |
| WO | WO-2008/082601 A2 | 7/2008 |
| WO | WO-2008/085508 A2 | 7/2008 |
| WO | WO-2008/089105 A2 | 7/2008 |
| WO | WO-2008/116064 A2 | 9/2008 |
| WO | WO-2008/121634 A2 | 10/2008 |
| WO | WO-2008/141079 A1 | 11/2008 |
| WO | WO-2009/009951 A1 | 1/2009 |
| WO | WO-2009/131926 A1 | 10/2009 |
| WO | WO-2009/132123 A1 | 10/2009 |
| WO | WO2009/132135 * | 10/2009 |
| WO | WO-2009/132135 A1 | 10/2009 |
| WO | WO-2010/002877 A2 | 1/2010 |
| WO | WO-2010/036407 A2 | 4/2010 |
| WO | WO-2010/093608 A1 | 8/2010 |
| WO | WO-2010/099458 A1 | 9/2010 |
| WO | WO-2010/111381 A3 | 9/2010 |
| WO | WO-2010/135569 A1 | 11/2010 |
| WO | WO-2011/035231 A1 | 3/2011 |
| WO | WO-2011/035250 A1 | 3/2011 |
| WO | WO-2011/123645 A2 | 10/2011 |
| WO | WO-2011/123672 A1 | 10/2011 |
| WO | WO-2011/150288 A1 | 12/2011 |
| WO | WO-2012/012465 A1 | 1/2012 |
| WO | WO-2012/012776 A1 | 1/2012 |
| WO | WO-2012/039787 A2 | 3/2012 |
| WO | WO-2012/039791 A1 | 3/2012 |
| WO | WO-2012/051570 A1 | 4/2012 |
| WO | WO-2013/084165 A1 | 6/2013 |
| WO | WO-2014/042433 A2 | 3/2014 |
| WO | WO-2015/069939 A1 | 5/2015 |

OTHER PUBLICATIONS

Arimilli, M.N., et al., "Synthesis, In Vitro Biological Evaluation and Oral Bioavailability of 9-[2-(phosphonomethoxy)propyl]adenine (PMPA) Prodrugs," Antiviral Chemistry & Chemotherapy, vol. 8, No. 6, ; pp. 557-564 (1997).

ARIPO Form 21 and Substantive Examination Report (in English) for AP Application No. AP/P/2010/005439, dated Mar. 18, 2014.

Asbun, et al., "Synthesis of 5-substituted Pyrimidines. II," Journal of Organic Chemistry, 31:140-142, 1968.

Ballini, et al., "Enantioselective Synthesis of the Lactone Moiety of the Mevinic Acids using D-Xylose as a Chiral Precursor," Journal of the Chemical Society, Perkin Transactions 1, pp. 490-491, 1991.

Bandini, et al., "Indium tribromide: a highly effective catalyst for the addition of trimethylsilyl cyanide to α-hetero-substituted ketone," Tetrahedron Letters, 42:3041-3043, 2001.

(56) References Cited

OTHER PUBLICATIONS

Barker, et al., "2,3,5-Tri-O-benzyl-D-ribosyl and -L-arabinosyl Bromides," Journal of Organic Chemistry, 26(11):4605-4609, 1961.
Belokon, et al., "Optimized catalysts for the asymmetric addition of trimethylsilyl cyanide to aldehydes and ketones," Tetrahedron, 57:771-779, 2001.
Benksim, et al., "A Novel Stereospecific Synthesis of Glycosyl Cyanides from 1,2-O-sulfinyl Derivatives," Organic Letters, 6(22):3913-3915, 2004.
Benzaria, et al., "Synthesis, In Vitro Antiviral Evaluation, and Stability Studies of Bis(S-acyl 2-thioethyl) Ester Derivatives of 9-[2-(phosphonomethoxy)ethyl]adenine (PMEA) as Potential PMEA prodrugs with Improved Oral Bioavailability," J. Med. Chem., vol. 39, No. 25, pp. 4958-4965 (1996).
Bio, et al., "Practical Synthesis of a Potent Hepatitis C Virus RNA Replication Inhibitor," J. Org. Chem., vol. 69, No. 19, pp. 6257-6266 (2004).
Bobeck, et al., "Advances in Nucleoside Monophosphate Prodrugs as Anti-HCV Agents," Antiviral Therapy, vol. 15, pp. 935-950 (2010).
Bojack, et al., "Design and Synthesis of Inhibitors of Adenosine and AMP Deaminases," Org. Lett., vol. 3, ; No. 6, pp. 839-842 (2001).
Boyer, et al., "Pathogenesis, diagnosis and management of hepatitis C," Journal of Hepatology, 32:98-112, 2000.
Brown, "Progress towards improving antiviral therapy for hepatitis C virus polymerase inhibitors. Part O: Nucleoside analogues," Expert Opinion, 18:709-725, 2009.
Butora, et al., "Synthesis and HCV inhibitory properties of 9-deaza- and 7,9-dideaza-7-oxa-2'C-methyladenosine," Bioorganic & Medicinal Chemistry, 15(15)5219-5229, 2007.
Cabirol, et al., "Robust and Efficient, yet Uncatalyzed, Synthesis of Triarylsilyl-protected Cyanohydrins from Ketones," Journal of Organic Chemistry, 73:2446-2449, 2008.
Calisher, et al., "Antigenic Relationships between Flaviviruses as Determined by Cross-neutralization Tests with Polyclonal Antisera," Journal of General Virology, 70:37-43, 1989.
Calès, et al., "Treatment of liver fibrosis: clinical aspects," Gastroentérologie Clinique et Biologique, 33(10-11):958-966, 2009.
Camps, "Studies on Structurally Simple -αβ-butenolides-II," Tetrahedron, 38(15):2395-2402, 1982.
Carroll, "Robust Antiviral Efficacy upon Administration of a Nucleoside Analog to Hepatitis C Virus-Infected Chimpanzees," Antimicrobial Agents and Chemotherapy, 53(3):926-934, 2009.
Chapman, et al., "RSV604, a Novel Inhibitor of Respiratory Syncytial Virus Replication," Antimicrobial Agents and Chemotherapy, 51(9):3346-53, 2007.
Cho, A., et al., (2012), "Synthesis and antiviral activity of a series of 1'-substituted 4-aza 7,9-dideazaadenosine C-nucleosides", Bioorg Med Chem Lett, 22:2705-7.
Cihlar, et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 52(2):655-65, 2008.
Clark, et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 48(17):5504-5508, 2005.
Colacino, et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 22(11):2013-2026, 2003.
Communication pursuant to Article 94(3) EPC for EP Patent Application No. 10763083.2, dated May 2, 2014.
Communication pursuant to Article 94(3) EPC for EP Patent Application No. 11715792.5, dated ; Feb. 14, 2014.
Communication under 161/162 for EP Patent Application No. 10704068.5, dated Sep. 6, 2011.
Communication under 161/162 for EP Patent Application No. 10763083.2, dated May 11, 2012.
Communication under 161/162 for EP Patent Application No. 11715792.5, dated Apr. 26, 2013.
Communication under 161/162 for EP Patent Application No. 11743400.1, dated Feb. 26, 2013.
Communication under 161/162 for EP Patent Application No. 11743709.5, dated Mar. 1, 2013.
Dai, et al., "Synthesis of 2'-C-β-Fluoromethyluridine," Organic Letters, 5(6):807-810, 2003.
De Clercq, "Antiviral Drugs: Current State of the Art," J. Clin. Virol., vol. 22, No. 1, pp. 73-89 (2001).
De Clercq, "Molecular Targets for Antiviral Agents," The Journal of Pharmacology and Experimental Therapeutics, vol. 297, No. 1, pp. 1-10 (2001).
De Francesco, et al., "Approaching a New Era for Hepatitis C Virus Therapy: Inhibitors of the NS3-4A Serine Protease and the NS5B RNA-Dependent RNA Polymerase," Antiviral Research, vol. 58, No. 1, pp. 1-16 (2003).
De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982:903-907, 1982.
De Lombaert, et al., "N-Phosphonomethyl Dipeptides and Their Phosphonate Prodrugs, a New Generation of Neutral Endopeptidase (NEP, EC 3.4.24.11) Inhibitors," J. Med. Chem., vol. 37, No. 4, ; pp. 498-511 (1994).
Di Bisceglie, et al., "The Unmet Challenges of Hepatitis C," Scientific American, Oct. 1999:80-85, 1999.
Dolzhenko, et al., "Pyrazolo[1,5-a][1,3,5]Triazines(5-Aza-9-Deazapurines): Synthesis and Biological Activity," Heterocycles, vol. 75, No. 7, pp. 1575-1622 (2008).
Domingo, et al., "The quasispecies (extremely heterogeneous) nature of viral RNA genome populations: biological relevance—a review," Gene, 40:1-8, 1985.
Dondoni, et al., "Thiazole-Based Synthesis of Formyl C-Glycosides," Journal of Organic Chemistry, 59:6404-6414, 1994.
Dudfield, et al., "Synthesis of C-ribosyl 1,2,4-triazolo[3,4-f][1,2,4]triazines as Inhibitors of Adenosine and AMP Deaminasses," J. Chem. Soc., Perkin Trans. 1, pp. 2937-2942 (1999).
Dudfield, et al., "Synthesis of C-ribosyl Imidazo [2,1-f ][1,2,4]triazines as Inhibitors of Adenosine and AMP Deaminases," J. Chem. Soc., Perkin Trans. 1, pp. 2929-2936 (1999).
Dymock, et al., "Novel approaches to the treatment of hepatitis C virus infection," Antiviral Chemistry & Chemotherapy, 11(2):79-96, 2000.
El Safadi, et al., "5-Modified-2'-dU and 2'-dC as Mutagenic Anti HIV-1 Proliferation Agents: Synthesis and Activity," Journal of Medicinal Chemistry, 53(4):1534-1545, 2010.
English translation of Office Action for MX Application No. MX/a/2013/003179, dated Feb. 25, 2014.
Extended European Search Report for EP Application No. 13194605.5, dated Mar. 13, 2014.
Farquhar, et al., "Biologically Reversible Phosphate-Protective Groups," Journal of Pharmaceutical Sciences, vol. 72, No. 3, pp. 324-325 (1983).
Final Rejection mailed Aug. 21, 2014 for U.S. Appl. No. 12/886,248.
First Examination Report (in English) for CO Patent Application No. 10-131479, dated Oct. 23, 2012.
First Examination Report (in English) for MX Patent Application No. MX/a/2010/011661, dated Oct. 26, 2011.
First Examination Report for AU Patent Application No. 2009240630, dated Jun. 14, 2012.
First Examination Report for AU Patent Application No. 2009240642, dated Aug. 2, 2012.
First Examination Report for CN Patent Application No. 200980120218.8, dated Nov. 13, 2012 ; (with English translation).
First Examination Report for CO Patent Application No. 10-121513-5, dated Dec. 10, 2012 ; (with English translation).
First Examination Report for EA Patent Application No. 201071128, dated Apr. 25, 2012 ; (with English translation).

(56) References Cited

OTHER PUBLICATIONS

First Examination Report for EA Patent Application No. 201071170, dated Apr. 25, 2012 (with English translation).
First Examination Report for ID Patent Application No. W00 2010 03923, dated Apr. 5, 2013 ; (with English translation).
First Examination Report for ID Patent Application No. W00 2010 03957, dated Apr. 25, 2013 ; (with English translation).
First Examination Report for IL Patent Application No. 208515, dated Jan. 6, 2013 (English translation).
First Examination Report for IL Patent Application No. 208701, dated Jan. 13, 2013 (English translation).
First Examination Report for JP Patent Application No. 2011-506429, dated Aug. 22, 2013 ; (with English translation).
First Examination Report for JP Patent Application No. 2011-506435, dated Aug. 22, 2013 ; (with English translation).
First Examination Report for NZ Patent Application No. 588400, dated Apr. 11, 2011.
First Examination Report for NZ Patent Application No. 588670, dated Apr. 8, 2011.
First Examination Report for NZ Patent Application No. 608070, dated Nov. 7, 2013.
First Examination Report for TW Patent Application No. 098113324, dated Oct. 30, 2012 ; (English translation).
First Examination Report for UA Patent Application No. 2010 13030, dated Mar. 2, 2013 ; (with English translation).
First Examination Report for VN Patent Application No. 1-2010-02653, dated Apr. 26, 2012 ; (with English translation).
First Examination Report for VN Patent Application No. 1-2010-02939, dated Apr. 19, 2012 ; (with English translation).
First Office Action for CL Patent Application No. 1906-2011, (with English translation).
First Office Action for CN Patent Application No. 201080011960.0, dated Jun. 8, 2013 (with English translation).
First Office Action for EA Patent Application No. 201190110/28, dated Apr. 26, 2012 (with English translation).
First Office Action for EA Patent Application No. 201390141/28, with English translation.
First Office Action for EP Patent Application No. 10704068.5, dated Jun. 18, 2012.
First Office Action for IL Patent Application No. 214396, dated Jul. 8, 2013 (English translation).
First Office Action for UA Application No. a 2011 10568, (with English translation).
First Office Action for VN Patent Application No. 1-2012-03895, dated Feb. 8, 2013 (and English translation).
Form 21 for AP Patent Application No. AP/P/2011/005818, dated Sep. 19, 2013.
Fukumoto, et al., "Viral Dynamics of Hepatiis C Early After Orthotopic Liver Transplantation: Evidence for Rapid Turnover of Serum Virions," Hepatology, 24:1351-1354, 1996.
Further Examination Report for NZ Application No. 594370, dated Oct. 8, 2013.
Garcia, et al., "Synthesis of (2,3,4,6-tetra-O-acetyl-alpha-D-glycopyranosyl)thiophene derivatives as new C-nucleoside analogues," J. Carbohydrate Chemistry 20(7/8)681-687, 2001.
Gardelli, et al., "Phosphoramidate Prodrugs of 2'-C-Methylcytidine for Therapy of Hepatitis C Virus Infection," Journal of Medicinal Chemistry, 52(17):5394-5407, 2009.
Gleeson, et al., "Prediction of the Potency of Inhibitors of Adenosine Deaminase by QM/MM Calculations," Chem. Commun., pp. 2180-2181 (2003).
Gordon, et al., "Control of Hepatitis C: A Medicinal Chemistry Perspective," J. Med. Chem., vol. 48, No. 1, ; pp. 1-20 (2005).
Greene, Protective Groups in Organic Synthesis (John Wiley & Sons, New York, 1991), 15pgs.
Gudmundsson, et al., "Synthesis of imidazo[1,2-a]pyridine C-Nucleosides with an Unexpected Site of Ribosylation," Journal of Organic Chemistry, 62:3453-3459, 1997.
Gudmundsson, et al., "The Condensation of 2,6-dichloroimidazo[1,2-a]pyridine C-nucleoside with an Unexpected Site of Ribosylation," Tetrahedron Letters, 37(14):2365-2368, 1996.
Gunic, et al.., "Cyclic monophosphate prodrugs of base-modified 2'-C-methyl ribonucleosides as potent inhibitors of hepatitis C virus RNA replication," Bioorganic & Medicinal Chemistry Letters, 17:2452-2455, 2007.
Hamann, et al., "Synthesis and antiviral evaluation of 7,9-dideaza-8-thiapurine C-nucleoside derivatives," Collection Symposium Series, 10:347-349, 2008.
Hamann, et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 17:2321-2326, 2009.
Han, et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 22(19):2815-2822, 1992.
Haraguchi, et al., "Stereoselective Synthesis of 1'-C-Branched Uracil Nucleosides From Uridine," Nucleosides & Nucleotides, vol. 14, No. 3-5, pp. 417-420 (1995).
Harki, et al., "Synthesis and Antiviral Activity of 5-Substituted Cytidine Analogues: Identification of Potent Inhibitor of Viral RNA-Dependent RNA Polymerases," Journal of Medicinal Chemistry, 49(21):6166-6169, 2006.
Hayashi, et al., "C-Nucleosides. 17. A Synthesis of 2-Substituted 7-(B-D-Ribofuranosyl)-Pyrrolo[2,1-f]-1,2,4-Triazines. A New Type of "Purine Like" C-Nucleoside," Heterocycles, vol. 34, No. 3, pp. 569-574 (1992).
Hecker, et al., "Liver Targeted Prodrugs of 2'-C-Methyladenosine for Therapy of Hepatitis C Virus Infection," J. Med. Chem., vol. 50, No. 16, pp. 3891-3896 (2007).
Hoffman, et al., "When, in the Context of Drug Design, Can a Fluorine Atom Successfully Substitute a Hydroxyl Group?," International Journal of Quantum Chemistry, 89:419-427, 2002.
International Preliminary Report on Patentability and Written Opinion for PCT International Application No. PCT/US2009/041432, mailed Oct. 26, 2010 (7 pages).
International Preliminary Report on Patentability and Written Opinion for PCT International Application No. PCT/US2010/049471, mailed Mar. 27, 2012 (7 pages).
International Preliminary Report on Patentability and Written Opinion for PCT International Application No. PCT/US2010/049508, mailed Mar. 27, 2012 (6 pages).
International Preliminary Report on Patentability and Written Opinion for PCT International Application No. PCT/US2011/038253, mailed Dec. 4, 2012 (6 pages).
International Preliminary Report on Patentability and Written Opinion for PCT International Application No. PCT/US2011/044581, mailed Jan. 22, 2013 (7 pages).
International Preliminary Report on Patentability for PCT International Application No. PCT/US2009/041447, mailed Oct. 26, 2010 (7 pages).
International Preliminary Report on Patentability for PCT International Application No. PCT/US2010/023586, mailed Aug. 16, 2011 (6 pages).
International Preliminary Report on Patentability for PCT International Application No. PCT/US2011/028897, mailed Mar. 26, 2013 (7 pages).
International Preliminary Report on Patentability for PCT International Application No. PCT/US2011/029441, mailed Mar. 26, 2013 (7 pages).
International Preliminary Report on Patentability for PCT International Application No. PCT/US2011/045102, mailed Jan. 22, 2013 (5 pages).
International Search Report for PCT International Application No. PCT/US2010/023586, mailed Aug. 4, 2010 (4 pages).
International Search Report for PCT International Application No. PCT/US2011/038253, mailed Jul. 29, 2011 ; (4 pages).
International Search Report for PCT International Application No. PCT/US2011/044581, mailed ; Nov. 7, 2011 (4 pages).
International Search Report for PCT International Application No. PCT/US2009/041432, mailed Aug. 11, 2009 (5 pages).

(56) References Cited

OTHER PUBLICATIONS

International Search Report issued in International Application No. PCT/US2009/041447, mailed Aug. 7, 2009 (5 pages).
International Search Report issued in International Application No. PCT/US2010/049471, mailed Nov. 18, 2010 (5 pages).
International Search Report issued in International Application No. PCT/US2010/049508, mailed Nov. 5, 2010 (4 pages).
International Search Report issued in International Application No. PCT/US2011/028897, mailed Aug. 1, 2011 (6 pages).
International Search Report issued in International Application No. PCT/US2011/029441, mailed Aug. 1, 2011 (5 pages).
International Search Report issued in International Application No. PCT/US2011/045102, mailed Nov. 9, 2011 (4 pages).
Itoh, et al., "Divergent and Stereocontrolled Approach to the Synthesis of Uracil Nucleosides Branched at the Anomeric Position," J. Org. Chem., vol. 60, No. 3, pp. 656-662 (1995).
Jasko, et al., "5'-Phosphonates of Ribonucleosides and 2'-Deoxyribonucleosides: Synthesis and Antiviral Activity," Nucleosides & Nucleotides, 12(8):879-893, 1993.
Kabat, et al., "Nucleosides, CXLVIII, Synthesis of 6-(β-D-Ribofuranosyl)picolinamide: A Novel C-Nucleoside from D-Ribonolactone," Chemical & Pharmaceutical Bulletin, 36(2):634-640, 1988.
Khamnei, et al., "Neighboring Group Catalysis in the Design of Nucleotide Prodrugs," J. Med. Chem., vol. 39, No. 20, pp. 4109-4115 (1996).
Klumpp, et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 281(7):3793-3799, 2006.
Knutsen, et al., "Synthesis of Imidazo-fused Bridgehead-nitrogen 2'-Deoxyribo-C-nucleosides: Coupling-Elimination Reactions of 2,5-Anhydro-3,4,6-tri-O-benzoyl-o-allonic Acid," J. Chem. Soc., Perkin Trans. 1, ; pp. 621-630 (1985).
Knutsen, et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc., Perkin Trans 1, pp. 229-238 (1984).
Kobe, et al., "Use of Distance Geometry Approach for the In Vitro Antiviral Activity Evaluation of N-bridgehead C-nucleosides," European J. Med. Chem., vol. 27, No. 3, pp. 259-266 (1992).
Lefebvre, et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 38(20):3941-3950, 1995.
Lefebvre, et al., "Synthesis, Decomposition Pathways and 'In Vitro' Evaluation of Bioreversible Phosphotriesters of Azt," Nucleosides, Nucleotides & Nucleic Acids, 14(3-5):763-766, 1995.
Lindell, et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 1(6):286-289, 2010.
Lovelette, C.A., "1,2,4-Triazines. Synthesis of selected members of the S-triazolo[3,4-f][1,2,4]triazine and tetrazolo[1,5-f][1,2,4]triazine ring systems," *Journal of Heterocyclic Chemistry*, 16:555-560, 1979.
Martell, et al., "Hepatitis C Virus (HCV) Circulates as a Population of Different but Closely Related Genomes: Quasispecies Nature of HCV Genome Distribution," Journal of Virology, 6695:3225-3229, 1992.
Mason, et al., "Polyadenylation-dependent screening assay for respiratory syncytial virus RNA transcriptase activity and identification of an inhibitor," Nucleic Acids Research, 32(16):4758-4767, 2004.
Matulic-Adamic, et al., "Synthesis of 3-(β-D-Ribofuranosyl)-2-Fluoropyridine and 3-(β-D-Ribofuranosyl)-Pyridin-2-one," Tetrahedron Letters, 38(2):203-206, 1997.

Matulic-Adamic, et al., "Synthesis of 5-(β-D-Ribofuranosyl)-Pyridin-2-one: a 'Deletion-Modified' Analogue of Uridine," Tetrahedron Letters, 38(10):1669-1672, 1997.
Mcguigan, C., et al., "Intracellular Delivery of Bioactive AZT Nucleotides by Aryl Phosphate Derivatives of AZT," J. Med. Chem., vol. 36, No. 8, pp. 1048-1052 (1993).
Meppen, et al., "Cyclic phosphoramidates as prodrugs of 2'-C-methylcytidine," European Journal of Medicinal Chemistry, 44(9):3765-3770, 2009.
Meppen, et al., "Medi-404—A Prodrug Approach for the Treatment of HCV Infection," Abstracts of papers, 236th ACS National Meeting, Philadelphia, PA, United States, Aug. 17-21, 2008.
Metobo, S., et al., (2011), "Practical synthesis of 10-substituted Tubercidin C-nucleoside analogs", *Tetrahedron Letters*, 53:484-6.
Migliaccio, et al., "Characterization of Resistance to Non-obligate Chain-terminating Ribonucleoside Analogs That Inhibit Hepatitis C Virus Replication in vitro," The Journal of Biological Chemistry, 278(49):49164-49170, 2003.
Mitchell, et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, pp. 2345-2353 (1992).
Mitchell, et al., "Synthesis of C-Nucleoside Isosteres of 9-(2-Hydroxyethoxymethyl)guanine (Acyclovir)," ; J. Het. Chem., vol. 21, No. 3, pp. 697-699 (1984).
Moennig, et al., "The Pestiviruses," Advances in Virus Research, vol. 41, pp. 53-98 (1992).
Moradpour, et al., "Replication of hepatitis C virus," Nature Reviews Microbiology, 5(6):453-463, 2007.
Moscow, et al., "Reduced Folate Carrier Gene (RFC1) Expression and Anti-Folate Resistance in Transfected and Non-Selected Cell Lines," International Journal of Cancer, 72:184-190, 1997.
Murakami, et al., "Mechanism of Activation of Beta-D-2'-Fluoro-2'-C-Methylcytidine and Inhibition of Hepatitis C Virus NS5B RNA Polymerase," Antimicrob Agents Chemother. 51(2):503-509, Feb. 2007.
Neumann, et al., "Hepatitis C Viral Dynamics in Vivo and the Antiviral Efficacy of Interferon-α Therapy," Science, 282:103-107, 1998.
Nishimura, et al., "Synthesis of pyrrolo[2,1-f][1,2,4]triazine C-nucleosides, Isosteres of sangivamycin, tubercidin, and toyocamycin," Carbohydrate Research, vol. 331, No. 1, pp. 77-82 (2001).
Notice of Allowance mailed Apr. 12, 2011 for U.S. Appl. No. 12/428,176.
Notice of Allowance mailed Apr. 26, 2011 for U.S. Appl. No. 12/702,957.
Notice of Allowance mailed Apr. 7, 2011 for U.S. Appl. No. 12/428,234.
Notice of Allowance mailed Aug. 10, 2012 for U.S. Appl. No. 13/117,060.
Notice of Allowance mailed Feb. 13, 2014 for U.S. Appl. No. 13/649,511.
Notice of Allowance mailed Feb. 17, 2011 for U.S. Appl. No. 12/885,917.
Notice of Allowance mailed Jan. 31, 2013 for U.S. Appl. No. 13/050,820.
Notice of Allowance mailed Jan. 6, 2011 for U.S. Appl. No. 12/428,176.
Notice of Allowance mailed Jul. 16, 2012 for U.S. Appl. No. 13/196,117.
Notice of Allowance mailed Jun. 3, 2014 for U.S. Appl. No. 13/649,511.
Notice of Allowance mailed Mar. 27, 2012 for U.S. Appl. No. 13/196,117.
Notice of Allowance mailed Nov. 28, 2012 for U.S. Appl. No. 13/117,060.
Notice of Reasons for Rejection for JP Application No. 2011-549324, dated Jul. 28, 2014 ; (with English translation).
Notice of Reasons for Rejection for JP Application No. 2011-549324, dated Mar. 26, 2014 ; (with English translation).

(56) References Cited

OTHER PUBLICATIONS

Notification of Defects for IL Patent Application No. 208515, dated Aug. 25, 2014 (English translation).
Notification of Defects for IL Patent Application No. 214396, dated Nov. 11, 2013 (English translation).
Notification of Defects for IL Patent Application No. 218599, dated Aug. 25, 2014 (English translation).
Notification of Defects for IL Patent Applicaton No. 208701, dated Aug. 25, 2014 (English translation).
Notification of Reasons for Rejection for JP Patent Application No. 2012-529958, dated Aug. 5, 2014.
Notification of Reasons for Rejection for JP Patent Application No. 2012-529963, dated Aug. 28, 2014 ; (with English translation).
Notification of Reexamination for CN Patent Application No. 200980120218.8, dated Sep. 1, 2014 ; (with English translation).
Notification of the First Office Action and Search Report for CN Patent Application No. 201080041902.X, dated ; Nov. 12, 2013 (with English translation).
Notification of the First Office Action for CN Patent Application No. 201080041946.2, dated Dec. 18, 2013 ; with Search Report (+ English translation).
Notification of the First Office Action for CN Patent Application No. 201180035776.1, dated Feb. 27, 2014 ; (with English translation).
Notification of the Second Office Action & Search Report for CN Patent Application No. 201080011690.0, dated ; Jan. 8, 2014 (with English translation).
Notification of the Third Office Action for CN Patent Application No. 201080011690.0, dated Jul. 29, 2014 ; (with English translation).
Notification Prior to Examination for IL Patent Application No. 218599, dated Nov. 13, 2012 ; (English translation).
Notification Prior to Examination for IL Patent Application No. 218752, dated Jan. 20, 2014 (English translation (3 pages)).
Office Action (Restriction Requirement) mailed Sep. 14, 2012 for U.S. Appl. No. 12/886,248.
Office Action dated Sep. 24, 2014 for U.S. Appl. No. 13/813,886.
Office Action for CA Patent Application No. 2,773,772, dated Aug. 12, 2014.
Office Action for CN Patent Application No. 200980114224.2, dated Aug. 19, 2013 (with English translation).
Office Action for CN Patent Application No. 200980114224.2, dated Nov. 30, 2012 (with English translation).
Office Action for CO Application No. 13 004212, dated Dec. 4, 2013 (+ English translation).
Office Action for CO Patent Application No. 11-109.501 dated Nov. 27, 2012 (English translation).
Office Action for CO Patent Application No. 13-235103-1 (English translation).
Office Action for EA Patent Application No. 201390152, dated Apr. 14, 2014 (and English translation).
Office Action for MX Application No. MX/a/2011/008409, dated Mar. 25, 2014 (with English translation).
Office Action for MX Application No. MX/a/2013/000656, dated Apr. 22, 2014 (+ English translation).
Office Action for MX Application No. MX/a/2013/000656, dated Aug. 4, 2014 (and English translation).
Office Action for MX Application No. MX/a/2013/000744, dated Apr. 22, 2014 (and English translation).
Office Action in PE Application No. 1464 dated Sep. 12, 2013 (with English translation).
Office Action mailed Aug. 15, 2013 for U.S. Appl. No. 13/649,511.
Office Action mailed Dec. 23, 2010 for U.S. Appl. No. 12/428,234.
Office Action mailed Dec. 23, 2010 for U.S. Appl. No. 12/702,957.
Office Action mailed Jan. 22, 2013 for U.S. Appl. No. 13/649,511.
Office Action mailed Mar. 27, 2012 for U.S. Appl. No. 13/050,820.
Office Action mailed Mar. 4, 2013 for U.S. Appl. No. 12/886,248.
Office Action mailed Nov. 6, 2012 for U.S. Appl. No. 12/886,248.
Office Action mailed Oct. 16, 2012 for U.S. Appl. No. 13/050,820.
Office Action mailed Sep. 23, 2011 for U.S. Appl. No. 13/196,117.

Office Action No. 425 for CO Patent Application No. 12 050 579, dated Jan. 21, 2014 ; (with English translation).
Office Action with Search Report for TW Patent Application No. 099131868, dated May 22, 2014 ; (with English translation).
Office Action with Search Report for TW Patent Application No. 102115415, dated May 15, 2014 ; (with English translation).
Office Action with Search Report, dated Jun. 27, 2014 for CN Patent Application No. 201180035281.9 (with English translation).
Official Action (ARIPO Form No. 18) with Substantive Search and Examination Report for AP Application No. AP/P/2010/005414, dated Mar. 14, 2014 (6 pages).
Official Action for EA Patent Application No. 201390133, dated Mar. 27, 2014 (and English translation).
Official Action for SV National Phase Entry of International Application No. PCT/US2010/049471, dated ; Nov. 6, 2013 (with English translation).
Ogura, et al., "Reaction of Ethynyl Compounds with Lactones," Journal of Organic Chemistry, 37(1):72-75, 1972.
Opposition filed Against CL Patent Application 00076-2013, dated Jun. 18, 2014, with English translation.
Opposition for CL Patent Application No. 727-2013, dated Oct. 15, 2013 with English translation.
Opposition for EC Patent Application No. SP-13-12451, date of Notification Apr. 23, 2014 ; (and English translation).
Opposition for EC Patent Application No. SP-2012-11817, dated May 27, 2013.
Otter, et al., "Conformational Properties of Purine-Like C-Nucleosides," Nucleosides & Nucleotides, vol. 15, No. 1-3, pp. 793-807 (1996).
Pankiewicz, et al., "C-Nucleoside Analogues of Nicotinamide Mononucleotide (NMN)," Nucleosides and Nucleotides, 7(5 &6):589-593, 1988.
Pankiewicz, et al., "Efficient Synthesis of 5-(β-D-Ribofuranosyl)nicotinamide and its α-Isomer," Journal of Organic Chemistry, 53:3473-3479, 1988.
Patent Examination Report No. 1 for AU Application No. 2011280910, dated Jun. 10, 2014.
Patent Examination Report No. 1 for AU Application No. 2011306066, dated Nov. 21, 2013.
Patent Examination Report No. 1 for AU Patent Application No. 2010213873, Jun. 4, 2014.
Patent Examination Report No. 1 for AU Patent Application No. 2010295392, dated Sep. 16, 2014.
Patent Examination Report No. 1 for AU Patent Application No. 2011282241, dated Jul. 9, 2014.
Patil, et al., "4-Aza-7,9-Dideazaadenosine, a New Cytotoxic Synthetic C-Nucleoside Analogue of Adenosine," Tet. Lett., vol. 35, pp. 5339-5342 (1994).
Patil, et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 9(7):937-956, 1990.
Patil, et al., "Synthesis of Pyrrolo[2,1-f][1,2,4]triazine Congeners of Nucleic Acid Purines via the N-Amination of 2-Substituted Pyrroles," J. Het. Chem., vol. 31, pp. 781-786 (1994).
Patil, et al., "Synthesis of some new thieno[3,4-d]pyrimidines and their C-nucleosides," Journal of Heterocyclic Chemistry, 30(2):509-515, 1993.
Perrone, et al., "Application of the Phosphoramidate ProTide Approach to 4'-Azidouridine Confers Sub-micromolar Potency versus Hepatitis C Virus on an Inactive Nucleoside," Journal of Medicinal Chemistry, 50(8):1840-1849, 2007.
Piccirilli, et al., "A Direct Route to 3-(D-Ribofuranosyl)pyridine Nucleosides," Helvetica Chimica Acta, 74:397-406, 1991.
Pierra, et al., "Synthesis and Pharmacokinetics of Valopicitabine (NM283), and Efficient Prodrug of the Potent Anti-HCV Agent 2'-C-Methylcytidine," Journal of Medicinal Chemistry, 49(22):6614-6620, 2006.
Poduch, et al., "Design of Inhibitors of Orotidine Monophosphate Decarboxylase Using Bioisosteric Replacement and Determination of Inhibition Kinetics," Journal of Medicinal Chemistry, 49(16):4937-4945, 2006.

(56) References Cited

OTHER PUBLICATIONS

Puech, et al., "Intracellular Delivery of Nucleoside Monophosphates through a Reductase-mediated Activation Process," Antiviral Research, vol. 22, No. 4, pp. 155-174 (1993).
Ramasamy, et al., "Synthesis and Antitumor Activity of Certain 3-B-D-Ribofuranosyl-1,2,4-triazol[3,4-f]-1,2,4-triazines Related to Formycin Prepared via Ring Closure of a 1,2,4-Triazine Precursor," J. Med. Chem., vol. 29, No. 11, pp. 2231-2235 (1986).
Rao, et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, ; 29(29):3537-3540, 1988.
Reddy, et al., "Stereoselective Synthesis of Nucleoside Monophosphate HepDirectTM Prodrugs," Tet. Lett., vol. 46, pp. 4321-4324 (2005).
Rejection Decision for CN Patent Application No. 200980120218.8, dated Feb. 7, 2014 ; (with English translation).
Resolution No. 56673 for CO Patent Application No. 10-131479, dated Sep. 27, 2013 with ; English translation.
Resolution No. 72986 for CO Patent Application No. 10-121513-5, (12 pages) ; (English translation).
Schul, et al., "A Dengue Fever Viremia Model in Mice Shows Reduction in Viral Replication and Suppression of the Inflammatory Response after Treatment with Antiviral Drugs," Journal of Infectious Diseases, vol. 195, pp. 665-674 (2007).
Schultz, "Prodrugs of Biologically Active Phosphate Esters," Bioorganic & Medicinal Chemistry, ; 11:885-898, 2003.
Scott, et al., "Interferon-a-2b Plus Ribavirin: A Review of its Use in the Management of Chronic Hepatitis C," Drugs, vol. 62, No. 3, pp. 507-556 (2002).
Search and Exam Report for AP Application No. AP/P/2012/006189, dated Jun. 26, 2014.
Search Report for AP Patent Application No. AP/P/2011/005818, dated Sep. 19, 2013.
Second Examination Report (in English) for CO Patent Application No. 10-131479, dated Jun. 20, 2013.
Second Examination Report and Notice of Acceptance for NZ Patent Application No. 588400 dated Jul. 27, 2012.
Second Examination Report for CN Patent Application No. 200980120218.8, dated Jun. 21, 2013 ; (with English translation).
Second Examination Report for EA Patent Application No. 201071128, dated Oct. 24, 2012 ; (with English translation).
Second Examination Report for EA Patent Application No. 201071170, dated Oct. 25, 2012 ; (with English translation).
Second Examination Report for VN Patent Application No. 1-2010-02939, dated Jul. 26, 2012 ; (with English translation).
Second Office Action for CL Patent Application No. 1906-2011, Oct. 16, 2013 (with English translation).
Second Office Action for EA Patent Application No. 201190110/28, dated Jan. 28, 2013 ; (with English translation).
Second Office Action for UA Patent Application No. 2011 10568, dated Aug. 11, 2014 (and English translation).
Shekunov, et al., "Crystallization processes in pharmaceutical technology and drug delivery design", ; Journal of Crystal Growth, 211:122-136 (2000).
Silverman et al., *The Organic Chemistry of Drug Design and Drug Action*, 19-23, 1992.
Silverman, "The Organic Chemistry of Drug Design and Drug Action," 2nd Ed., pp. 29-34 (2004).
Srivastav, et al., "Antiviral Activity of Various 1-(2'-Deoxy-β-D-lyxofuranosyl), 1-(2'-Fluoro-β-D-xylofuranosyl), 1-(3'-Fluor-α -D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 53(19):7156-7166, 2010.
Statement of Opposition, Mar. 31, 2011, with English translation, for EC Patent Application No. SP-10-10609.
Substantive Examination Report Stage 1 (with English translation) for ID Application No. W-00201103126.
Supplement to First Examination Report for IL Patent Application No. 208515, dated Jan. 15, 2013 ; (English translation).
Tapia, et al., "Combination of a Mutagenic Agent with a Reverse Transcriptase Inhibitor Results in Systematic Inhibition of HIV-1 Infection," Virology, 338:1-8, 2005.
Third Examination Report for EA Patent Application No. 201071128, dated Apr. 29, 2013 ; (with English translation).
Third Examination Report for EA Patent Application No. 201071170, dated Oct. 10, 2013 ; (with English translation).
Third Office Action for EA Application No. 201190110/28, dated Oct. 18, 2013.
Uchiyama, et al., "O-selective Phosphorylation of Nucleosides without N-protection," J. Org. Chem. 58(2), Jan. 1, 1993.
Vaghefi, et al., "Synthesis and Antiviral Activity of Certain Nucleoside 5'-Phosphonoformate Derivatives," Journal of Medicinal Chemistry, 29(8):1389-1393, 1986.
Written Opinion and ISR for International Application No. PCTUS2015057933, dated Jan. 21, 2016, 9 pgs.
Written Opinion and ISR for PCT International Application No. PCT/ US2015/057934, mailed May 6, 2016, 20pgs.
Written Opinion and ISR for PCT International Application No. PCT/US2015/057932, dated May 6, 2016, 17 pgs.
Written Opinion for PCT International Application No. PCT/US2010/023586, mailed Aug. 4, 2010 (5 pages).
Written Opinion for PCT International Application No. PCT/US2011/028897, mailed Aug. 1, 2011 (6 pages).
Written Opinion for PCT International Application No. PCT/US2011/029441, mailed Aug. 1, 2011 (6 pages).
Written Opinion for PCT International Application No. PCT/US2011/038253, mailed Jul. 29, 2011 (5 pages).
Written Opinion for PCT International Application No. PCT/US2011/044581, mailed Nov. 7, 2011 (6 pages).
Written Opinion for PCT International Application No. PCT/US2011/045102, mailed Nov. 9, 2011 ; (4 pages).
Written Opinion issued in International Application No. PCT/US2009/041447, dated Oct. 26, 2010 (7 pages).
Written Opinion issued in International Application No. PCT/US2010/049471, dated Mar. 27, 2012 (7 pages).
Written Opinion issued in International Application No. PCT/US2010/049508, dated Mar. 27, 2012 (6 pages).
Written Opinion issued in International Application No. PCT/US2011/045102, dated Jan. 22, 2013 (5 pages).
Wu, et al., "Synthetic Methodologies for C-Nucleosides," Synthesis, 10:1533-1553, 2004.
Yamanaka, et al., "Metabolic Studies on BMS-200475, a New Antiviral Compound Active against Hepatitis B Virus," Antimicrobial Agents and Chemotherapy, 43(1):190, 1999.
Yoshimura, et al., "Synthesis and Biological Evaluation of 1'-C-Cyano-Pyrimidine Nucleosides," Nucleosides & Nucleotides, vol. 15, No. 1-3, pp. 305-324 (1996).
Zhang, et al., "A Practical Synthesis of (2R)-3,5-di-O-benzoyl-2-fluoro-2-C-methyl-D-ribono-y-lactone," Tetrahedron: Asymmetry, 20:305-312, 2009.
Office Action dated Jul. 21, 2016 for U.S. Appl. No. 14/613,719.
Office Action dated Nov. 4, 2016 for U.S. Appl. No. 14/613,719.
Pre-Appeal Brief dated Feb. 6, 2017 for U.S. Appl. No. 14/613,719.
Pre-Appeal Decision dated Mar. 14, 2017 for U.S. Appl. No. 14/613,719.
Warren, T., et al., (2016), "Therapeutic efficacy of the small molecule GS-5734 against Ebola virus in rhesus monkeys", *Nature*, 531:381-5.

\* cited by examiner

METHODS FOR TREATING *FILOVIRIDAE* VIRUS INFECTIONS

CROSS-REFERENCES TO RELATED APPLICATIONS

This patent application claims the benefit under 35 U.S.C. §119(e) of U.S. Provisional Patent Application No. 62/072,331, filed Oct. 29, 2014, and U.S. Provisional Patent Application No. 62/105,619, filed Jan. 20, 2015. The foregoing patent applications are incorporated herein by reference in their entireties.

FIELD OF THE INVENTION

The invention relates generally to methods and compounds for treating Filoviridae virus infections, particularly methods and nucleosides for treating Ebola virus, Marburg virus and Cueva virus.

BACKGROUND OF THE INVENTION

Filoviruses (e.g., Ebola virus (EBOV) and Marburg virus (MARV)) are among the most lethal and destructive viruses. They cause severe, often fatal viral hemorrhagic fevers in humans and nonhuman primates (e.g., monkeys, gorillas, and chimpanzees). Filoviruses are of particular concern as possible biological weapons since they have the potential for aerosol dissemination and weaponization.

The incubation period for Filovirus infection ranges from 2 to 21 days. The onset of illness is abrupt and is characterized by high fever, headaches, joint and muscle aches, sore throat, fatigue, diarrhea, vomiting, and stomach pain. A rash, red eyes, hiccups and internal and external bleeding may be seen in some patients. Within one week of becoming infected with the virus, most patients experience chest pains and multiple organ failure, go into shock, and die. Some patients also experience blindness and extensive bleeding before dying.

Filoviridae are a family of RNA viruses. Two members of the Filoviridae family have been identified: EBOV and MARV. Two key pathogenic types of the Filoviridae family have been identified: Ebolavirus and MARV. There is one identified variant of MARV and five identified species of ebolavirus: Zaire (i.e. Ebola virus, EBOV), Sudan, Tai Forest, Bundibugyo, and Reston. The exact origin, locations, and natural habitat of Filoviridae are unknown. However, on the basis of available evidence and the nature of similar viruses, it is postulated that Filoviridae are zoonotic (i.e., animal-borne) and are normally maintained in an animal host that is native to the African continent.

For more than 30 years, ebolaviruses have been associated with periodic episodes of hemorrhagic fever in Central Africa that produce severe disease in infected patients. Mortality rates in outbreaks have ranged from 50% for the Sudan species of ebolavirus (SEBOV) to up to 90% for the Zaire species of ebolavirus (EBOV, ZEBOV) (Sanchez et al., Filoviridae: Marburg and Ebola Viruses, in *Fields Virology* (eds. Knipe, D. M. & Howley, P. M.) 1409-1448 (Lippincott Williams & Wilkins, Philadelphia)). An outbreak late in 2007 caused by an apparently new species of ebolavirus in Uganda resulted in a fatality rate of about 25% (Towner et al., *PLoS Pathog.*, 4:e1000212 (2008)). ZEBOV has also decimated populations of wild apes in this same region of Africa (Walsh et al., *Nature*, 422:611-614 (2003)).

Prevention and treatment of Filovirus infections, including ebolaviruses (i.e. EBOV) presents many challenges. In fact, there are no vaccines or post exposure treatment modalities available for preventing or managing EBOV infections. Patients instead receive supportive therapy, i.e., electrolyte and fluid balancing, oxygen, blood pressure maintenance, and treatment for any secondary infections.

Thus, there is a need for compositions and methods for treating EBOV infections. The present invention addresses these and other needs.

SUMMARY OF THE INVENTION

Provided, is a method for treating a Filoviridae infection in a human in need thereof comprising administering a therapeutically effective amount of a compound of Formula IV:

Formula IV or a pharmaceutically acceptable salt, hydrate or ester, thereof;

wherein, $R^7$ is selected from the group consisting of a) H, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)$_2$(O$R^{11}$), or —SO$_2$N$R^{11}R^{12}$;

b)

c) a group selected from:

-continued

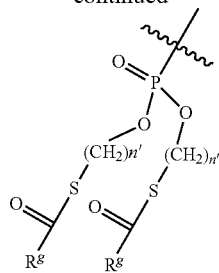

wherein:
R$^c$ is selected from the group of phenyl, 1-naphthyl, 2-naphthyl,

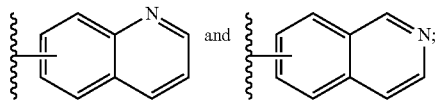

R$^d$ is selected from the group of H or CH$_3$;
R$^{e1}$ and R$^{e2}$ are each independently selected from the group of H, (C$_1$-C$_6$)alkyl or benzyl;
R$^f$ is selected from the group of from H, (C$_1$-C$_8$) alkyl, benzyl, (C$_3$-C$_6$)cycloalkyl, and —CH$_2$—(C$_3$-C$_6$)cycloalkyl;
R$^g$ is selected from the group of (C$_1$-C$_8$)alkyl, —O—(C$_1$-C$_8$)alkyl, benzyl, —O-benzyl, —CH$_2$—(C$_3$-C$_6$)cycloalkyl, —O—CH$_2$—(C$_3$-C$_6$)cycloalkyl, and CF$_3$; and
n' is an integer selected from the group of 1, 2, 3, and 4; and
d) a group of the formula:

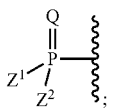

wherein:
Q is selected from the group of O, S, NR, $^+$N(O)(R), N(OR), $^+$N(O)(OR), or N—NR$_2$;
Z$^1$ and Z$^2$, when taken together, are -Q$^1$(C(R$^y$)$_2$)$_3$Q$^1$-;
wherein
each Q$^1$ is independently selected from the group of O, S, or NR; and
each R$^y$ is independently selected from the group of H, F, Cl, Br, I, OH, R, —C(=Q$^2$)R, —C(=Q$^2$)OR, —C(=Q$^2$)N(R)$_2$, —N(R)$_2$, —$^+$N(R)$_3$, —SR, —S(O)R, —S(O)$_2$R, —S(O)(OR), —S(O)$_2$(OR), —OC(=Q$^1$)R, —OC(=Q$^2$)OR, —OC(=Q$^2$)(N(R)$_2$), —SC(=Q$^2$)R, —SC(=Q$^2$)OR, —SC(=Q$^2$)(N(R)$_2$), —N(R)C(=Q$^2$)R, —N(R)C(=Q$^2$)OR, —N(R)C(=Q$^2$)N(R)$_2$, —SO$_2$NR$_2$, —CN, —N$_3$, —NO$_2$, —OR, or Z$^3$; or when taken together, two R$^y$ on the same carbon atom form a carbocyclic ring of 3 to 7 carbon atoms;
each Q$^2$ is independently, O, S, NR, $^+$N(O)(R), N(OR), $^+$N(O)(OR), or N—NR$_2$; or Z$^1$ and Z$^2$ are each, independently, a group of the Formula Ia:

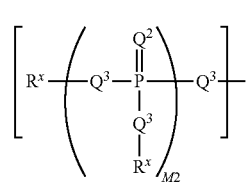

Formula Ia wherein:
each Q$^3$ is independently selected from the group of a bond, O, CR$_2$, NR, $^+$N(O)(R), N(OR), $^+$N(O)(OR), N—NR$_2$, S, S—S, S(O), or S(O)$_2$;
M2 is an integer selected from the group of 0, 1 or 2;
each R$^x$ is independently R$^y$ or the formula:

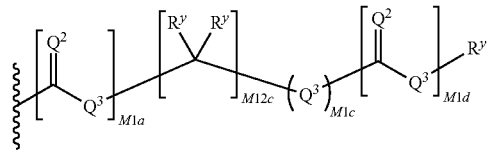

wherein:
each M1a, M1c, and M1d is an integer independently selected from the group of 0 or 1;
M12c is an integer selected from the group of 0, 1, 2, 3, 4, 5, 6, 7, 8, 9, 10, 11 or 12;
Z$^3$ is Z$^4$ or Z$^5$;
Z$^4$ is R, —C(Q$^2$)R$^y$, —C(Q$^2$)Z$^5$, —SO$_2$R$^y$, or —SO$_2$Z$^5$; and
Z$^5$ is a carbocycle or a heterocycle wherein Z$^5$ is independently substituted with 0 to 3 R$^y$ groups;
each R$^{11}$ or R$^{12}$ is independently H, (C$_1$-C$_8$)alkyl, (C$_2$-C$_8$)alkenyl, (C$_2$-C$_8$)alkynyl, (C$_4$-C$_8$)carbocyclylalkyl, (C$_6$-C$_{20}$)optionally substituted aryl, optionally substituted heteroaryl, —C(=O)(C$_1$-C$_8$)alkyl, —S(O)$_n$(C$_1$-C$_8$)alkyl or (C$_6$-C$_{20}$)aryl(C$_1$-C$_8$)alkyl; or R$^{11}$ and R$^{12}$ taken together with a nitrogen to which they are both attached form a 3 to 7 membered heterocyclic ring wherein any one carbon atom of said heterocyclic ring can optionally be replaced with —O—, —S— or —NR$^a$—;
each R$^a$ is independently selected from the group of H, (C$_1$-C$_8$)alkyl, (C$_2$-C$_8$)alkenyl, (C$_2$-C$_8$)alkynyl, (C$_6$-C$_{20}$)aryl(C$_1$-C$_8$)alkyl, (C$_4$-C$_8$)carbocyclylalkyl, —C(=O)R, —C(=O)OR, —C(=O)NR$_2$, —C(=O) SR, —S(O)R, —S(O)$_2$R, —S(O)(OR), —S(O)$_2$(OR), or —SO$_2$NR$_2$; wherein
each R is independently selected from the group of H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, (C$_6$-C$_{20}$)aryl, (C$_6$-C$_{20}$)substituted aryl, (C$_2$-C$_{20}$)heterocyclyl, (C$_2$-C$_{20}$)substituted heterocyclyl, (C$_6$-C$_{20}$)aryl(C$_1$-C$_8$)alkyl or substituted (C$_6$-C$_{20}$)aryl(C$_1$-C$_8$)alkyl;
each n is an integer independently selected from the group of 0, 1, or 2; and
wherein each (C$_1$-C$_8$)alkyl, (C$_2$-C$_8$)alkenyl, (C$_2$-C$_8$)alkynyl or (C$_6$-C$_{20}$)aryl(C$_1$-C$_8$)alkyl of each R$^{11}$ or R$^{12}$ is, independently, optionally substituted with one or more substituents selected from the group of halo, hydroxy, CN, $N_3$, $N(R^a)_2$ or $OR^a$; and wherein one or more of the non-terminal carbon atoms of each said $(C_1-C_8)$alkyl may be optionally replaced with —O—, —S— or —$NR^a$—.
In another embodiment, the present invention provides a compound that is
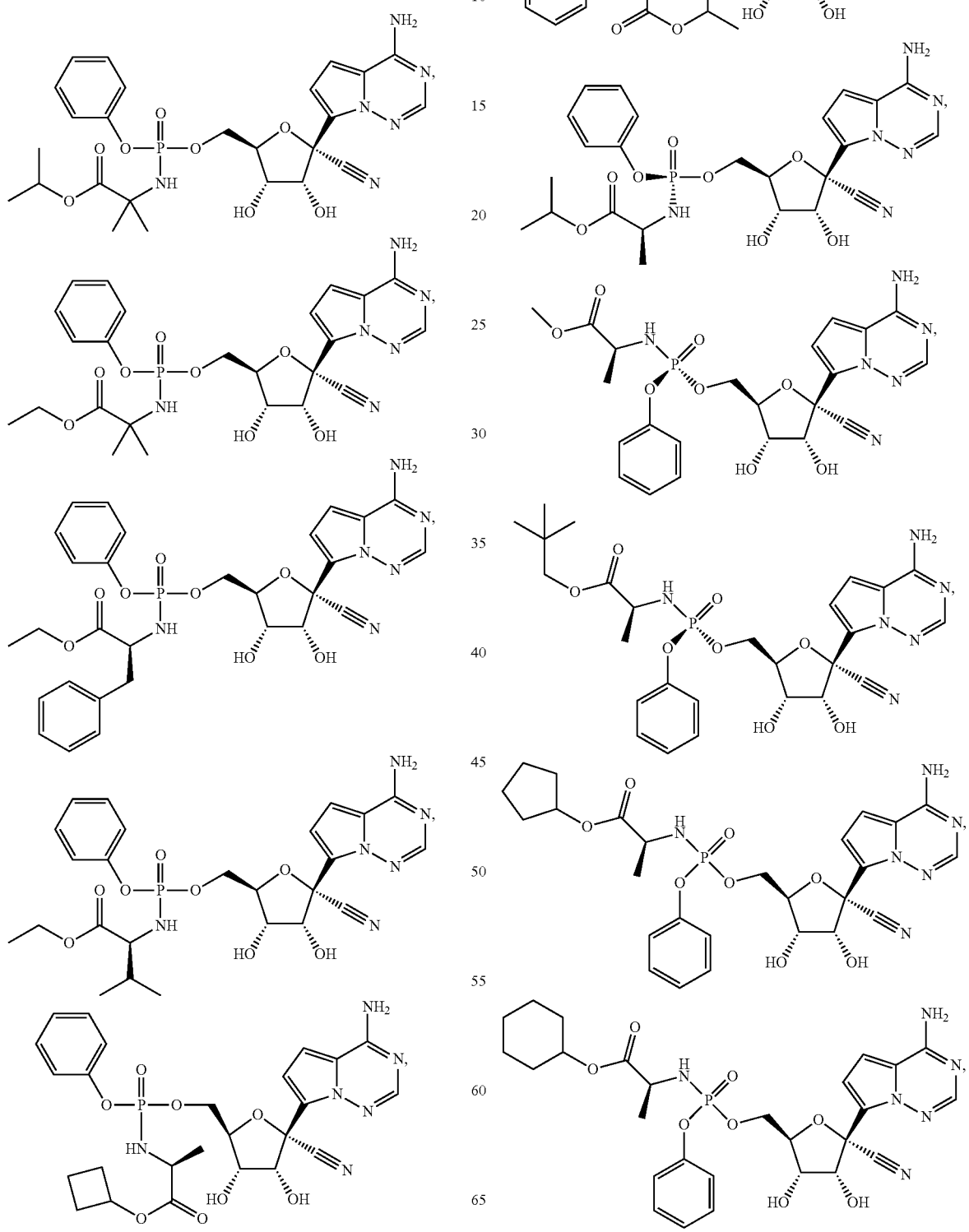

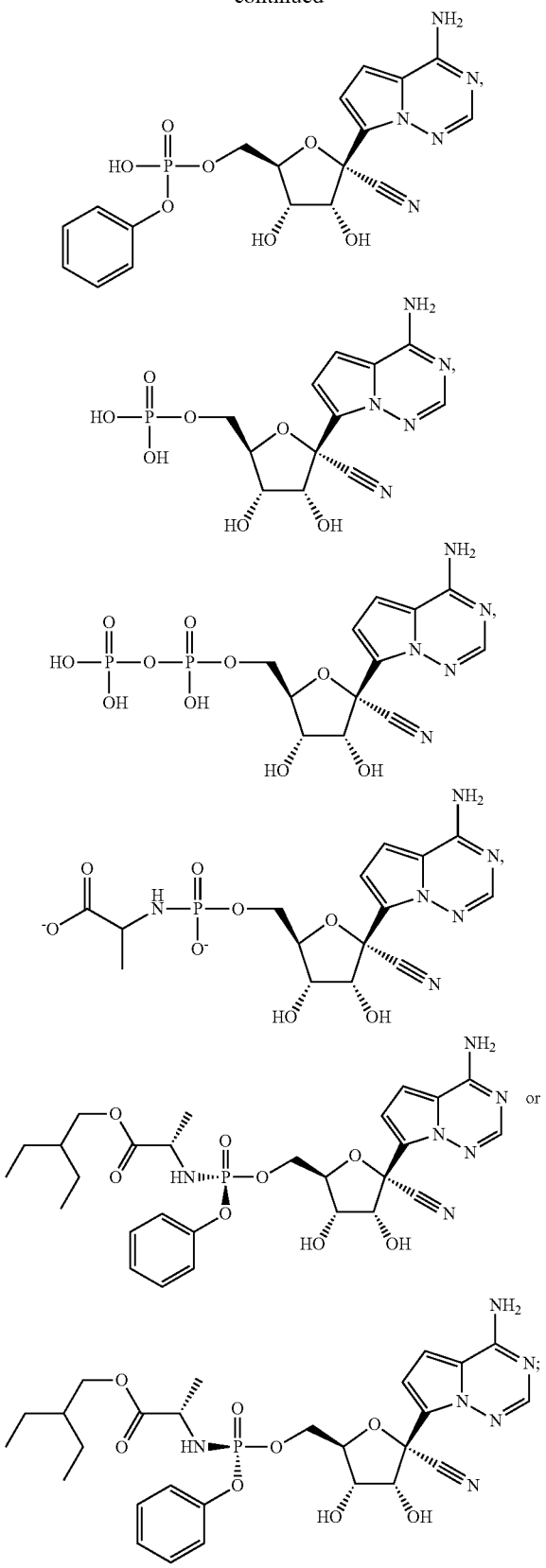

or a pharmaceutically acceptable salt, hydrate, or ester thereof.

DETAILED DESCRIPTION OF THE INVENTION

I. Definitions

Unless stated otherwise, the following terms and phrases as used herein are intended to have the following meanings:

When trade names are used herein, applicants intend to independently include the trade name product and the active pharmaceutical ingredient(s) of the trade name product.

As used herein, "a compound of the invention" or "a compound of Formula IV" means a compound of Formula IV or a pharmaceutically acceptable salt, thereof. Similarly, with respect to isolatable intermediates, the phrase "a compound of Formula (number)" means a compound of that formula and pharmaceutically acceptable salts, thereof "Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., C$_2$-C$_{20}$ alkynyl), 2 to 8 carbon atoms (i.e., C$_2$-C$_8$ alkyne,), or 2 to 6 carbon atoms (i.e., C$_2$-C$_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^a$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b_2$, —N$^+$R$^b_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b_2$, —S(=O)$_2$—, —S(=O)$_2$OH, —S(=O)$_2$R$^b$, —OS(=O)$_2$OR$^b$, —S(=O)$_2$NR$^b_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b_2$, —C(S)NR$^b_2$, —C(=NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula IV should be selected in order to provide a compound which is sufficiently stable to provide a pharmaceutically useful compound which can be formulated into an acceptably stable pharmaceutical composition. Compounds of Formula IV which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

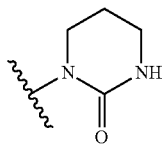 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

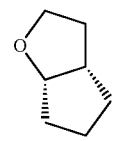

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or sp$^a$ carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloalkenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronaphthalene, and decaline.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula IV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula IV (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*)H$_2$(C*)H$_2$CH$_3$ or alkylene moiety —CH$_2$(C*)H$_2$(C*)H$_2$CH$_2$— the C* atoms would be considered to be the non-terminal carbon atoms.

Certain Q and $Q^1$ alternatives are nitrogen oxides such as $^+N(O)(R)$ or $^+N(O)(OR)$. These nitrogen oxides, as shown here attached to a carbon atom, can also be represented by charge separated groups such as

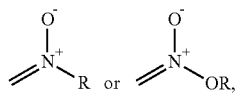

respectively, and are intended to be equivalent to the aforementioned representations for the purposes of describing this invention.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

In some embodiments of the compounds of Formula IV, one or more of $Z^1$ or $Z^2$ are independently a radical of a nitrogen-linked naturally occurring α-amino acid ester. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substituent R, particularly those in which R is optionally substituted $(C_1-C_8)$alkyl.

The term "purine" or "pyrimidine" base comprises, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioallyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-5-iodopyrimidine, $C^6$-iodo-pyrimidine, $C^5$—Br-vinyl pyrimidine, $C^6$—Br— vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. The purine and pyrimidine bases are linked to the ribose sugar, or analog thereof, through a nitrogen atom of the base. Functional oxygen and nitrogen groups on the base can be protected as necessary or desired. Suitable protecting groups are well known to those skilled in the art, and include trimethylsilyl, dimethylhexylsilyl, t-butyldim-ethylsilyl, and t-butyldiphenylsilyl, trityl, alkyl groups, and acyl groups such as acetyl and propionyl, methanesulfonyl, and p-toluenesulfonyl.

Unless otherwise specified, the carbon atoms of the compounds of Formula IV are intended to have a valence of four. In some chemical structure representations where carbon atoms do not have a sufficient number of variables attached to produce a valence of four, the remaining carbon substituents needed to provide a valence of four should be assumed to be hydrogen. For example,

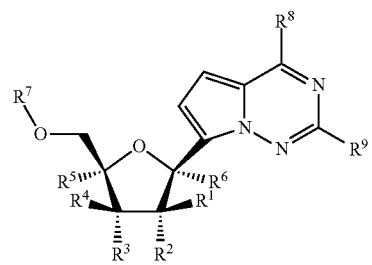

has the same meaning as

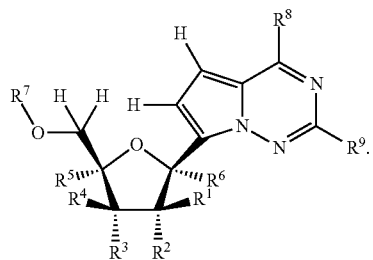

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. See also *Protective Groups in Organic Chemistry*, Peter G. M. Wuts and Theodora W. Greene, 4th Ed., 2006. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive. "Hydroxy protecting groups" refers to those protecting groups useful for protecting hydroxy groups (—OH).

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula IV may have a chiral phosphorus atom when $R^7$ is

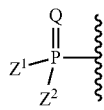

and $Z^1$ and $Z^2$ are different. When at least one of either $Z^1$ or $Z^2$ also has a chiral center, for example with $Z^1$ or $Z^2$ is a nitrogen-linked, chiral, naturally occurring α-amino acid ester, then the compound of Formula IV will exists as diastereomers because there are two centers of chirality in the molecule. All such diastereomers and their uses described herein are encompassed by the instant invention. Mixtures of diastereomers may be separate under high resolution analytical procedures such as electrophoresis, crystallization and/or chromatography. Diastereomers may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

The modifier "about" used in connection with a quantity is inclusive of the stated value and has the meaning dictated by the context (e.g., includes the degree of error associated with measurement of the particular quantity).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "therapeutically effective amount", as used herein, is the amount of compound of Formula IV present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula IV, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

The term "normal saline" means a water solution containing 0.9% (w/v) NaCl.

The term "hypertonic saline" means a water solution containing greater than 0.9% (w/v) NaCl. For example, 3% hypertonic saline would contain 3% (w/v) NaCl.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Coupling agent" refers to an agent capable of coupling two disparate compounds. Coupling agents can be catalytic or stoichiometric. For example, the coupling agents can be a lithium based coupling agent or a magnesium based coupling agent such as a Grignard reagent. Exemplary coupling agents include, but are not limited to, n-BuLi, $MgCl_2$, iPrMgCl, tBuMgCl, PhMgCl or combinations thereof.

"Silane" refers to a silicon containing group having the formula $SiR_4$, where each R group can be alkyl, alkenyl, cycloalkyl, phenyl, or other silicon containing groups. When the silane is linked to another compound, the silane is referred to as a "silyl" and has the formula $—SiR_3$.

"Halo-silane" refers to a silane having at least one halogen group linked to the silicon atom. Representative halo-silanes have the formula $Halo-SiR_3$, where each R group can be alkyl, alkenyl, cycloalkyl, phenyl, or other silicon containing groups. Specific halo-silanes include $Cl—Si(CH_3)_3$, and $Cl—Si(CH_3)_2CH_2CH_2Si(CH_3)_2—Cl$.

"Non-nucleophilic base" refers to an electron donor, a Lewis base, such as nitrogen bases including triethylamine, diisopropylethyl amine, N,N-diethylaniline, pyridine, 2,6-lutidine, 2,4,6-collidine, 4-dimethylaminopyridine, and quinuclidine.

"Leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, mesylate, tosylate, triflate, 4-nitrobenzenesulfonate, 4-chlorobenzenesulfonate, 4-nitrophenoxy, pentafluorophenoxy, etc. One of skill in the art will recognize other leaving groups useful in the present invention.

"Deprotection agent" refers to any agent capable of removing a protecting group. The deprotection agent will depend on the type of protecting group used. Representative deprotection agents are known in the art and can be found in *Protective Groups in Organic Chemistry*, Peter G. M. Wuts and Theodora W. Greene, 4th Ed., 2006.

II. Compounds of the Present Invention

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

Provided, is a method for treating a Filoviridae infection in a human in need thereof comprising administering a therapeutically effective amount of a compound of Formula I:

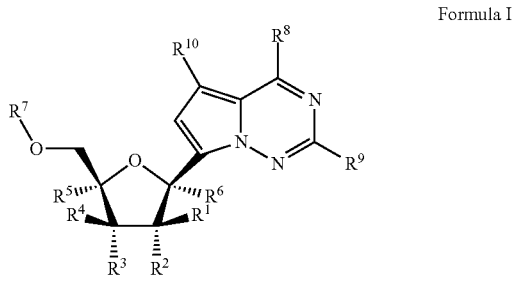

Formula I or a pharmaceutically acceptable salt, hydrate or ester, thereof;
wherein:
each $R^1$ is H or halogen;
each $R^2$, $R^3$, $R^4$ or $R^5$ is independently H, $OR^a$, $N(R^a)_2$, $N_3$, CN, $NO_2$, $S(O)_nR^a$, halogen, $(C_1-C_8)$alkyl, $(C_4-C_8)$carbocyclylalkyl, $(C_1-C_8)$ d) a group of the formula:

$$Z^1-\overset{\overset{Q}{\|}}{\underset{Z^2}{P}}-$$

wherein
Q is O, S, NR, ⁺N(O)(R), N(OR), ⁺N(O)(OR), or N—NR₂;
$Z^1$ and $Z^2$, when taken together, are -$Q^1(C(R^y)_2)_3Q^1$-;
wherein
  each $Q^1$ is independently O, S, or NR; and
  each $R^y$ is independently H, F, Cl, Br, I, OH, R, —C(=Q²)R, —C(=Q²)OR, —C(=Q²)N(R)₂, —N(R)₂, —⁺N(R)₃, —SR, —S(O)R, —S(O)₂R, —S(O)(OR), —S(O)₂(OR), —OC(=Q¹)R, —OC(=Q²)OR, —OC(=Q²)(N(R)₂), —SC(=Q²)R, —SC(=Q²)OR, —SC(=Q²)(N(R)₂), —N(R)C(=Q²)R, —N(R)C(=Q²)OR, —N(R)C(=Q²)N(R)₂, —SO₂NR₂, —CN, —N₃, —NO₂, —OR, or $Z^3$; or when taken together, two $R^y$ on the same carbon atom form a carbocyclic ring of 3 to 7 carbon atoms;
  each $Q^2$ is independently, O, S, NR, ⁺N(O)(R), N(OR), ⁺N(O)(OR), or N—NR₂; or
$Z^1$ and $Z^2$ are each, independently, a group of the Formula Ia:

Formula Ia $$\left[ R^x - \left( Q^3 - \overset{\overset{Q^2}{\|}}{\underset{\underset{R^x}{|}}{\underset{Q^3}{|}}} \right) Q^3 \right]_{M2}$$

wherein:
  each $Q^3$ is independently a bond, O, CR₂, NR, ⁺N(O)(R), N(OR), ⁺N(O)(OR), N—NR₂, S, S—S, S(O), or S(O)₂;
  M2 is 0, 1 or 2;
  each $R^x$ is independently $R^y$ or the formula:

$$\xi\left[ \overset{Q^2}{\underset{Q^3}{\|}} \right]_{M1a} \left[ \overset{R^y}{\underset{R^y}{|}} \right]_{M12c} \left( Q^3 \right)_{M1c} \left[ \overset{Q^2}{\underset{Q^3}{\|}} \right]_{M1d} R^y$$

wherein:
  each M1a, M1c, and M1d is independently 0 or 1;
  M12c is 0, 1, 2, 3, 4, 5, 6, 7, 8, 9, 10, 11 or 12;
  $Z^3$ is $Z^4$ or $Z^5$;
  $Z^4$ is R, —C(Q²)R$^y$, —C(Q²)Z⁵, —SO₂R$^y$, or —SO₂Z⁵; and
  $Z^5$ is a carbocycle or a heterocycle wherein $Z^5$ is independently substituted with 0 to 3 R$^y$ groups;
  each $R^8$ is halogen, NR¹¹R¹², N(R¹¹)OR¹¹, NR¹¹NR¹¹R¹², N₃, NO, NO₂, CHO, CN, —CH(=NR¹¹), —CH=NNHR¹¹, —CH=N(OR¹¹), —CH(OR¹¹)₂, —C(=O)NR¹¹R¹², —C(=S)NR¹¹R¹²,
  —C(=O)OR¹¹, (C₁-C₈)alkyl, (C₂-C₈)alkenyl, (C₂-C₈)alkynyl, (C₄-C₈)carbocyclylalkyl, optionally substituted aryl, optionally substituted heteroaryl, —C(=O)(C₁-C₈)alkyl, —S(O)ₙ(C₁-C₈)alkyl, aryl(C₁-C₈)alkyl, OR¹¹ or SR¹¹;
  each $R^9$ or $R^{16}$ is independently H, halogen, NR¹¹R¹², N(R¹¹)OR¹¹, NR¹¹NR¹¹R¹², N₃, NO, NO₂, CHO, CN, —CH(=NR¹¹), —CH=NHNR¹¹, —CH=N(OR¹¹), —CH(OR¹¹)₂, —C(=O)NR¹¹R¹², —C(=S)NR¹¹R¹², —C(=O)OR¹¹, R¹¹, OR¹¹ or SR¹¹; and
  wherein each (C₁-C₈)alkyl, (C₂-C₈)alkenyl, (C₂-C₈)alkynyl or aryl(C₁-C₈)alkyl of each R², R³, R⁵, or R⁶ is, independently, optionally substituted with one or more halo, hydroxy, CN, N₃, N(R$^a$)₂ or OR$^a$; and wherein one or more of the non-terminal carbon atoms of each said (C₁-C₈)alkyl may be optionally replaced with —O—, —S— or —NR$^a$—.

In another embodiment, provided is a compound of Formula IV:

Formula IV or a pharmaceutically acceptable salt, hydrate or ester, thereof;
wherein R⁷ is as defined above for Formula I.

Provided, is a method for treating a Filoviridae infection in a human in need thereof comprising administering a therapeutically effective amount of a compound of Formula IV:

Formula IV or a pharmaceutically acceptable salt or ester, thereof;
wherein:
R⁷ is selected from the group of
a) H, —C(=O)R¹¹, —C(=O)OR¹¹, —C(=O)NR¹¹R¹², —C(=O)SR¹¹, —S(O)R¹¹, —S(O)₂R¹¹, —S(O)(OR¹¹), —S(O)₂(OR¹¹), or —SO₂NR¹¹R¹²
wherein
each R¹¹ or R¹² is independently H, (C₁-C₈)alkyl, (C₂-C₈)alkenyl, (C₂-C₈)alkynyl, (C₄-C₈)carbocyclylalkyl, optionally substituted aryl, optionally substituted heteroaryl, —C(=O)(C₁-C₈)alkyl, —S(O)ₙ(C₁-C₈)alkyl or aryl(C₁-C₈)alkyl; or R¹¹ and R¹² taken together with a nitrogen to which they are both attached form a 3 to 7 membered heterocyclic ring wherein any one carbon atom of said heterocyclic ring can optionally be replaced with —O—, —S— or —NR$^a$—;

each R$^a$ is independently H, (C$_1$-C$_8$)alkyl, (C$_2$-C$_8$)alkenyl, (C$_2$-C$_8$)alkynyl, aryl(C$_1$-C$_8$)alkyl, (C$_4$-C$_8$)carbocyclylalkyl, —C(=O)R, —C(=O)OR, —C(=O)NR$_2$, —C(=O)SR, —S(O)R, —S(O)$_2$R, —S(O)(OR), —S(O)$_2$(OR), or —SO$_2$NR$_2$;

wherein each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocyclyl, C$_2$-C$_{20}$ substituted heterocyclyl, arylalkyl or substituted arylalkyl; and wherein each (C$_1$-C$_8$)alkyl, (C$_2$-C$_8$)alkenyl, (C$_2$-C$_8$)alkynyl or aryl(C$_1$-C$_8$)alkyl of each R$^{11}$ or R$^{12}$ is, independently, optionally substituted with one or more halo, hydroxy, CN, N$_3$, N(R$^a$)$_2$ or OR$^a$; and wherein one or more of the non-terminal carbon atoms of each said (C$_1$-C$_8$)alkyl may be optionally replaced with —O—, —S— or —NR—, and b)

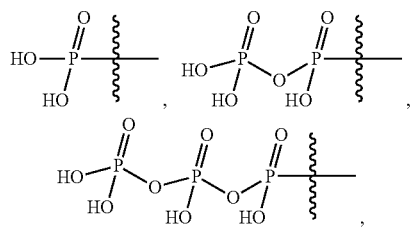

c) a group selected from:

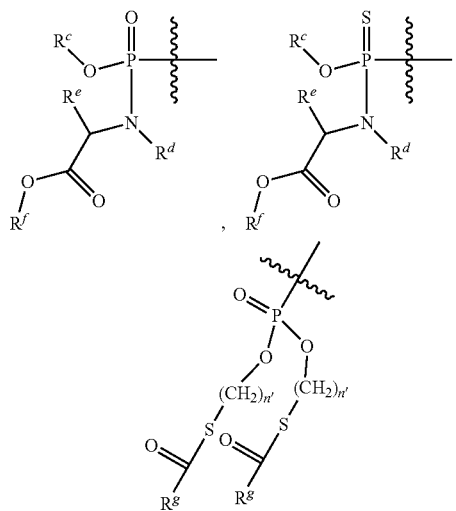

wherein:
R$^c$ is selected from phenyl, 1-naphthyl, 2-naphthyl,

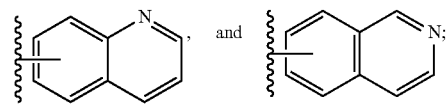

R$^d$ is H or CH$_3$;
R$^e$ is H or C$_1$-C$_6$ alkyl;
R$^f$ is selected from H, C$_1$-C$_8$ alkyl, benzyl, C$_3$-C$_6$ cycloalkyl, and —CH$_2$—C$_3$-C$_6$ cycloalkyl;
R$^g$ is selected from C$_1$-C$_8$ alkyl, —O—C$_1$-C$_8$ alkyl, benzyl, —O-benzyl, —CH$_2$—C$_3$-C$_6$ cycloalkyl, —O—CH$_2$—C$_3$-C$_6$ cycloalkyl, and CF$_3$; and
n' is selected from 1, 2, 3, and 4; and d) a group of the formula:

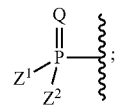

wherein
Q is O, S, NR, $^+$N(O)(R), N(OR), $^+$N(O)(OR), or N—NR$_2$;
Z$^1$ and Z$^2$, when taken together, are -Q$^1$(C(R$^y$)$_2$)$_3$Q$^1$-;
wherein
each Q$^1$ is independently O, S, or NR; and
each R$^y$ is independently H, F, Cl, Br, I, OH, R, —C(=Q$^2$)R, —C(=Q$^2$)OR, —C(=Q$^2$)N(R)$_2$, —N(R)$_2$, —$^+$N(R)$_3$, —SR, —S(O)R, —S(O)$_2$R, —S(O)(OR), —S(O)$_2$(OR), —OC(=Q$^1$)R, —OC(=Q$^2$)OR, —OC(=Q$^2$)(N(R)$_2$), —SC(=Q$^2$)R, —SC(=Q$^2$)OR, —SC(=Q$^2$)(N(R)$_2$), —N(R)C(=Q$^2$)R, —N(R)C(=Q$^2$)OR, —N(R)C(=Q$^2$)N(R)$_2$, —SO$_2$NR$_2$, —CN, —N$_3$, —NO$_2$, —OR, or Z$^3$; or when taken together, two R$^y$ on the same carbon atom form a carbocyclic ring of 3 to 7 carbon atoms;
each Q$^2$ is independently, O, S, NR, $^+$N(O)(R), N(OR), $^+$N(O)(OR), or N—NR$_2$; or
Z$^1$ and Z$^2$ are each, independently, a group of the Formula Ia:

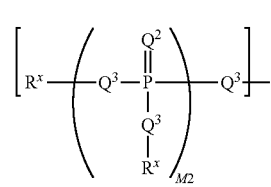

Formula Ia wherein:
each Q$^3$ is independently a bond, O, CR$_2$, NR, $^+$N(O)(R), N(OR), $^+$N(O)(OR), N—NR$_2$, S, S—S, S(O), or S(O)$_2$;
M2 is 0, 1 or 2;
each R$^x$ is independently R$^y$ or the formula:

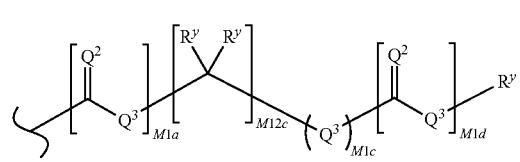

wherein:
each M1a, M1c, and M1d is independently 0 or 1;
M12c is 0, 1, 2, 3, 4, 5, 6, 7, 8, 9, 10, 11 or 12;

$Z^3$ is $Z^4$ or $Z^5$;

$Z^4$ is R, —$C(Q^2)R^y$, —$C(Q^2)Z^5$, —$SO_2R^y$, or —$SO_2Z^5$; and $Z^5$ is a carbocycle or a heterocycle wherein $Z^5$ is independently substituted with 0 to 3 $R^y$ groups.

Provided, is a method for treating a Filoviridae infection in a human in need thereof comprising administering a therapeutically effective amount of a compound of Formula IV:

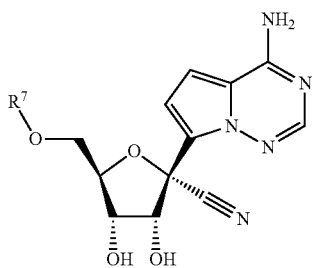

Formula IV or a pharmaceutically acceptable salt, hydrate or ester, thereof;

wherein, $R^7$ is selected from the group consisting of a) H, —C(=O)$R^{11}$, —C(=O)$OR^{11}$, —C(=O)$NR^{11}R^{12}$, —C(=O)$SR^{11}$, —S(O)$R^{11}$, —$S(O)_2R^{11}$, —$S(O)_2(OR^{11})$, or —$SO_2NR^{11}R^{12}$;

b)

,

,

;

c) a group selected from:

, and wherein:

$R^c$ is selected from the group of phenyl, 1-naphthyl, 2-naphthyl, and

;

$R^d$ is selected from the group of H or $CH_3$;

$R^{e1}$ and $R^{e2}$ are each independently selected from the group of H, $(C_1\text{-}C_6)$alkyl or benzyl;

$R^f$ is selected from the group of from H, $(C_1\text{-}C_8)$alkyl, benzyl, $(C_3\text{-}C_6)$cycloalkyl, and —$CH_2$—$(C_3\text{-}C_6)$cycloalkyl;

$R^g$ is selected from selected from the group of $(C_1\text{-}C_8)$alkyl, —O—$(C_1\text{-}C_8)$alkyl, benzyl, —O-benzyl, —$CH_2$—$(C_3\text{-}C_6)$cycloalkyl, —O—$CH_2$—$(C_3\text{-}C_6)$cycloalkyl, and $CF_3$; and n' is an integer selected from the group of 1, 2, 3, and 4; and d) a group of the formula:

;

wherein:

Q is selected from the group of O, S, NR, $^+N(O)(R)$, N(OR), $^+N(O)(OR)$, or N—$NR_2$;

$Z^1$ and $Z^2$, when taken together, are $-Q^1(C(R^y)_2)_3Q^1$-;

wherein each $Q^1$ is independently selected from the group of O, S, or NR; and each $R^y$ is independently selected from the group of H, F, Cl, Br, I, OH, R, —$C(=Q^2)R$, —$C(=Q^2)OR$, —$C(=Q^2)N(R)_2$, —$N(R)_2$, —$^+N(R)_3$, —SR, —S(O)R, —$S(O)_2R$, —S(O)(OR), —$S(O)_2(OR)$, —$OC(=Q^1)R$, —$OC(=Q^2)OR$, —$OC(=Q^2)(N(R)_2)$, —$SC(=Q^2)R$, —$SC(=Q^2)OR$, —$SC(=Q^2)(N(R)_2)$, —$N(R)C(=Q^2)R$, —$N(R)C(=Q^2)OR$, —$N(R)C(=Q^2)N(R)_2$, —$SO_2NR_2$, —CN, —$N_3$, —$NO_2$, —OR, or $Z^3$; or when taken together, two $R^y$ on the same carbon atom form a carbocyclic ring of 3 to 7 carbon atoms;

each $Q^2$ is independently, O, S, NR, $^+N(O)(R)$, N(OR), $^+N(O)(OR)$, or N—$NR_2$; or $Z^1$ and $Z^2$ are each, independently, a group of the Formula Ia:

Formula Ia wherein:

each $Q^3$ is independently selected from the group of a bond, O, $CR_2$, NR, $^+N(O)(R)$, N(OR), $^+N(O)(OR)$, N—$NR_2$, S, S—S, S(O), or $S(O)_2$;

M2 is an integer selected from the group of 0, 1 or 2;

each $R^x$ is independently $R^y$ or the formula:

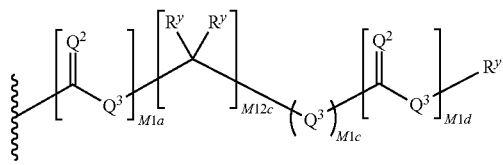

wherein:
each M1a, M1c, and M1d is an integer independently selected from the group of 0 or 1;
M12c is an integer selected from the group of 0, 1, 2, 3, 4, 5, 6, 7, 8, 9, 10, 11 or 12;
$Z^3$ is $Z^4$ or $Z^5$;
$Z^4$ is R, —C(Q²)R$^y$, —C(Q²)Z$^5$, —SO₂R$^y$, or —SO₂Z$^5$; and
$Z^5$ is a carbocycle or a heterocycle wherein $Z^5$ is independently substituted with 0 to 3 $R^y$ groups;

each $R^{11}$ or $R^{12}$ is independently H, (C₁-C₈)alkyl, (C₂-C₈)alkenyl, (C₂-C₈)alkynyl, (C₄-C₈)carbocyclylalkyl, (C₆-C₂₀)optionally substituted aryl, optionally substituted heteroaryl, —C(=O)(C₁-C₈)alkyl, —S(O)₆(C₁-C₈)alkyl or (C₆-C₂₀)aryl(C₁-C₈)alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —NR$^a$—;

each $R^a$ is independently selected from the group of H, (C₁-C₈)alkyl, (C₂-C₈)alkenyl, (C₂-C₈)alkynyl, (C₆-C₂₀)aryl(C₁-C₈)alkyl, (C₄-C₈)carbocyclylalkyl, —C(=O)R, —C(=O)OR, —C(=O)NR₂, —C(=O)SR, —S(O)R, —S(O)₂R, —S(O)(OR), —S(O)₂(OR), or —SO₂NR₂; wherein each R is independently selected from the group of H, (C₁-C₈) alkyl, (C₁-C₈) substituted alkyl, (C₂-C₈)alkenyl, (C₂-C₈) substituted alkenyl, (C₂-C₈) alkynyl, (C₂-C₈) substituted alkynyl, (C₆-C₂₀)aryl, (C₆-C₂₀)substituted aryl, (C₂-C₂₀)heterocyclyl, (C₂-C₂₀)substituted heterocyclyl, (C₆-C₂₀)aryl(C₁-C₈)alkyl or substituted (C₆-C₂₀)aryl(C₁-C₈)alkyl;

each n is an integer independently selected from the group of 0, 1, or 2; and wherein each (C₁-C₈)alkyl, (C₂-C₈)alkenyl, (C₂-C₈)alkynyl or (C₆-C₂₀)aryl(C₁-C₈)alkyl of each $R^{11}$ or $R^{12}$ is, independently, optionally substituted with one or more substituents selected from the group of halo, hydroxy, CN, N₃, N(R$^a$)₂ or OR$^a$; and wherein one or more of the non-terminal carbon atoms of each said (C₁-C₈)alkyl may be optionally replaced with —O—, —S— or —NR$^a$—.

In another embodiment of a compound of Formula IV, $R^7$ can be H. In another embodiment of a compound of Formula IV, $R^7$ is selected from the group of a), b), or c) as defined for Formula IV.

In some embodiments, $R^{e1}$ and $R^{e2}$ can each independently be selected from the group of H, C₁-C₆ alkyl or benzyl. In some embodiments, $R^{e1}$ can be H, C₁-C₆ alkyl or benzyl, and $R^{e2}$ can be H or C₁-C₆ alkyl. In some embodiments, $R^{e1}$ and $R^{e2}$ can each independently be H or C₁-C₆ alkyl. In some embodiments, $R^{e1}$ and $R^{e2}$ can each independently be H or benzyl. In some embodiments, $R^{e1}$ can be H, methyl or benzyl, and $R^{e2}$ can be H or methyl. In some embodiments, $R^{e1}$ can be H or methyl, and $R^{e2}$ can be H or methyl. In some embodiments, $R^{e1}$ can be methyl, and $R^{e2}$ can be H or methyl. In some embodiments, $R^{e1}$ can be H or benzyl, and $R^{e2}$ can be H or methyl.

In another embodiment of a compound of Formula IV, $R^7$ is

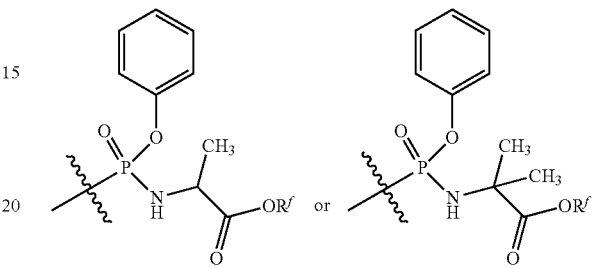

wherein $R^f$ is selected from the group of H, C₁-C₈ alkyl, benzyl, C₃-C₆ cycloalkyl, and —CH₂—C₃-C₆ cycloalkyl. In another embodiment of a compound of Formula IV, $R^f$ is C₁-C₈ alkyl.

In another embodiment of a compound of Formula IV, $R^7$ is

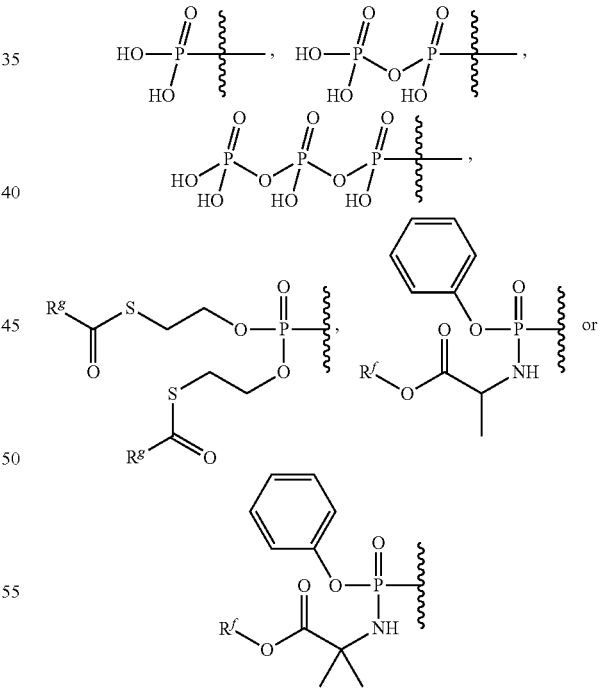

wherein
$R^f$ is selected from the group of H, C₁-C₈ alkyl, benzyl, C₃-C₆ cycloalkyl, and —CH₂—C₃-C₆ cycloalkyl; and
$R^g$ is selected from the group of C₁-C₈ alkyl, —O—C₁-C₈ alkyl, benzyl, —O-benzyl, —CH₂—C₃-C₆ cycloalkyl, —O—CH₂—C₃-C₆ cycloalkyl, and CF₃.

In another embodiment of a compound of Formula IV, $R^7$ is

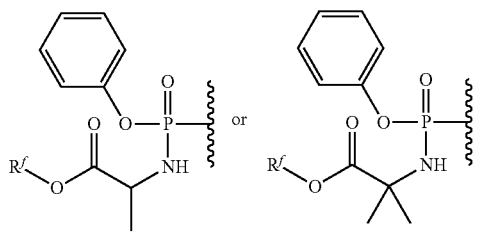

wherein $R^f$ is selected from the group of H, $C_1$-$C_8$ alkyl, benzyl, $C_3$-$C_6$ cycloalkyl, and —$CH_2$—$C_3$-$C_6$ cycloalkyl. In another embodiment of a compound of Formula IV, $R^f$ is $C_1$-$C_8$ alkyl. In another embodiment of a compound of Formula IV, $R^f$ is $C_1$-$C_6$ alkyl.

In another embodiment of a compound of Formula IV, $R^7$ is:

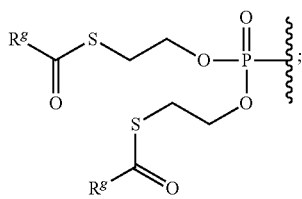

wherein $R^g$ is selected from the group of $C_1$-$C_8$ alkyl, —O—$C_1$-$C_8$ alkyl, benzyl, —O-benzyl, —$CH_2$—$C_3$-$C_6$ cycloalkyl, —O—$CH_2$—$C_3$-$C_6$ cycloalkyl, and $CF_3$. In another embodiment of a compound of Formula IV, $R^f$ is $C_1$-$C_8$ alkyl. In another embodiment of a compound of Formula IV, $R^f$ is $C_1$-$C_6$ alkyl.

In another embodiment of a compound of Formula IV, $R^7$ is selected from the group of:

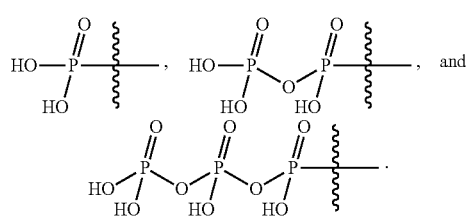

In another embodiment of a compound of Formula IV, $R^7$ is

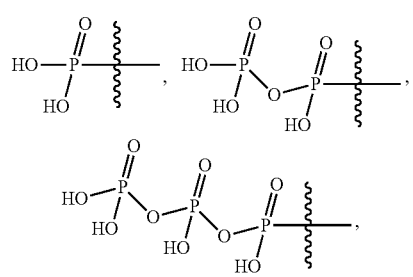

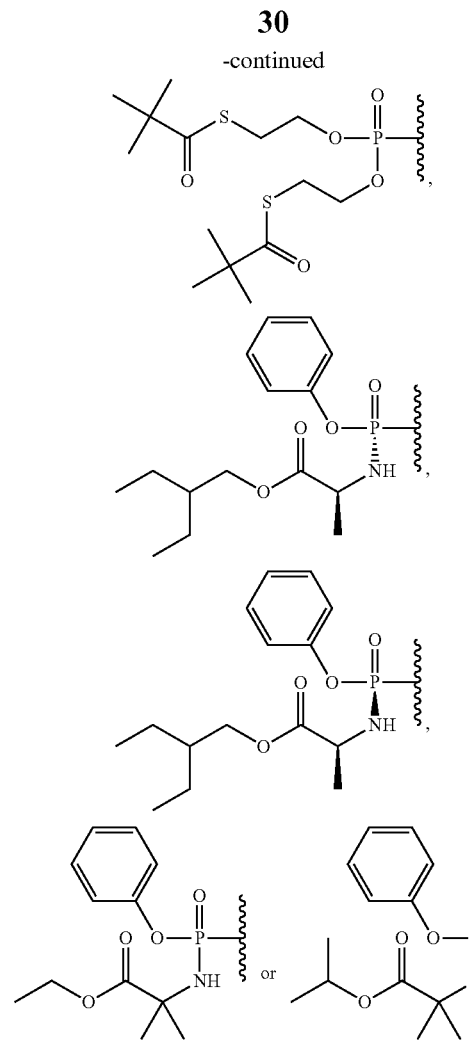

In another embodiment, provided is a compound of Formula IV that is:

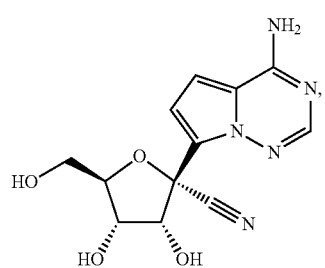

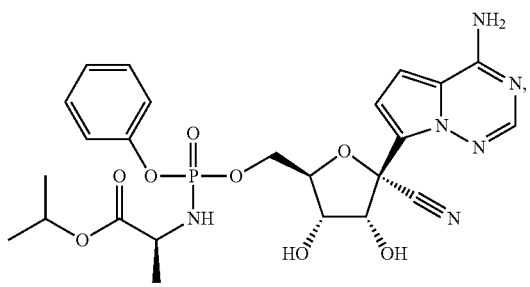

-continued
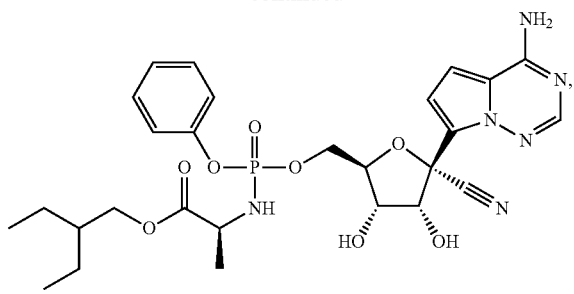
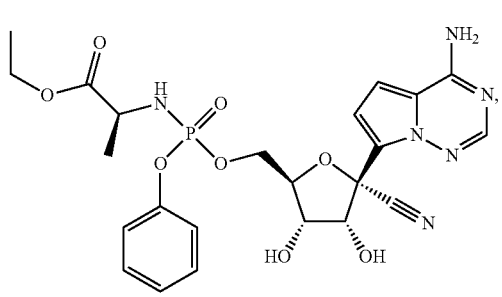
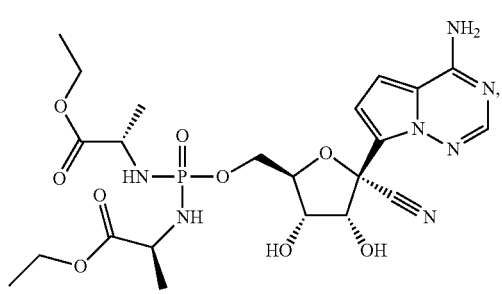
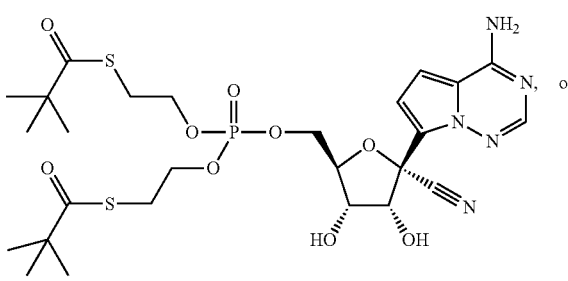
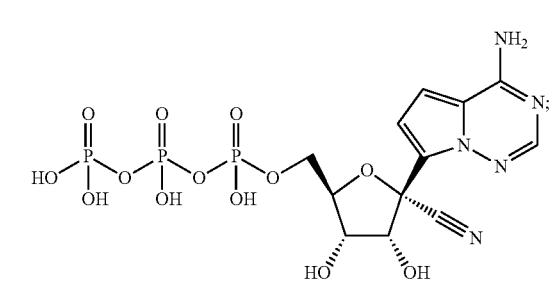 [SMILES: N#C[C@@]1(c2ccc3c(N)ncnn23)O[C@H](COP(=O)(O)OP(=O)(O)OP(=O)(O)O)[C@@H](O)[C@H]1O]
or a pharmaceutically acceptable salt or ester thereof
In another embodiments, provided is a compound of Formula IV that is:
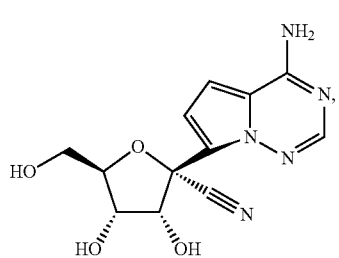
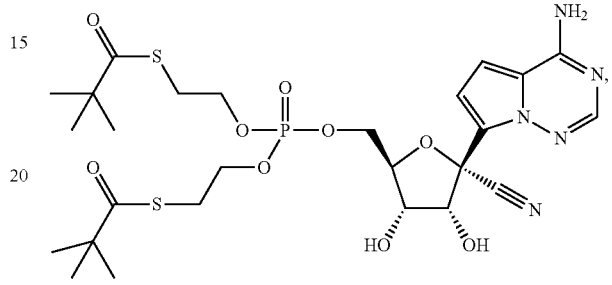
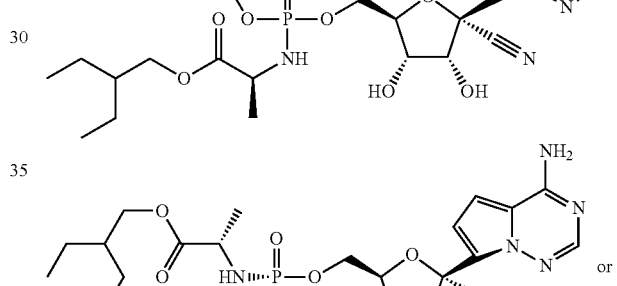
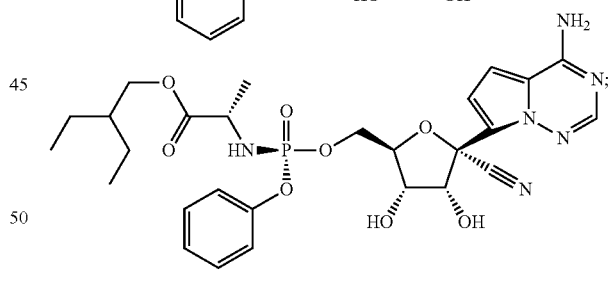
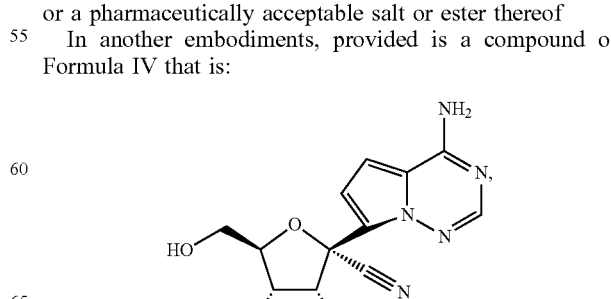
or a pharmaceutically acceptable salt or ester thereof
In another embodiments, provided is a compound of Formula IV that is:
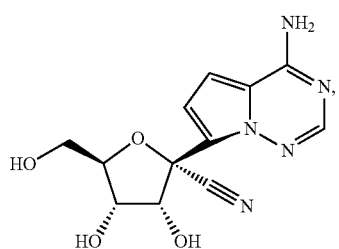

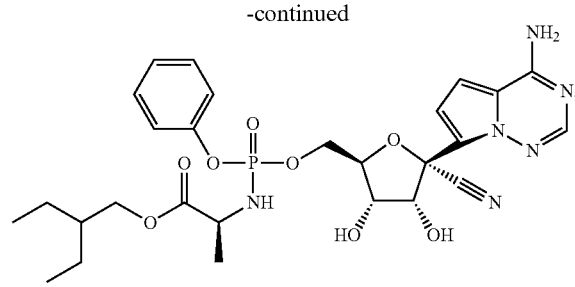
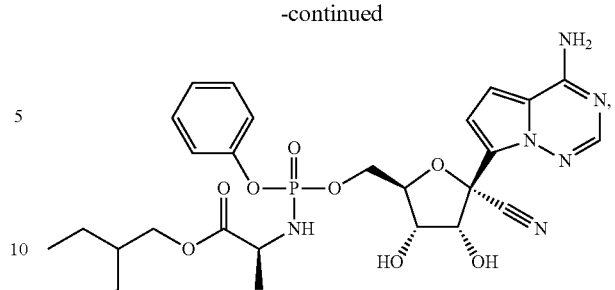
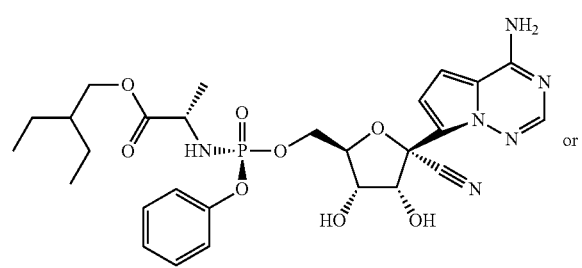
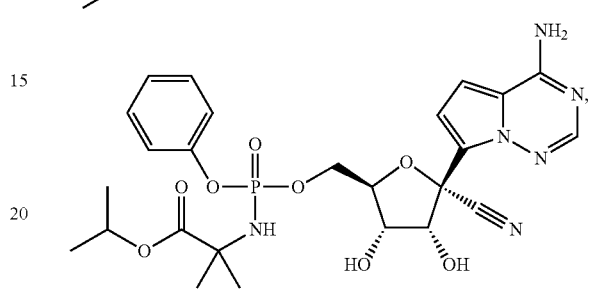
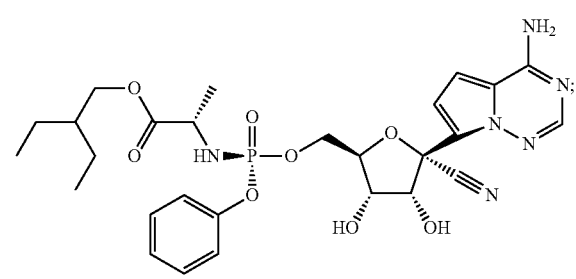
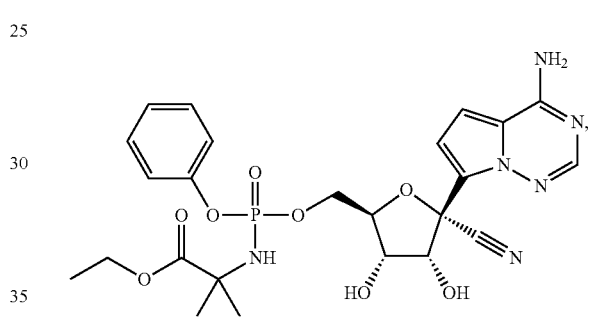
or a pharmaceutically acceptable salt, hydrate, or ester thereof
In another embodiment, provided is a compound of Formula IV that is
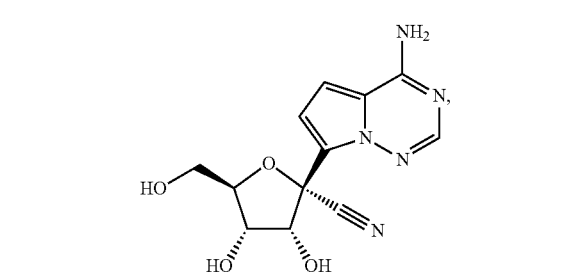
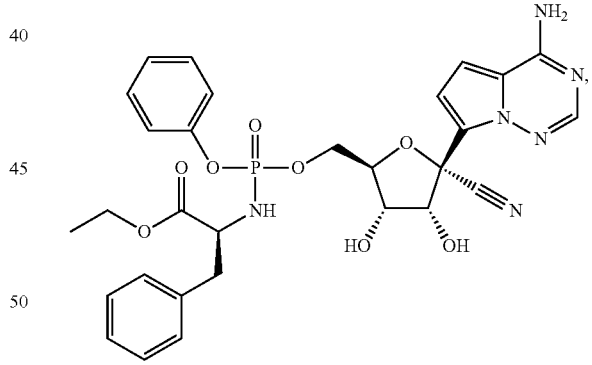
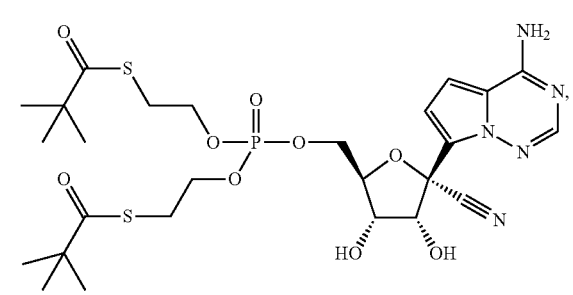
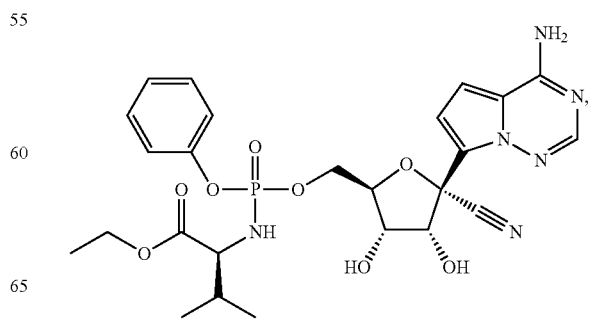

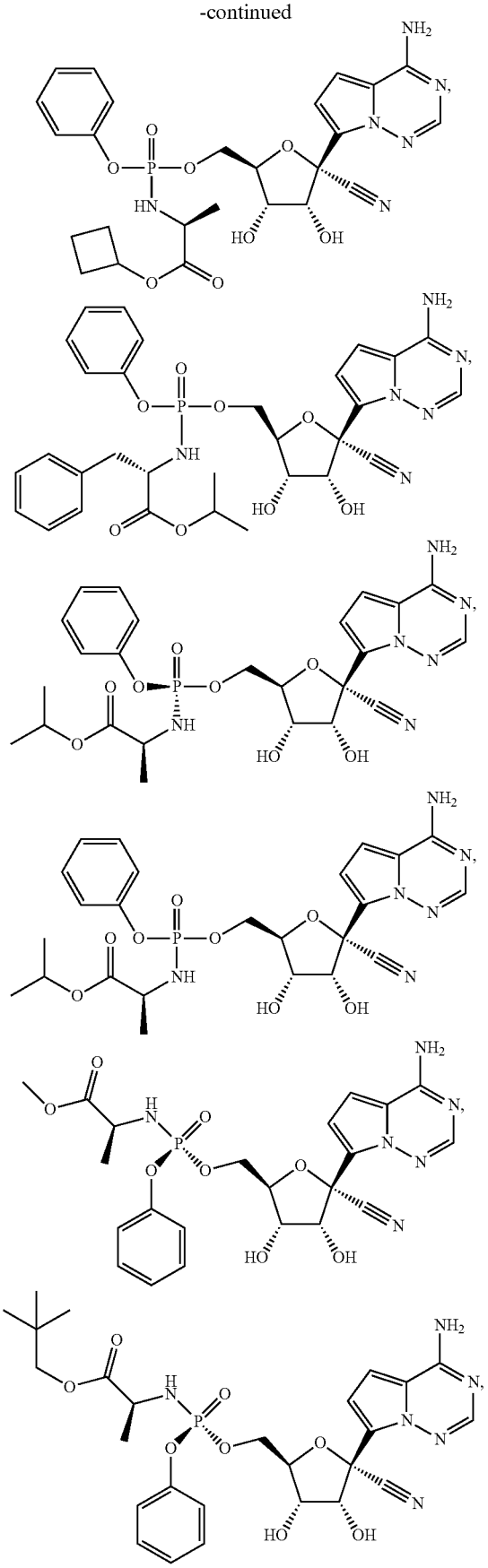
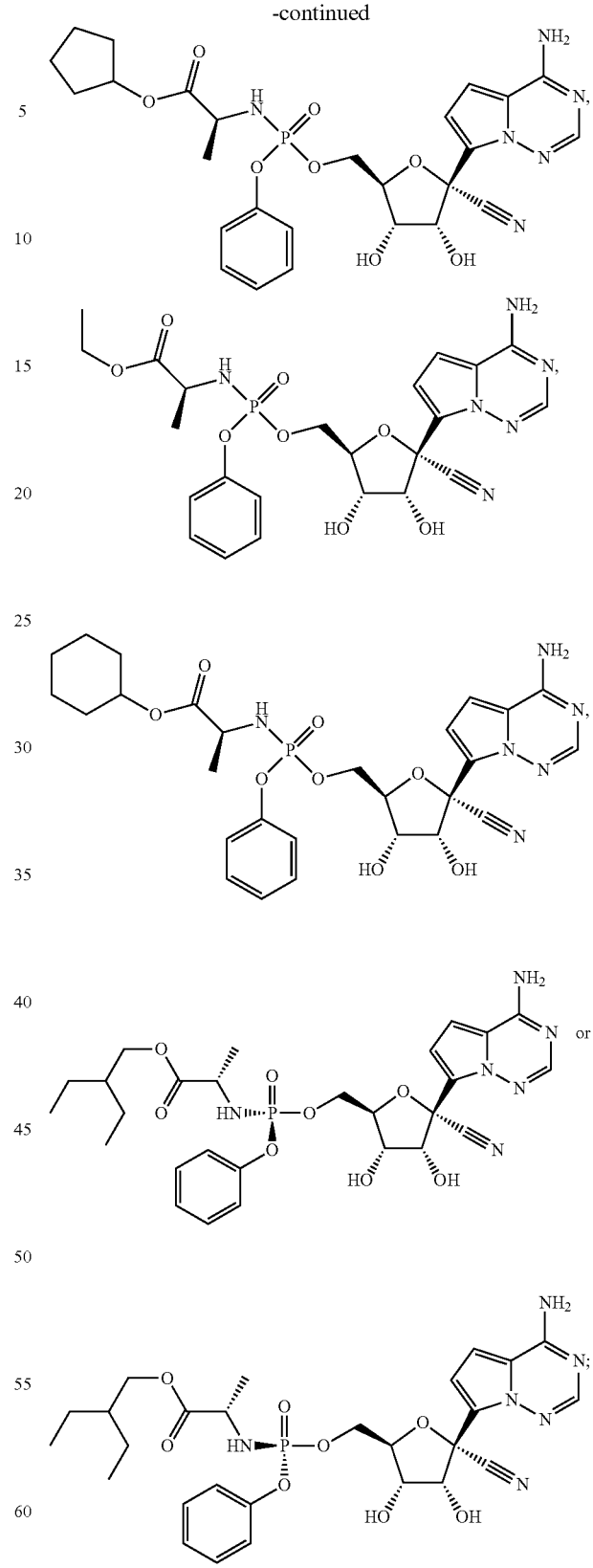
or a pharmaceutically acceptable salt or ester thereof
In another embodiment, the present invention provides a compound that is

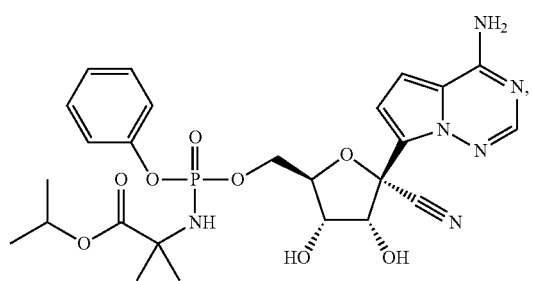
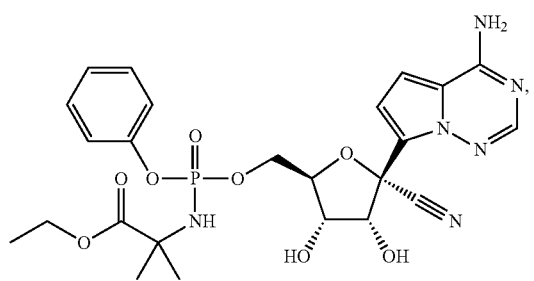
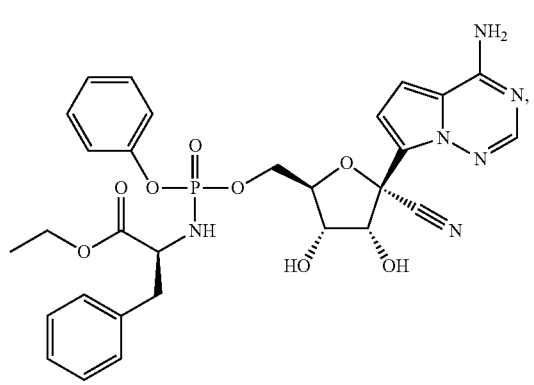
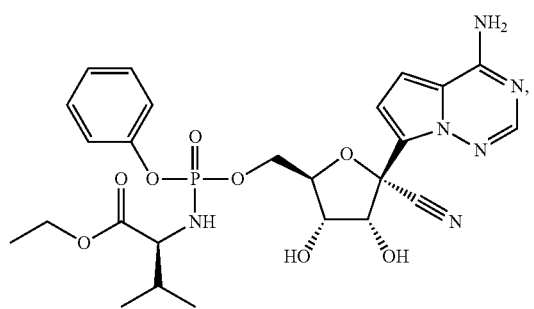
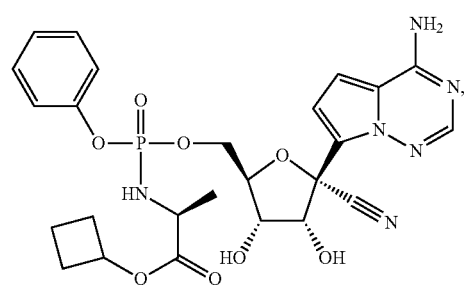
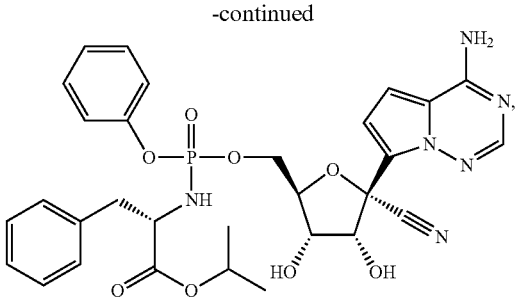
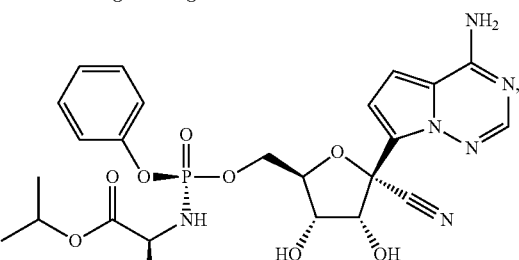
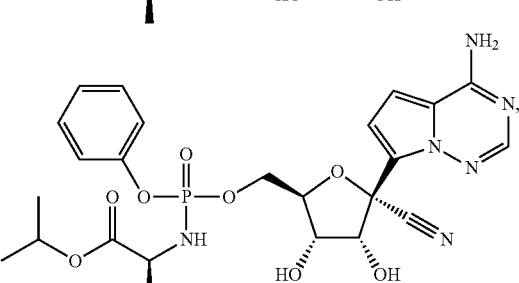
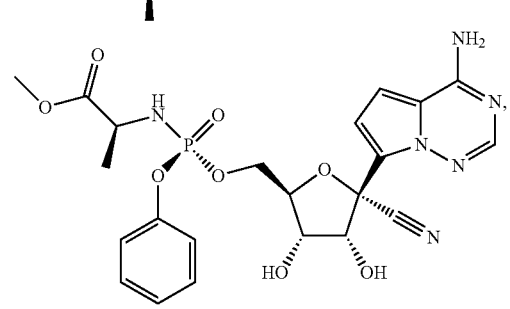
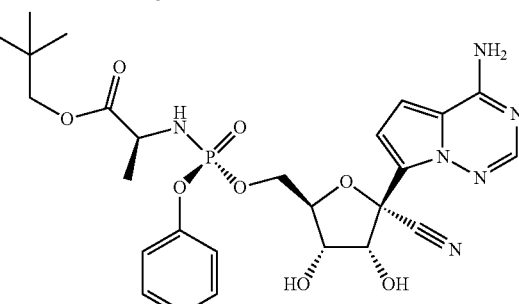
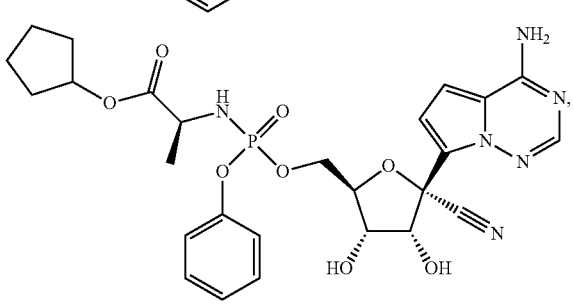

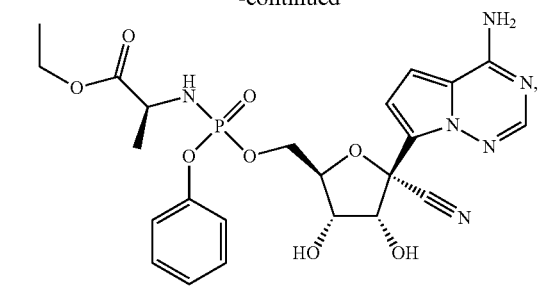
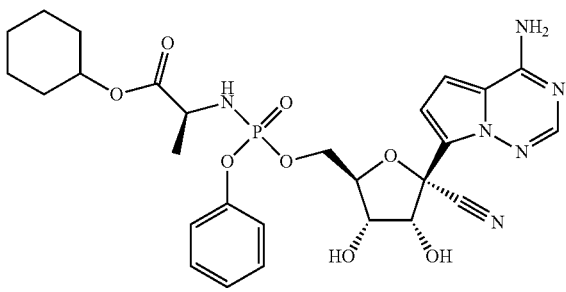
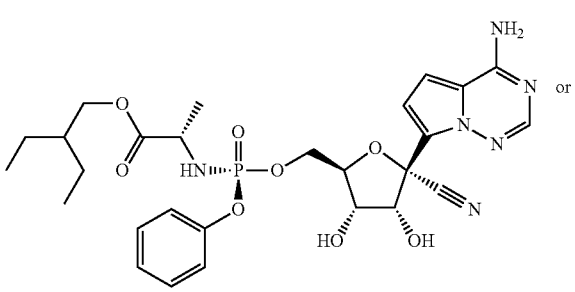
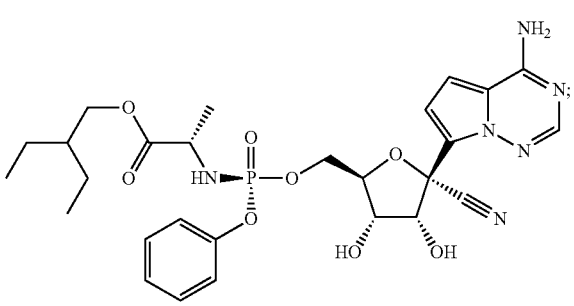
or a pharmaceutically acceptable salt or ester thereof
In another embodiment, the present invention provides a compound that is
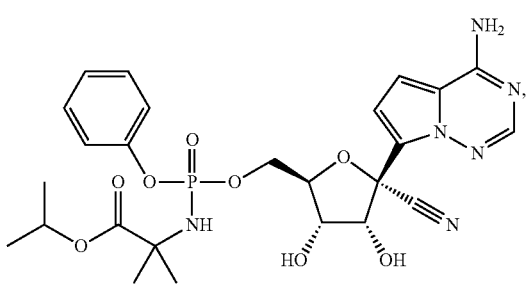
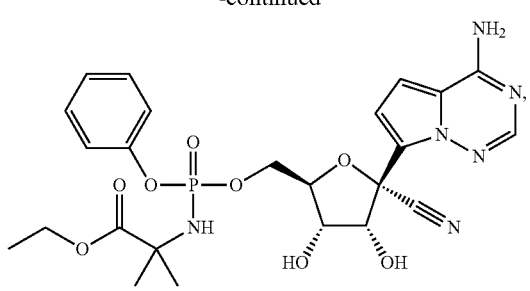
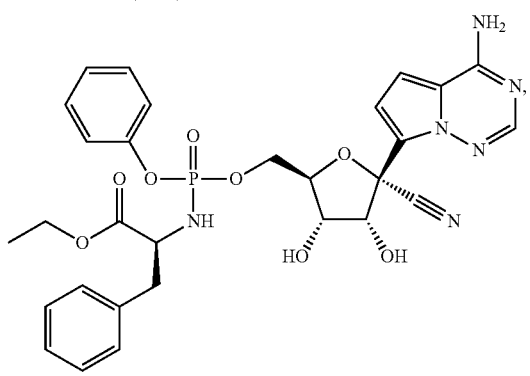
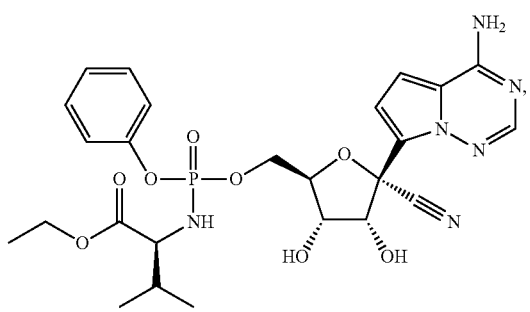
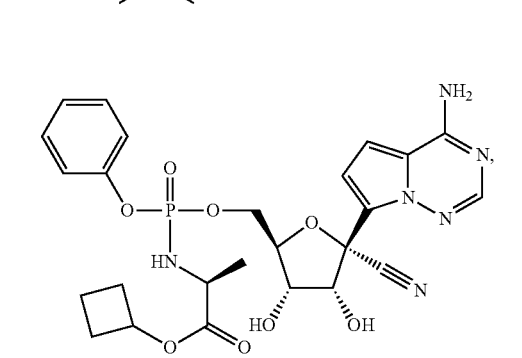
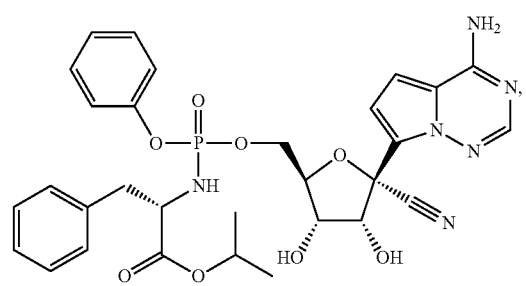

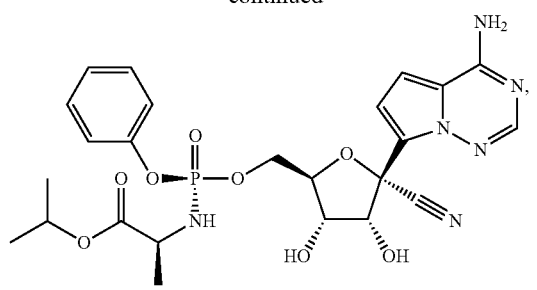
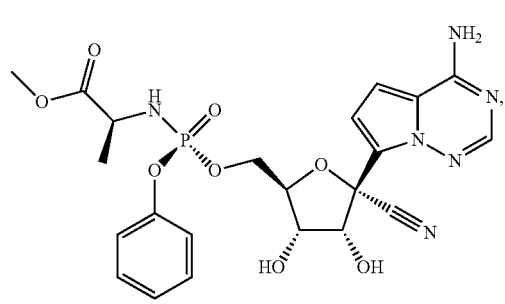
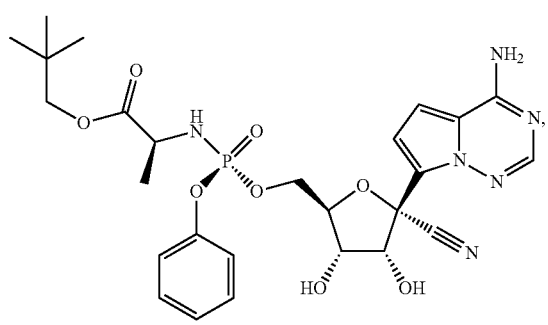
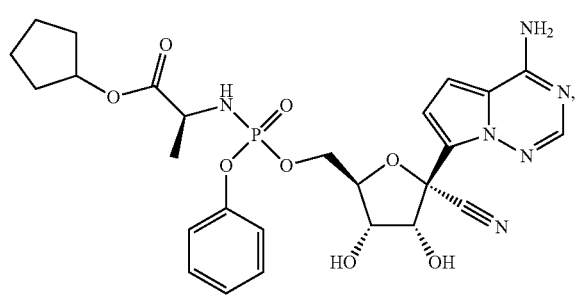
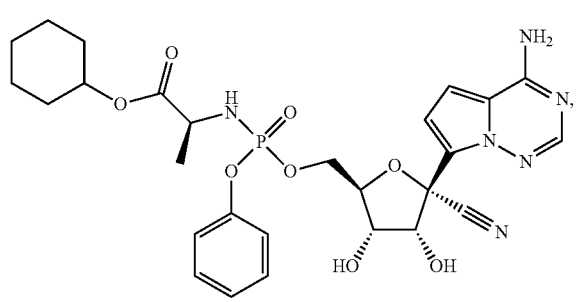
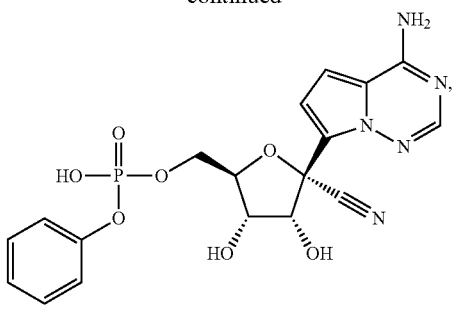
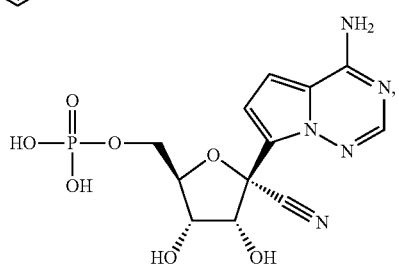
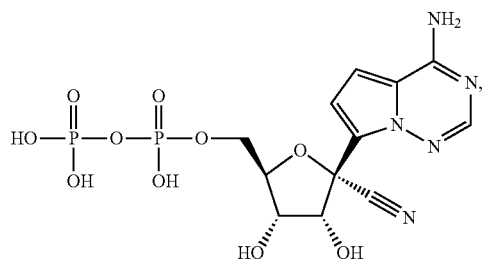
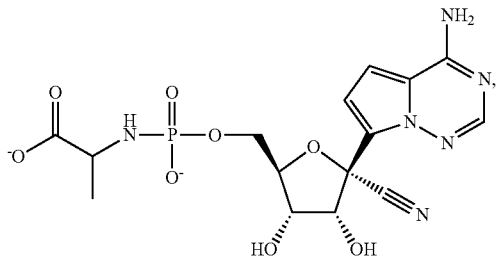
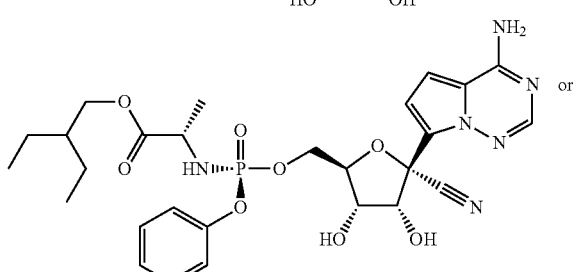
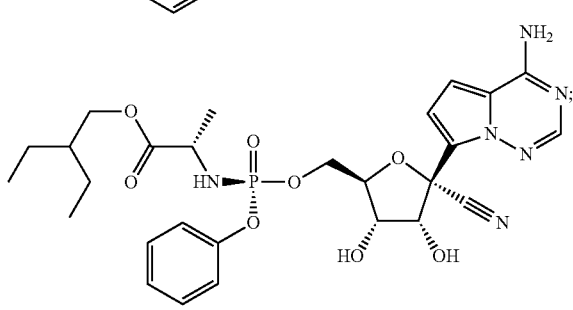
or a pharmaceutically acceptable salt, hydrate, or ester thereof In another embodiment, the present invention provides a compound that is

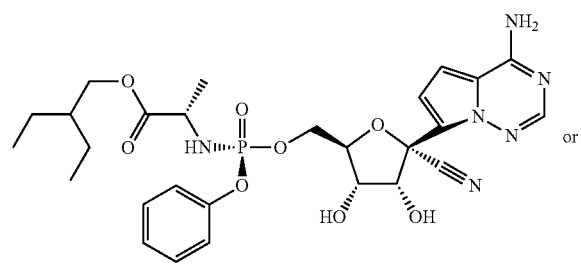

or

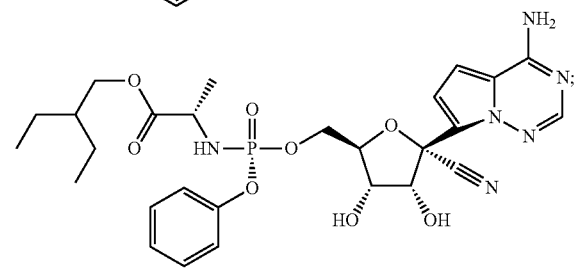

or a pharmaceutically acceptable salt or ester thereof

In another embodiment, the present invention provides a compound that is

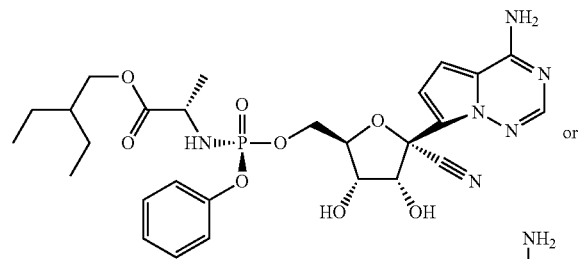

or

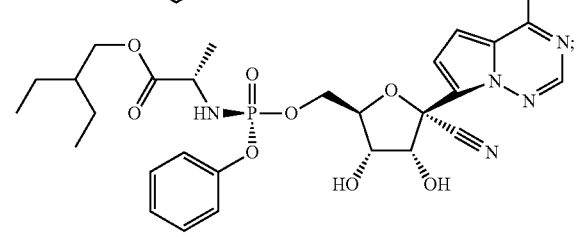

or a pharmaceutically acceptable salt or ester thereof

In another embodiment, the present invention provides a compound that is

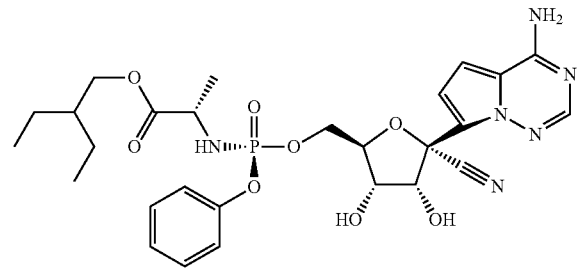 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

or a pharmaceutically acceptable salt or ester thereof

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula IV:

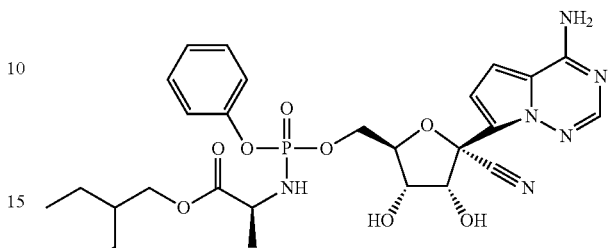

which is named (2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino) propanoate. Other compounds of the present invention include:

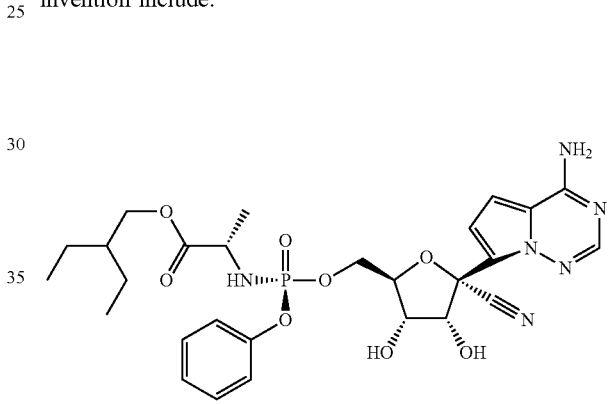

which is named (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)propanoate, and

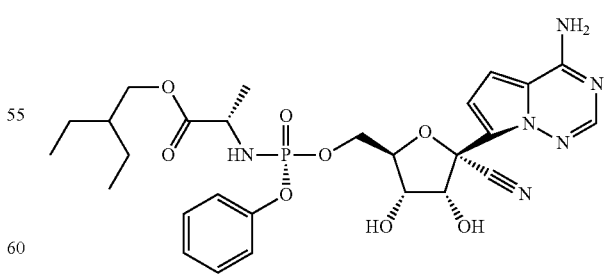

which is named (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)propanoate.

(S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate may also be illustrated as

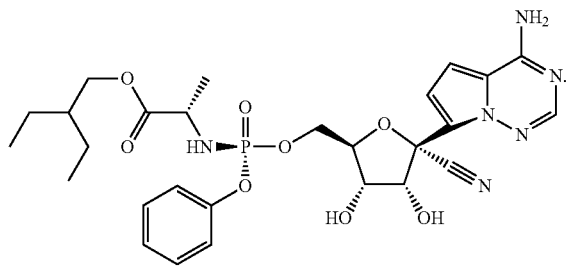 [SMILES: CCC(CC)COC(=O)[C@H](C)N[P@@](=O)(OC[C@H]1O[C@@](C#N)(c2ccc3c(N)ncnn23)[C@H](O)[C@@H]1O)Oc1ccccc1]

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

A compound of Formula IV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula IV and their pharmaceutically acceptable salts.

A compound of Formula IV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula IV and their pharmaceutically acceptable salts.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula IV and pharmaceutically acceptable salts thereof are embraced by the present invention. All mixtures of such enantiomers and diastereomers are within the scope of the present invention.

The compounds of the invention, exemplified by Formula IV may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula IV compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula IV in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula IV when administered to a mammal, particularly a human. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula IV.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "$R^1$", then it will be understood that the groups may be the same or different, i.e., each group is independently selected. Wavy lines, ⌇⌇⌇⌇⌇, indicate the site of covalent bond attachments to the adjoining substructures, groups, moieties, or atoms.

Selected substituents comprising the compounds of Formula IV are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $Z^3$. $Z^3$ can be $Z^4$ and $Z^4$ can be R or comprise substituents comprising R. Alternatively, $Z^3$ can be $Z^5$ which can comprise substituents comprising R. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $Z^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $Z^3$ will occur 0 to 8 times, $R^y$ will occur 0 to 6 times in a given embodiment. Even more typically, $Z^3$ will occur 0 to 6 times and $R^y$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

The compounds of the present invention can be prepared by methods known to one of skill in the art. For example, the compounds of the present invention can be prepared according to the methods described in U.S. Pat. No. 8,008,264 and U.S. Application Publication No. US 2012/0027752.

A. Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}$C or $^3$H) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti Filoviridae activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

III. Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to about 4. In some embodiments, the pH of the formulations ranges from about 2 to about 10, but is ordinarily about 3.5 to about 8.5.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carriers) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). Further non-limiting examples of suspending agents include Captisol® (sulfobutyl ether beta-cyclodextrin, SBE-β-CD). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. The sterile injectable preparation may also be a sterile injectable solution or suspension in a parenterally acceptable diluent or solvent. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, hypertonic sodium chloride solution, and hypotonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of Filoviridae infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

IV. Routes of Administration

One or more compounds of the invention (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

In the methods of the present invention for the treatment of Filoviridae infection, the compounds of the present invention can be administered at any time to a human who may come into contact with humans suffering from Filoviridae infection or is already suffering from Filoviridae infection. In some embodiments, the compounds of the present invention can be administered prophylactically to humans coming into contact with humans suffering from Filoviridae infection. In some embodiments, administration of the compounds of the present invention can be to humans testing positive for Filoviridae infection but not yet showing symptoms of Filoviridae infection. In some embodiments, administration of the compounds of the present invention can be to humans upon commencement of symptoms of Filoviridae infection.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

The effective dose of a compound of the present invention for treating the Filoviridae infection can depend on whether the dose is to be used prophylactically or to treat a human already suffering from Filoviridae infection. Moreover, the dose can depend on whether the human suffering from Filoviridae infection does not yet show symptoms or is already showing symptoms of Filoviridae infection. Larger doses may be necessary for treating humans testing positive for Filoviridae infection and for humans showing symptoms of Filoviridae infection as compared to humans receiving prophylactic treatment.

Any suitable period of time for administration of the compounds of the present invention is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated. The time for administration can depend on whether the compound is being administered prophylactically or to treat a human suffering from a Filoviridae infection. For example, a prophylactic administration can be for a period of time while the human is in regular contact with other humans suffering from a Filoviridae infection, and for a suitable period of time following the last contact with a human suffering from a Filoviridae infection. For humans already suffering from a Filoviridae infection, the period of administration can be for any length of time necessary to treat the patient and a suitable period of time following a negative test for Filoviridae infection to ensure the Filoviridae infection does not return.

V. Combination Therapy

Compositions of the invention are also used in combination with other active ingredients. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S, 3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), and rVSV-EBOV, and mixtures thereof. The compounds and compositions of the present invention may also be used in combination with phosphoramidate morpholino oligomers (PMOs), which are synthetic antisense oligonucleotide analogs designed to interfere with translational processes by forming base-pair duplexes with specific RNA sequences. Examples of PMOs include AVI-7287, AVI-7288, AVI-7537, AVI-7539, AVI-6002, and AVI-6003. The compounds and compositions of the present invention are also intended for use with general care provided patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting Filoviridae polymerase in a cell, comprising: contacting a cell infected with a Filovirus with an effective amount of a compound of Formula IV, or a pharmaceutically acceptable salt, solvate, and/or ester thereof, whereby Filoviridae polymerase is inhibited.

In still yet another embodiment, the present application provides for methods of inhibiting Filoviridae polymerase in a cell, comprising: contacting a cell infected with Filovirus with an effective amount of a compound of Formula IV, or a pharmaceutically acceptable salt, solvate, and/or ester thereof, and at least one additional active therapeutic agent, whereby Filoviridae polymerase is inhibited.

In still yet another embodiment, the present application provides for methods of inhibiting Filoviridae polymerase in a cell, comprising: contacting a cell infected with Filoviridae virus with an effective amount of a compound of Formula IV, or a pharmaceutically acceptable salt, solvate, and/or ester thereof, and at least one additional active therapeutic agent selected In still yet another embodiment, the present application provides for methods of treating Filoviridae virus infection in a human, comprising: administering to the patient a therapeutically effective amount of a compound of Formula IV, or a pharmaceutically acceptable salt, solvate, and/or ester thereof.

In still yet another embodiment, the present application provides for methods of treating Filoviridae virus infection in a human, comprising: administering to the patient a therapeutically effective amount of a compound of Formula IV, or a pharmaceutically acceptable salt, solvate, and/or ester thereof, and at least one additional active therapeutic agent, whereby Filoviridae polymerase is inhibited.

In still yet another embodiment, the present application provides for methods of treating Filoviridae virus infection in a human, comprising: administering to the patient a therapeutically effective amount of a compound of Formula IV, or a pharmaceutically acceptable salt, solvate, and/or ester thereof, and at least one additional active therapeutic agent.

Also provided is a kit that includes a compound of Formula IV, or a pharmaceutically acceptable salt, pharmaceutically acceptable ester, stereoisomer, mixture of stereoisomers or tautomer thereof. In separate embodiments individual kits are provided includes a compound selected from Formula IV herein, as well as each subgroup and embodiment thereof, including individual Compounds 1, 8, 9, 10, 12, 15, 17, 21, 22, 23, 24, 25, 26, 27, 28, 29, 30, 31, and 32 (Compounds 1-32), or a pharmaceutically acceptable salt, pharmaceutically acceptable ester, stereoisomer, mixture of stereoisomers or tautomer thereof. In one aspect, the kit comprises a compound of Formula IV, or a pharmaceutically acceptable salt thereof. Each of the individual kits described herein may comprise a label and/or instructions for use of the compound in the treatment of a disease or condition in a subject (e.g., human) in need thereof. In some embodiments, the disease or condition is a human Filoviridae viral infection, including an Ebola viral infection or a Marburg viral infection. In other embodiments, each separate kit may also contain instructions for use of additional medical agents in combination with the compound of Formula IV in the treatment of a disease or condition in a subject (e.g., human) in need thereof. In certain of these embodiments, the disease or condition is a human Filoviridae viral infection, including an Ebola viral infection or a Marburg viral infection. In each of the kits herein there is a further embodiment in which the kit comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula IV, or a pharmaceutically acceptable salt, pharmaceutically acceptable ester, stereoisomer, mixture of stereoisomers or tautomer thereof; and a container. In one aspect, the article of manufacture comprises a compound of Formula IV and individual Compounds 1, 8, 9, 10, 12, 15, 17, 21, 22, 23, 24, 25, 26, 27, 28, 29, 30, 31, and 32 (Compounds 1-32), or a pharmaceutically acceptable salt thereof, and a container. In separate embodiments, the container of the article of manufacture may be a vial, jar, ampoule, preloaded syringe, blister package, tin, can, bottle, box, or an intravenous bag.

VI. Methods of Inhibition of a Filoviridae Polymerase

Another aspect of the invention relates to methods of inhibiting the activity of Filoviridae polymerase comprising the step of treating a sample suspected of containing Filoviridae with a compound or composition of the invention.

Filoviridae that can be treated using the methods of the present invention are single-stranded negative sense RNA viruses that typically infect primates. Filoviruses are able to multiply in virtually all cell types. The Filovirus antigens and virions are found primarily in fibroblasts and interstitium of an infected individual. There are three identified genera of Filoviruses: the Ebola virus (EBOV; five species); the Marburg virus (MARV); and the Cuevavirus, also known as the Lloviu virus (LLOV). The virions (viral particles) are characteristically shaped as long, cylindrical, filamentous particles which may be straight, curved, coiled, or found in a "6" or "U" shaped configuration. They are occasionally branched and the particles vary greatly in length, but the diameter (about 80 nm) is consistent. The Filovirus genome comprises seven genes that encode 4 virion structural proteins (VP30, VP35, nucleoprotein (NP), and a polymerase protein (L-pol)) and 3 membrane-associated proteins (VP40, glycoprotein (GP), and VP24).

The Ebola virus genus includes five known species: (1) *Bundibugyo ebolavirus*, also known as Bundibugyo virus (BDBV, previously BEBOV); (2) *Reston ebolavirus*, also known as Reston virus or Ebola-Reston (RESTV, previously REBOV); (3) *Sudan ebolavirus*, also known as Sudan virus or Ebola-Sudan (SUDV, previously SEBOV); (4) *Tai Forest ebolavirus*, also known as Tai Forest virus or Ebola-Tai (TAFV, previously CIEBOV); and (5) *Zaire ebolavirus*, also known as Ebola virus or Ebola-Zaire (EBOV, previously ZEBOV).

The Marburg virus genus includes the species *Marburg marburgvirus*, also known as Marburg virus (MARV) or Ravn virus (RAVV). The Cuevavirus genus includes the species Lloviu cuevavirus, also known as the Lloviu virus (LLOV).

Compositions of the invention may act as inhibitors of Filoviridae polymerase, as intermediates for such inhibitors or have other utilities as described below. The inhibitors will bind to locations on the surface or in a cavity of Filoviridae polymerase having a geometry unique to Filoviridae polymerase. Compositions binding Filoviridae polymerase may bind with varying degrees of reversibility. Those compounds binding substantially irreversibly are ideal candidates for use in this method of the invention. Once labeled, the substantially irreversibly binding compositions are useful as probes for the detection of Filoviridae polymerase. Accordingly, the invention relates to methods of detecting Filoviridae polymerase in a sample suspected of containing Filoviridae polymerase comprising the steps of: treating a sample suspected of containing Filoviridae polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens.

The compounds herein are labeled in conventional fashion using functional groups such as hydroxyl, carboxyl, sulfhydryl or amino Within the context of the invention, samples suspected of containing Filoviridae polymerase include natural or manmade materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces Filoviridae polymerase, frequently a pathogenic organism such as a Filoviridae virus. Samples can be contained in any medium including water and organic solvent\water mixtures. Samples include living organisms such as humans, and manmade materials such as cell cultures.

The treating step of the invention comprises adding the composition of the invention to the sample or it comprises adding a precursor of the composition to the sample. The addition step comprises any method of administration as described above.

If desired, the activity of Filoviridae polymerase after application of the composition can be observed by any method including direct and indirect methods of detecting Filoviridae polymerase activity. Quantitative, qualitative, and semiquantitative methods of determining Filoviridae polymerase activity are all contemplated. Typically one of the screening methods described above are applied, however, any other method such as observation of the physiological properties of a living organism are also applicable.

Organisms that contain Filoviridae polymerase include the Filoviridae virus. The compounds of this invention are useful in the treatment or prophylaxis of Filoviridae infections in animals or in man.

However, in screening compounds capable of inhibiting human Filoviridae viruses, it should be kept in mind that the results of enzyme assays may not correlate with cell culture assays. Thus, a cell based assay should be the primary screening tool.

In another embodiment, the present application provides for methods of treating Filoviridae virus infection in a human, comprising: administering to the patient a therapeutically effective amount of a compound of Formula IV, or a pharmaceutically acceptable salt, solvate, and/or ester thereof. In some embodiments, the Filoviridae infection is caused by a Filoviridae virus. In some embodiments, the Filoviridae infection is caused by an Ebola virus. In some embodiments, the Filoviridae infection is caused by *Bundibugyo ebolavirus, Reston ebolavirus, Sudan ebolavirus, Tai Forest ebolavirus,* or *Zaire ebolavirus*. In some embodiments, the Filoviridae infection is caused by a Marburg virus. In some embodiments, the Filoviridae infection is caused by a Lloviu virus. In some embodiments, a Filoviridae polymerase is inhibited.

The compounds of the present invention can be used in the treatment of a human already suffering from a Filoviridae infection, or can be administered prophylactically to reduce or prevent the chance of a Filoviridae infection. Filoviridae infections can be characterized by hemorrhagic fever, hematemesis, diarrhea, retrosternal abdominal pain and prostration. The incubation period is around 21 days following contact with a human suffering from Filoviridae infection. The outcome of Filoviridae infection is typically death.

Also provided as separate embodiments are a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, for use in a method of treating a Filoviridae infection in a human. Also provided as separate embodiments are a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, for use in a method of treating an Ebola virus infection in a human. Also provided as separate embodiments are a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, for use in a method of treating a Marburg virus infection in a human. Within each of the embodiments herein in which the Filoviridae infection is an Ebola virus, there are further separate embodiments with them wherein the Filoviridae infection is caused, respectively, by *Bundibugyo ebolavirus, Reston ebolavirus, Sudan ebolavirus, Tai Forest ebolavirus,* or *Zaire ebolavirus*. In some embodiments, the Filoviridae infection is caused by a Marburg virus. In some embodiments, the Filoviridae infection is caused by a Lloviu virus.

The present invention also provides compounds of each of the Formula herein, as well as each subgroup and embodiment thereof, including a compound selected from the group of Formula (IV), or one of the specific compounds of the examples herein, including Compounds 1-32, or a pharmaceutically acceptable salt, solvate, and/or ester thereof for use in any of the methods of the invention as defined herein.

Also provided as separate embodiments are the uses of a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, in the preparation of a medicament for treating a Filoviridae infection in a human. Also provided as separate embodiments are the uses of a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, in the preparation of a medicament for treating an Ebola virus infection in a human. Also provided as separate embodiments are the uses of a compound selected from each of the Formulas herein, as well as each subgroup and embodiment thereof, including a compound selected from the group of Formula IV, or one of the specific compounds of the examples herein, including Compounds 1-32, or a pharmaceutically acceptable salt, solvate, and/or ester thereof, in the preparation of a medicament for treating a Marburg virus infection in a human.

VII. Screens for Filoviridae Polymerase Inhibitors

Compositions of the invention are screened for inhibitory activity against Filoviridae polymerase by any of the conventional techniques for evaluating enzyme activity. Within the context of the invention, typically compositions are first screened for inhibition of Filoviridae polymerase in vitro and compositions showing inhibitory activity are then screened for activity in vivo. Compositions having in vitro Ki (inhibitory constants) of less than about $5 \times 10^{-6}$ M and preferably less than about $1 \times 10^{-7}$ M are preferred for in vivo use.

Useful in vitro screens have been described in detail and will not be elaborated here. However, the examples describe suitable in vitro assays.

VIII. Preparation of Compounds

Examples

Certain abbreviations and acronyms are used in describing the experimental details. Although most of these would be understood by one skilled in the art, Table 1 contains a list of many of these abbreviations and acronyms.

TABLE 1

| List of abbreviations and acronyms. | |
|---|---|
| Abbreviation | Meaning |
| Ac₂O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| EtOAc | ethyl acetate |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |

TABLE 1-continued

| List of abbreviations and acronyms. | |
|---|---|
| Abbreviation | Meaning |
| MeOH | methanol |
| MMTC | mono methoxytrityl chloride |
| m/z or m/e | mass to charge ratio |
| MH⁺ | mass plus 1 |
| MH⁻ | mass minus 1 |
| MsOH | methanesulfonic acid |
| MS or ms | mass spectrum |
| MTBE | tert-butylmethyl ether |
| NBS | N-bromosuccinimide |
| Ph | phenyl |
| rt or r.t. | room temperature |
| TBAF | tetrabutylammonium fluoride |
| THF | tetrahydrofuran |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

A. Preparation of Compounds

Example 1

(2S)-ethyl 2-(chloro(phenoxy)phosphorylamino)propanoate (Chloridate A)

Ethyl alanine ester hydrochloride salt (1.69 g, 11 mmol) was dissolved in anhydrous CH₂Cl₂ (10 mL) and the mixture stirred with cooling to 0° C. under N₂ (g). Phenyl dichlorophosphate (1.49 mL, 10 mmol) was added followed by dropwise addition of Et₃N over about 10 min. The reaction mixture was then slowly warmed to RT and stirred for about 12 h. Anhydrous Et₂O (50 mL) was added and the mixture stirred for about 30 min. The solid that formed was removed by filtration, and the filtrate concentrated under reduced pressure. The residue was subjected to silica gel chromatography eluting with 0-50% EtOAc in hexanes to provide intermediate A. $^1$H NMR (300 MHz, CDCl$_3$) δ 7.39-7.27 (m, 5H), 4.27 (m, 3H), 1.52 (m, 3H), 1.32 (m, 3H). $^{31}$P NMR (121.4 MHz, CDCl$_3$) δ 8.2, 7.8.

Example 2

(2S)-2-ethylbutyl 2-(chloro(phenoxy)phosphorylamino)propanoate (Chloridate B)

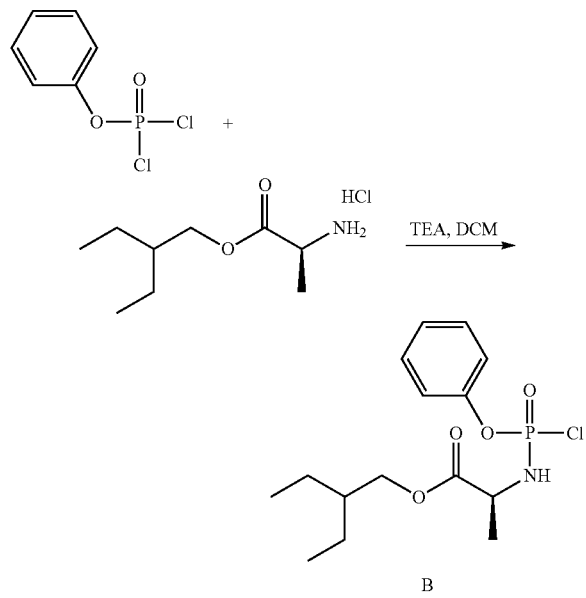

The 2-ethylbutyl alanine chlorophosphoramidate ester B was prepared using the same procedure as chloridate A except substituting 2-ethylbutyl alanine ester for ethyl alanine ester. The material is used crude in the next reaction. Treatment with methanol or ethanol forms the displaced product with the requisite LCMS signal.

Example 3

(2S)-isopropyl 2-(chloro(phenoxy)phosphorylamino)propanoate (Chloridate C)

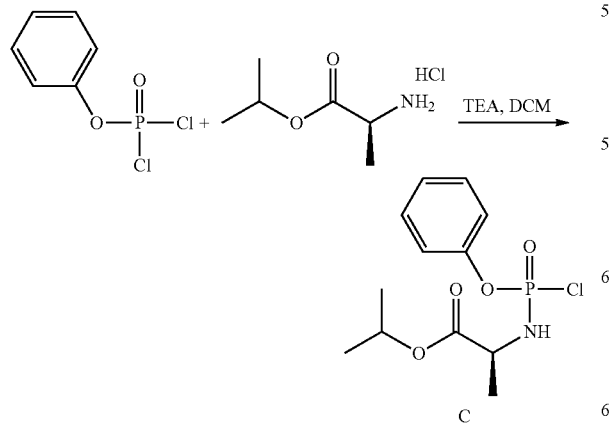

The isopropyl alanine chlorophosphoramidate ester C was prepared using the same procedure as chloridate A except substituting isopropyl alanine ester for the ethyl alanine ester.

The material is used crude in the next reaction. Treatment with methanol or ethanol forms the displaced product with the requisite LCMS signal.

Example 4

(2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile (Compound 1)

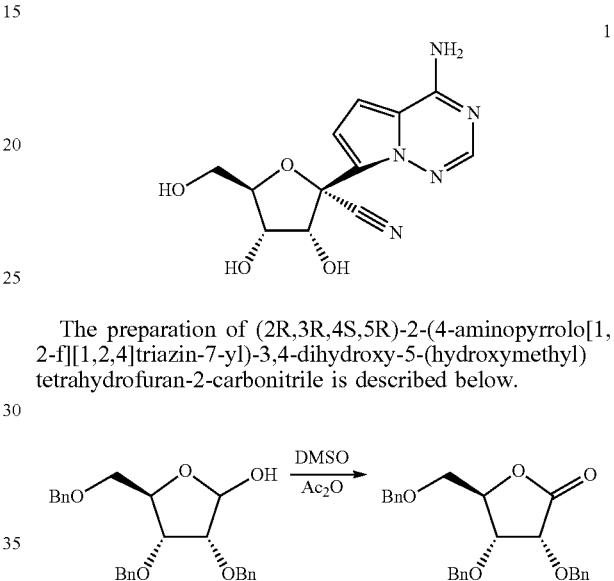

The preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile is described below.

The commercially available lactol (10 g, 23.8 mmol) was dissolved in anhydrous DMSO (30 mL) under N$_2$ (g). Ac$_2$O (20 mL) was added and the resultant reaction mixture stirred at RT for about 48 h. The reaction mixture was poured onto ice H$_2$O (500 mL) and the mixture stirred for 20 min. The mixture was extracted with EtOAc (3×200 mL) and the combined organic extracts were then washed with H$_2$O (3×200 mL). The organic extract was dried over anhydrous MgSO$_4$, filtered and concentrated under reduced pressure. The residue was dissolved in CH$_2$Cl$_2$ and subjected to silica gel chromatography eluting with 25% EtOAc in hexanes to provide the lactone. $^1$H NMR (400 MHz, DMSO) δ 7.30-7.34 (m, 13H), 7.19-7.21 (m, 2H), 4.55-4.72 (m, 6H), 4.47 (s, 2H), 4.28 (d, J=3.9 Hz, 1H), 3.66 (m, 2H). LCMS m/z 436.1 [M+H$_2$O], 435.2 [M+OH]− Tr=2.82 min. HPLC Tr=4.59 [2-98% ACN in H2) over 5 min at 2 mL/min flow.

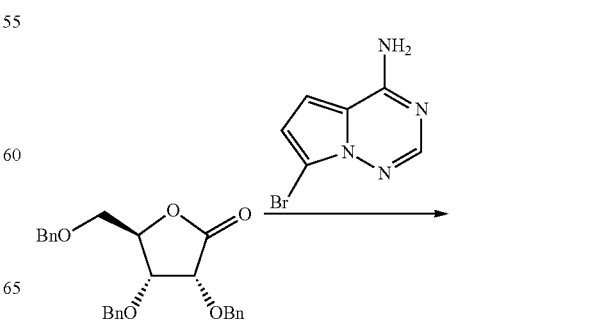

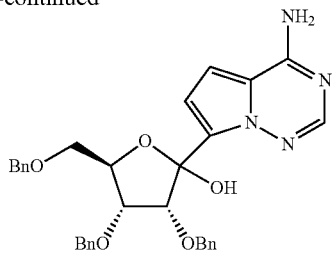

The bromopyrazole (prepared according to WO2009/132135) (0.5 g, 2.4 mmol) was suspended in anhydrous THF (10 mL) under N₂ (g). The suspension was stirred and TMSCl (0.67 mL, 5.28 mmol) was added. The mixture was stirred for 20 min. at RT and then cooled to about −78° C. after which time a solution of n-BuLi (6 mL, 1.6 N in hexanes, 9.6 mmol) was added slowly. The reaction mixture was stirred for 10 min. at about −78° C. and then the lactone (1 g, 2.4 mmol) was added via syringe. When the reaction was complete as measured by LCMS, AcOH was added to quench the reaction. The mixture was concentrated under reduced pressure and the residue dissolved in a mixture of CH₂Cl₂ and H₂O (100 mL, 1:1). The organic layer was separated and washed with H₂O (50 mL). The organic layer was then dried over anhydrous MgSO₄, filtered and concentrated under reduced pressure. The residue was subjected to silica gel chromatography eluting with 0-50% EtOAc in hexanes to provide the product as a 1:1 mixture of anomers. LCMS m/z 553 [M+H].

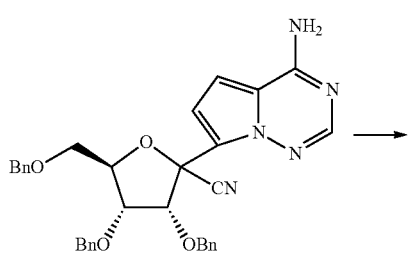

The hydroxy nucleoside (1.1 g, 2.0 mmol) was dissolved in anhydrous CH₂Cl₂ (40 mL) and the solution cooled with stirring to about −78° C. under N₂ (g). TMSCN (0.931 mL, 7 mmol) was added and the mixture stirred for a further 10 min. TMSOTf (1.63 mL, 9.0 mmol) was slowly added to the reaction and the mixture stirred for 1 h. The reaction mixture was then diluted with CH₂Cl₂ (120 mL) and aqueous NaHCO₃ (120 mL) was added to quench the reaction. The reaction mixture was stirred for a further 10 min and the organic layer separated. The aqueous layer was extracted with CH₂Cl₂ (150 mL) and the combined organic extracts dried over anhydrous MgSO₄, filtered and concentrated under reduced pressure. The residue was dissolved in a minimal amount of CH₂Cl₂ and subjected to silica gel chromatography eluting with a gradient of 0-75% EtOAc and hexanes to provide the tribenzyl cyano nucleoside as a mixture of anomers. ¹H NMR (300 MHz, CD₃CN) δ 7.94 (s, 0.5H), 7.88 (s, 0.5H), 7.29-7.43 (m, 13H), 7.11-7.19 (m, 1H), 6.82-6.88 (m, 1H), 6.70-6.76 (m, 1H), 6.41 (bs, 2H), 5.10 (d, J=3.9 Hz, 0.5H), 4.96 (d, J=5.1 Hz, 0.5H), 4.31-4.85 (m, 7H), 4.09-4.18 (m, 2H), 3.61-3.90 (m, 2H). LCMS m/z 562 [M+H].

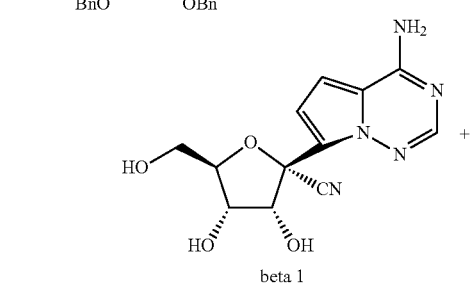

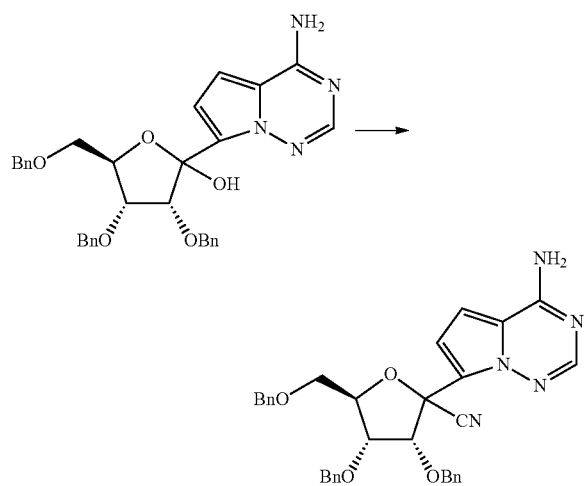

The tribenzyl cyano nucleoside (70 mg, 0.124 mmol) was dissolved in anhydrous CH₂Cl₂ (2 mL) and cooled to about −20° C. under N₂ (g). A solution of BCl₃ (1N in CH₂Cl₂, 0.506 mL, 0.506 mmol) was added and the reaction mixture stirred for 1 h. at −78° C. When the reaction was complete by LC/MS, MeOH was added to quench the reaction. The reaction mixture was allowed to warm to RT and the solvent removed under reduced pressure. The residue was subjected to C18 reverse phase HPLC, eluting for 5 min with H₂O (0.1% TFA), followed by a gradient of 0-70% MeCN in H₂O (0.1% TFA) over 35 min, to elute the α-anomer, and β-anomer 1. (α-anomer)¹H NMR (300 MHz, D₂O) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H). (β-anomer)¹H NMR (400 MHz, DMSO) δ 7.91 (s, 1H), 7.80-8.00 (br s, 2H), 6.85-6.89 (m, 2H), 6.07 (d, J=6.0 Hz, 1H), 5.17 (br s, 1H), 4.90 (br s, 1H), 4.63 (t, J=3.9 Hz, 1H), 4.02-4.06 (m, 1H), 3.94 (br s, 1H), 3.48-3.64 (m, 2H). LCMS m/z 292.2 [M+H], 290.0 [M−H]. Tr=0.35 min. 13C NMR (400 MHZ, DMSO), 156.0, 148.3, 124.3, 117.8, 117.0, 111.2, 101.3, 85.8, 79.0, 74.7, 70.5, 61.4. HPLC Tr=1.32 min Preparation of (3R,4R,5R)-2-(4-aminopyrrolo[2,1-f]
[1,2,4]triazin-7-yl)-3,4-bis(benzyloxy)-5-((benzyloxy)methyl)tetrahydrofuran-2-ol using LaCl$_3$·2LiCl

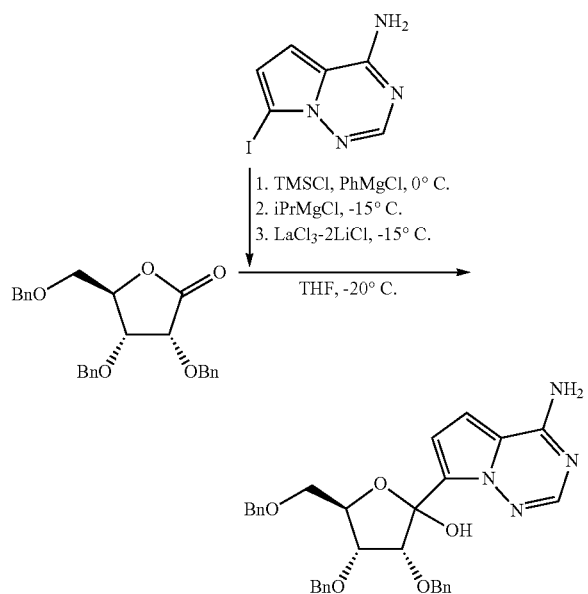

A solution of 7-iodopyrrolo[2,1-f][1,2,4]triazin-4-amine (7.5 g, 28.8 mmol, 1.0 equiv) was prepared in THF (67 mL). The solution was cooled to about 0° C., and TMSCl (3.3 mL, 30.3 mmol, 1.05 equiv) was added. The reaction mixture was stirred for about 30 min, and then PhMgCl (2 M in THF; 28 mL, 56.8 mmol, 1.97 equiv) was added while maintaining an internal temperature below 5° C. The reaction mixture was agitated at about 0° C. for about 35 min, and then cooled to about −15° C. iPrMgCl (2 M in THF, 14 mL, 30.2 mmol, 1.05 equiv) was then added while maintaining an internal temperature below about −10° C. After approximately 15 minutes at about −15° C., LaCl$_3$·2LiCl (0.6 M in THF, 50 mL, 14.4 mmol, 0.5 equiv) was added while maintaining an internal temperature below about −15° C. The reaction mixture was agitated for about 25 min at about −20° C.

In a separate flask, a solution of (3R,4R,5R)-3,4-bis(benzyloxy)-5-((benzyloxy)methyl)dihydrofuran-2(3H)-one (10.0 g, 23.9 mmol, 0.83 equiv) was prepared in THF (45 mL). The solution was cooled to about −20° C., and then transferred to the Grignard solution while maintaining an internal temperature below about −15° C. The resulting reaction mixture was agitated at about −20° C. for about 30 min.

The reaction was quenched with 2 M HCl (53 mL), and the mixture warmed to about 15° C. iPrOAc (38 mL) was added, and the organic and aqueous phases were separated. The bottom aqueous layer was discharged, and the upper organic layer was washed sequentially with 2.5 wt % NaHCO$_3$ (53 mL), 2.5 wt % NaHCO$_3$ (53 mL), and 10 wt % NaCl (53 mL).

The organic phase was concentrated to about 45 mL, and then diluted with iPrOAc (75 mL). The solution was concentrated again to about 45 mL, and then diluted with iPrOAc (23 mL). The solution was concentrated to about 45 mL, and then filtered over a pad of Celite. The filtered solution was concentrated to about 26 mL, and then diluted with MTBE (75 mL). After 2 h, heptane (23 mL) was slowly added and the slurry was stirred at about 25° C. for about 2 h, and was then cooled to about −5° C. over about 8 h. The solids were isolated by filtration, and the filter cake was washed with MTBE/heptane (4:1, 23 mL). The solids were dried in a vacuum oven at no more than about 35° C. to afford (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol.

Preparation of (3R,4R,5R)-2-(4-aminopyrrolo[2,1-f]
[1,2,4]triazin-7-yl)-3,4-bis(benzyloxy)-5-((benzyloxy)methyl)tetrahydrofuran-2-ol using CeCl$_3$

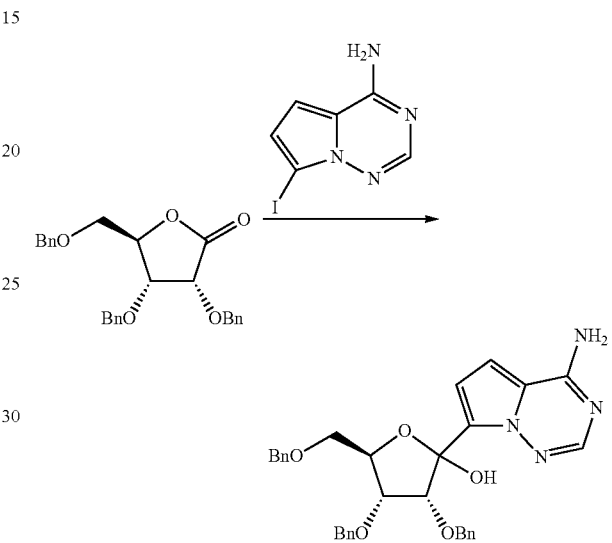

The iodopyrazole (5.02 g, 19.3 mmol) was dissolved in THF (45 g) and the solution was cooled to about 0° C. with stirring. TMSCl (2.04 g, 18.7 mmol) was added, and after about 1 h phenyl magnesium chloride (2.0 M in THF, 19.9 g, 38.2 mmol) was added. The reaction mixture was cooled to about −20° C. and iso-propyl magnesium chloride (2.0 M in THF, 9.99 g, 20.5 mmol) was added slowly. After about 30 min, the reaction mixture was transferred to a mixture of anhydrous cerium chloride (4.75 g, 19.3 mmol) in THF (22 g) at about −20° C. After about 1.5 h a solution of lactone (6.73 g, 16.1 mmol) in THF (22 g) was added slowly, and the resulting reaction mixture was stirred for about 1 h. 2 M HCl (41 g) was added, the mixture was warmed to about 15° C., and iso-propyl acetate (35 g) was added. The layers were separated and the organic layer was washed with 2.5% NaHCO$_3$ (2×40 g), 10% NaCl (1×35 g) and concentrated about 30 mL volume. iso-Propyl acetate (44 g) was charged and the solution was concentrated to about 30 mL volume. iso-Propyl acetate (43 g) was charged and the solution was concentrated to about 30 mL volume. The solution was filtered and the filtrate was concentrated to about 18 mL volume. tert-Butylmethyl ether (37 g) was added followed by product seed crystals (10.7 mg). After about 14 h n-heptane (10.5 g) was added and the mixture was cooled to about −5° C. and filtered. The solids were washed with tert-butylmethyl ether (9 g) at about −5° C. and dried under vacuum at about 34° C. for about 15 h to provide the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol using CeCl₃ and iPrMgCl-LiCl

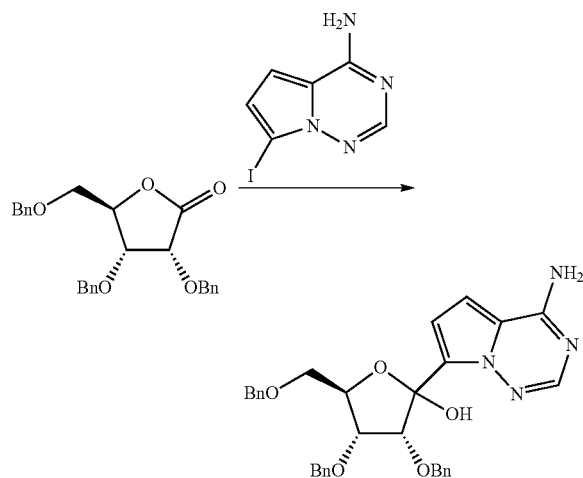

The iodopyrazole (5.03 g, 19.3 mmol) was dissolved in THF (45 g) and the solution was cooled to about 0° C. with stirring under N₂(g). TMSCl (2.06 g, 19.0 mmol) was added, and after about 1 h phenyl magnesium chloride (2.0 M in THF, 20.23 g, 38.8 mmol) was added. The reaction mixture was cooled to about −20° C. and iso-propyl magnesium chloride-lithium chloride complex (2.0 M in THF, 15.37 g, 21.0 mmol) was added slowly. After about 1 h, the reaction mixture was transferred to a mixture of cerium chloride (4.77 g, 19.4 mmol) in THF (22 g) at about −20° C. After about 1 h a solution of lactone (6.75 g, 16.1 mmol) in THF (23 g) was added slowly, and the resulting reaction mixture was stirred for about 1.5 h. 2 M HCl (40 g) was added, the mixture was warmed to about 15° C. and iso-propyl acetate (35 g) was added. The layers were separated and the organic layer was washed with 2.5% NaHCO₃ (2×40 g), 10% NaCl (1×36 g) and concentrated to about 30 mL volume. iso-Propyl acetate (44 g) was added and the solution was concentrated to about 30 mL volume. The solution was filtered and the filtrate was concentrated to about 18 mL volume. tert-Butylmethyl ether (37 g) was added followed by product seed crystals (10.5 mg). After about 14 h n-heptane (11 g) was added and the mixture was cooled to about −5° C. and filtered. The solids were washed with tert-butylmethyl ether (9 g) at about −5° C. and dried under vacuum at about 34° C. for about 15 h to provide the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol using YCl₃

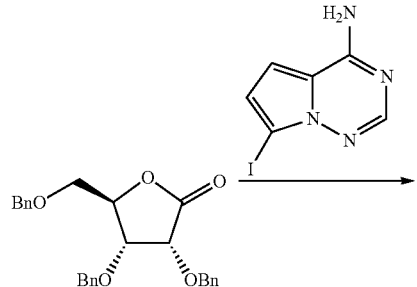

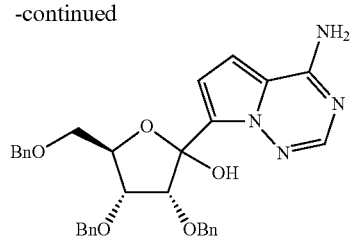

The iodopyrazole (4.99 g, 19.2 mmol) was dissolved in THF (44 g) and the solution was cooled to about 0° C. with stirring. TMSCl (2.45 mL, 19.4 mmol) was added, and after about 30 min phenyl magnesium chloride (2.0 M in THF, 20.29 g, 39.0 mmol) was added. The reaction mixture was cooled to about −20° C. and iso-propyl magnesium chloride (2.0 M in THF, 9.85 g, 20.1 mmol) was added slowly. After about 30 min, the reaction mixture was transferred into a mixture of anhydrous yttrium chloride (3.76 g, 19.3 mmol) and lactone (6.68 g, 16.0 mml) in THF (24 g) at about −20° C. After about 2.5 h 2 M HCl (30 g) was added, the mixture was warmed to about 15° C., and iso-propyl acetate (22 g) was added. The layers were separated and the organic layer was washed with 2.5% NaHCO₃ (2×40 g), 10% NaCl (1×35 g) and concentrated to about 30 mL volume. iso-Propyl acetate (44 g) was charged and the solution was concentrated to about 30 mL volume. iso-Propyl acetate (45 g) was charged and the solution was concentrated to about 30 mL volume. The solution was filtered and the filtrate was concentrated to about 18 mL volume. tert-Butylmethyl ether (37 g) was added followed by product seed crystals (11.5 mg). After about 1 h n-heptane (15 mL) was added and the mixture was cooled to about −5° C. and agitated for about 17 h. The slurry was filtered and the solids were washed with a tert-butylmethyl ether (8 g)/n-heptane (2 g) mixture precooled to about −5° C. The resulting solids were dried under vacuum at about 34° C. for about 22 h to afford the product.

Preparation of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol using NdCl₃

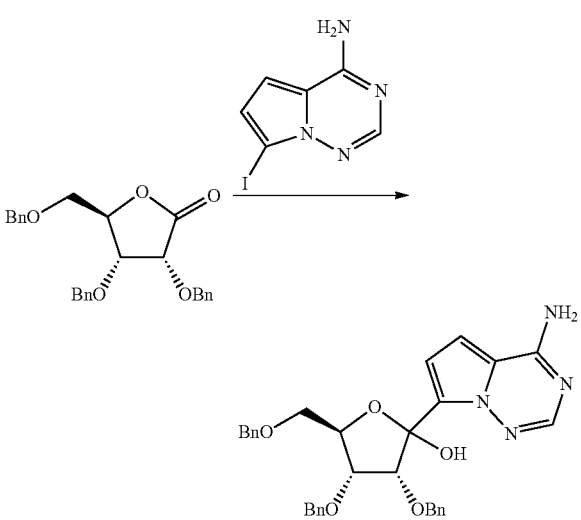

The iodopyrazole (5.02 g, 19.3 mmol) was dissolved in THF (38 g) and the solution was cooled to about 0° C. with stirring under N₂(g). TMSCl (2.45 mL, 19.4 mmol) was added, and after about 1 h phenylmagnesium chloride (2.0 M in THF, 19.75 g, 38.0 mmol) was added. The reaction mixture was cooled to about −20° C. and iso-propylmagnesium chloride (2.0 M in THF, 9.40 g, 19.2 mmol) was added slowly. After about 1.5 h, the reaction mixture was transferred into a mixture of anhydrous neodymium (III) chloride (4.03 g, 16.1 mmol) and lactone (6.70 g, 16.0 mml) in THF (22 g) at about −20° C. After about 1.5 h the reaction mixture was warmed to −10° C. and, after an additional 2 h, 2 M HCl (36 g) was added. The mixture was warmed to about 15° C. and iso-propyl acetate (23 g) was added. The layers were separated and the organic layer was washed with 2.5% NaHCO₃ (2×44 g), 10% NaCl (1×41 g) and concentrated to about 30 mL volume. iso-Propyl acetate (44 g) was charged and the solution was concentrated to about 30 mL volume. iso-Propyl acetate (45 g) was charged and the solution was concentrated to about 30 mL volume. The solution was filtered and the filtrate was concentrated to about 18 mL volume. tert-Butylmethyl ether (37 g) was added followed by product seed crystals (11.9 mg). After about 1 h n-heptane (15 mL) was added and the mixture was cooled to about −5° C. and agitated for about 15 h. The slurry was filtered and the solids were washed with a tert-butylmethyl ether (8 g)/n-heptane (11 g) mixture precooled to about −5° C. The resulting solids were dried under vacuum at about 34° C. for about 25 h to afford the product.

Preparation of (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile

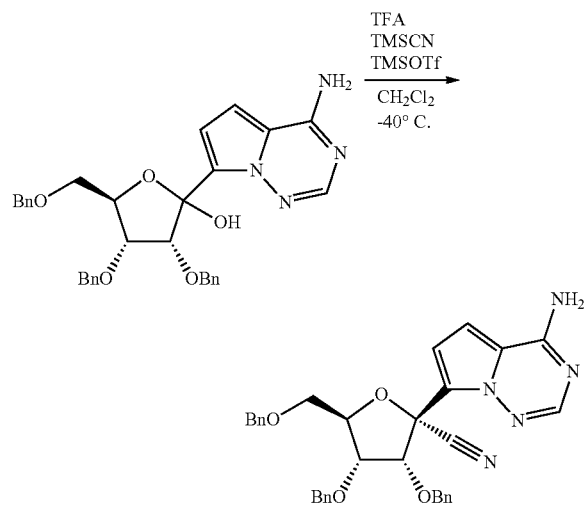

To a pre-cooled (−40° C.) solution of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol (10.0 grams, 18.1 mmols, 1.0 equiv.) in DCM (100 mL) was charged trifluoroacetic acid (6.19 grams, 54.3 mmols, 3.0 equiv.), followed by a pre-cooled (−30° C.) solution of TMSOTf (24.1 grams, 108.6 mmols, 6.0 equiv.) and TMSCN (10.8 grams, 108.6 mmols, 6.0 equiv.) in DCM (50 mL) while maintaining the internal temperature below about −25° C. The reaction mixture was agitated at below about −30° C. for no less than 10 minutes and quenched into a pre-cooled (about −10° C.) solution of 20 wt. % KOH aq. (120 mL). The bi-phasic mixture was warmed to ambient temperature. The organic layer was separated and washed with 10 wt. % NaCl aq. (3×50 mL). The organic phase was filtered, concentrated under vacuum to about 50 mL, re-diluted with toluene (200 mL) and concentrated under vacuum to 140 mL at about 50° C. The solution was seeded with (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile at about 55° C. Agitated at about 55° C. for about an hour and cooled to about 0° C. over about 6 hours. The solids were isolated by filtration and the filter cake was washed with toluene (30 mL). The solids were dried under vacuum at about 50° C.

Preparation of (2R,3R,4R,5R)-2-(4-aminopyrrolo[2,1-f][1,2,4]triazin-7-yl)-3,4-bis(benzyloxy)-5-((benzyloxy)methyl)tetrahydrofuran-2-carbonitrile via Flow Chemistry

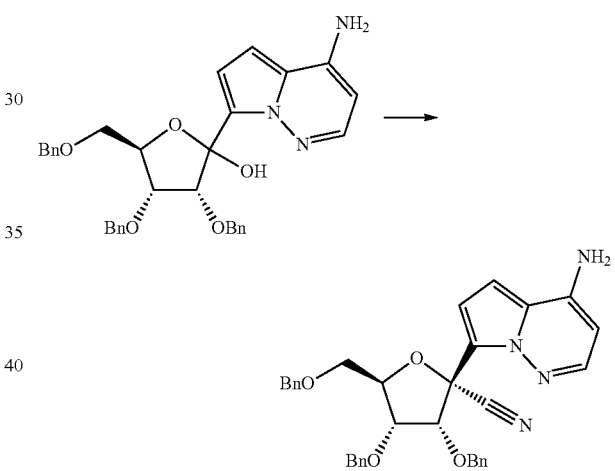

Solutions of (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol (23.0 g in 460.07 g of DCM), TMSOTf (55.81 g in 138.07 g of DCM) and TMSCN (25.03 g in 138.10 g of DCM) were sequentially pumped, into a tube reactor at about −40° C. The reaction mixture was collected in a flask, kept in ice bath, containing 20% KOH aqueous solution (46.91 g KOH and 210 g of water). The layers were separated and the organic phase was sequentially washed with 10% KOH aqueous solution (10 g KOH and 90 mL of water) and with 10% brine (2×100 g). The organic phase was concentrated under vacuum to about 4 volumes, isopropyl alcohol was charged (162.89 g) and the mixture was concentrated under vacuum to about 10 volumes. The contents were warmed to about 60° C., then adjusted to about 0° C. over about 6.5 h and agitated at about 0° C. for about 15.5 h. The resulting slurry was filtered, the solids were rinsed with isopropyl alcohol (61.79 g) and then dried at about 50° C. under reduced pressure overnight to afford the product.

Preparation of (2R,3R,4S,5R)-2-(4-aminopyrrolo[1,2-f][1,2,4]triazin-7-yl)-3,4-dihydroxy-5-(hydroxymethyl)tetrahydrofuran-2-carbonitrile

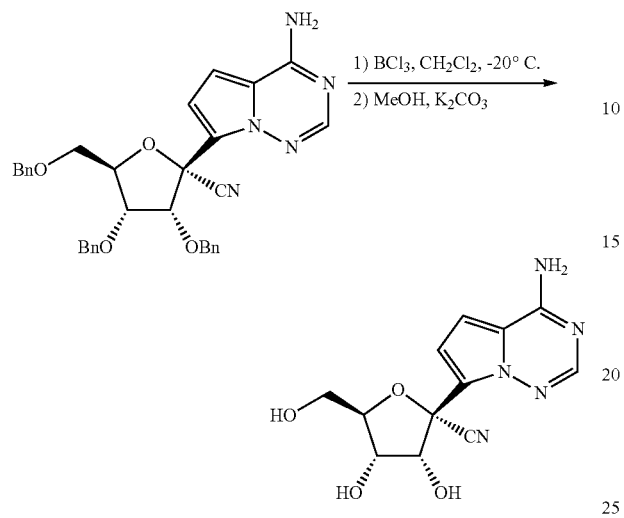

The tribenzyl cyano nucleoside (48.8 g, 86.9 mmol, 1.0 equiv.) was dissolved in anhydrous $CH_2Cl_2$ (244 mL) and cooled to about −20° C. A solution of $BCl_3$ (1M in $CH_2Cl_2$, 295 mL, 295 mmol, 3.4 equiv.) was added dropwise, maintaining the internal temperature below about −15° C. Following addition, the reaction mixture was stirred for 1 h at about −20° C. MeOH (340 ml) was added dropwise, maintaining the internal temperature below −15° C. The resulting solution was distilled to about 250 ml, then refilled with about 250 ml MeOH. The resulting solution was again distilled to about 250 ml, then refilled with about 250 ml MeOH, and finally distilled to about 125 ml. Water (125 ml) was added, followed by $K_2CO_3$ solution (20 wt % in water, 125 ml). The pH was checked, and found to be ~3. $K_2CO_3$ solution was added (20 wt % in water, 50 ml), and the pH was found to be ~8. The resulting slurry was stirred overnight, then filtered and washed with water (50 ml) and MeOH (50 ml). The wet product cake was dried overnight at about 40° C. overnight. $^1H$ NMR (300 MHz, $D_2O$) δ 7.96 (s, 1H), 7.20 (d, J=4.8 Hz, 1H), 6.91 (d, J=4.8 Hz, 1H), 4.97 (d, J=4.4 Hz, 1H), 4.56-4.62 (m, 1H), 4.08-4.14 (m, 1H), 3.90 (dd, J=12.9, 2.4 Hz, 1H), 3.70 (dd, J=13.2, 4.5 Hz, 1H).

Example 11

(2S)-isopropyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)-phosphorylamino)propanoate (Compound 8)

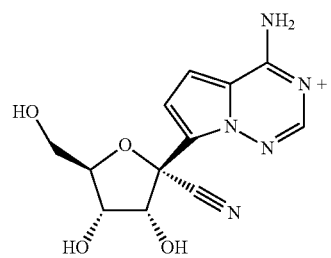

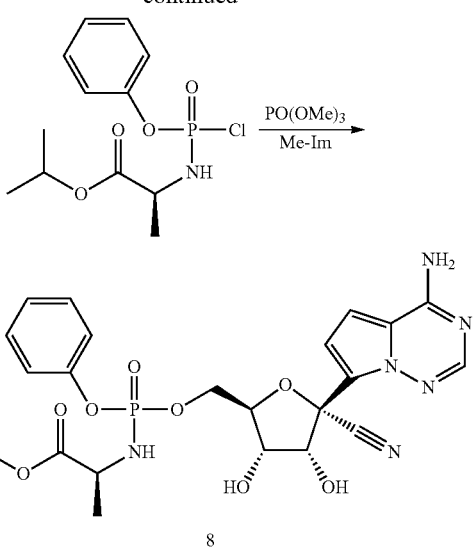

The nucleoside 1 (45 mg, 0.15 mmol) was dissolved in anhydrous trimethyl phosphate (0.5 mL) and the solution stirred under $N_2$ (g) at about 0° C. Methyl imidazole (36 μL, 0.45 mmol) was added to the solution. Chlorophosphoramidate C (69 mg, 0.225 mmol) was dissolved in anhydrous THF (0.25 mL) and added dropwise to the nucleoside mixture. When the reaction was complete by LCMS, the reaction mixture was diluted with EtOAc and washed with saturated aqueous $NaHCO_3$ solution, saturated NaCl, dried over anhydrous $Na_2SO_4$, filtered and concentrated under reduced pressure. The residue was subjected to silica gel chromatography eluting with 0-5% MeOH in $CH_2Cl_2$ followed by preparative HPLC to give the product. $^1H$ NMR (300 MHz, $CD_3OD$) δ 7.95 (m, 1H), 7.31-6.97 (m, 7H), 4.94 (m, 1H), 4.78 (m, 1H), 4.43 (m, 3H), 4.20 (m, 1H), 3.80 (d, 1H), 1.30-1.18 (m, 9H). $^{31}P$ NMR (121.4 MHz, $CD_3OD$) δ 3.8. LCMS m/z 561.0 [M+H], 559.0 [M−H].

Example 12

(2S)-2-ethylbutyl 2-((((2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino) propanoate (Compound 9)

Compound 9 can be prepared by several methods described below.

Procedure 1

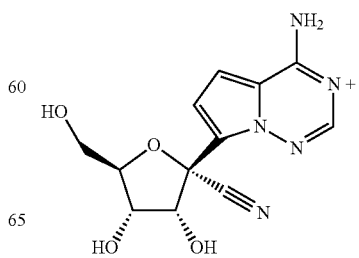

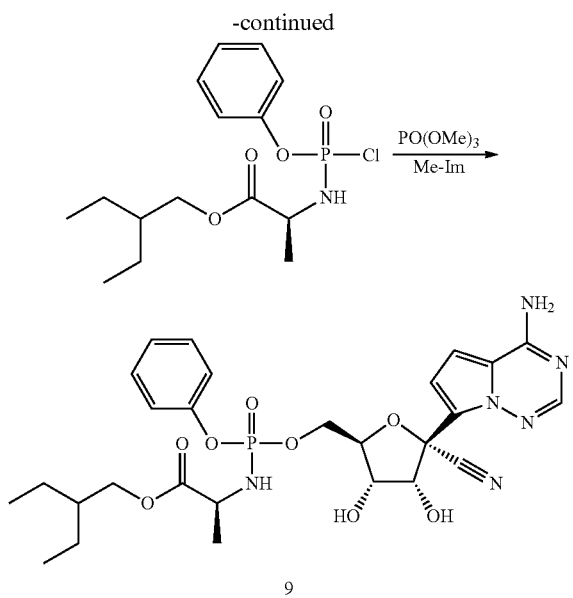

Prepared from Compound 1 and chloridate B according to the same method as for the preparation of compound 8. $^1$H NMR (300 MHz, CD$_3$OD) δ 7.87 (m, 1H), 7.31-7.16 (m, 5H), 6.92-6.89 (m, 2H), 4.78 (m, 1H), 4.50-3.80 (m, 7H), 1.45-1.24 (m, 8H), 0.95-0.84 (m, 6H). $^{31}$P NMR (121.4 MHz, CD$_3$OD) δ 3.7. LCMS m/z 603.1 [M+H], 601.0 [M−H].

Procedure 2

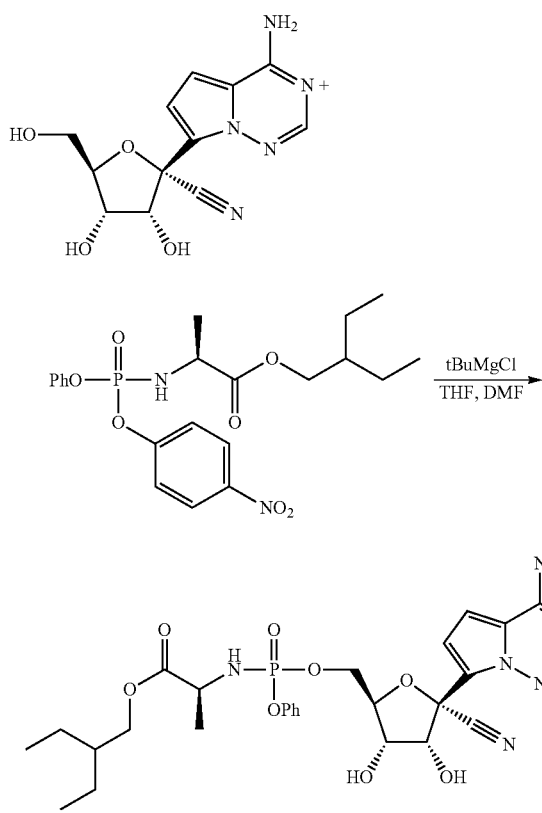

(2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (2S)-2-ethylbutyl 2-(((4-nitrophenoxy)(phenoxy)phosphoryl)amino)propanoate (1.08 g, 2.4 mmol) was dissolved in anhydrous DMF (9 mL) and stirred under a nitrogen atmosphere at RT. (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (350 mg, 1.2 mmol) was added to the reaction mixture in one portion. A solution of t-butylmagnesium chloride in THF (1M, 1.8 mL, 1.8 mmol) was then added to the reaction dropwise over about 10 minutes. The reaction was stirred for about 2 h, at which point the reaction mixture was diluted with ethyl acetate (50 mL) and washed with saturated aqueous sodium bicarbonate solution (3×15 mL) followed by saturated aqueous sodium chloride solution (15 mL). The organic layer was dried over anhydrous sodium sulfate and concentrated under reduced pressure. The resulting oil was purified with silica gel column chromatography (0-10% MeOH in DCM) to afford (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (311 mg, 43%, 1:0.4 diastereomeric mixture at phosphorus) as a white solid. $^1$H NMR (400 MHz, CD$_3$OD) δ 7.85 (m, 1H), 7.34-7.23 (m, 2H), 7.21-7.09 (m, 3H), 6.94-6.84 (m, 2H), 4.78 (d, J=5.4 Hz, 1H), 4.46-4.33 (m, 2H), 4.33-4.24 (m, 1H), 4.18 (m, 1H), 4.05-3.80 (m, 3H), 1.52-1.39 (m, 1H), 1.38-1.20 (m, 7H), 0.85 (m, 6H). $^{31}$P NMR (162 MHz, CD$_3$OD) δ 3.71, 3.65. LCMS m/z 603.1 [M+H], 600.9 [M−H]. HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.544 min, 5.601 min Separation of the (S) and (R) Diastereomers (2 S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate was dissolved in acetonitrile. The resulting solution was loaded onto Lux Cellulose-2 chiral column, equilibrated in acetonitrile, and eluted with isocratic acetonitrile/methanol (95:5 vol/vol). The first eluting diastereomer had a retention time of 17.4 min, and the second eluting diastereomer had a retention time of 25.0 min.

First Eluting Diastereomer is (S)-2-ethylbutyl 2-(((R)-((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate:

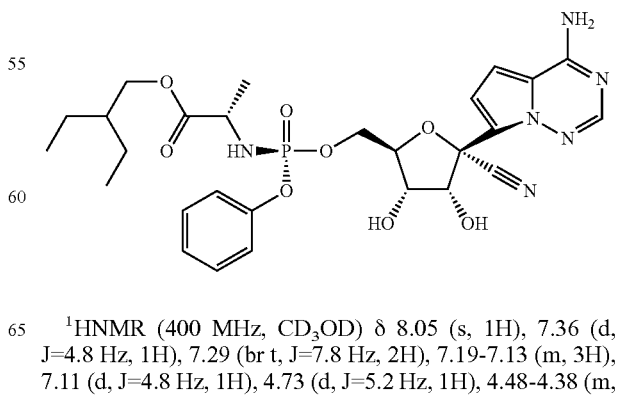

$^1$HNMR (400 MHz, CD$_3$OD) δ 8.05 (s, 1H), 7.36 (d, J=4.8 Hz, 1H), 7.29 (br t, J=7.8 Hz, 2H), 7.19-7.13 (m, 3H), 7.11 (d, J=4.8 Hz, 1H), 4.73 (d, J=5.2 Hz, 1H), 4.48-4.38 (m,

2H), 4.37-4.28 (m, 1H), 4.17 (t, J=5.6 Hz, 1H), 4.08-3.94 (m, 2H), 3.94-3.80 (m, 1H), 1.48 (sep, J=12.0, 6.1 Hz, 1H), 1.34 (p, J=7.3 Hz, 4H), 1.29 (d, J=7.2 Hz, 3H), 0.87 (t, J=7.4 Hz, 6H). $^{31}$PNMR (162 MHz, CD$_3$OD) δ 3.71 (s). HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.585 min.

Second Eluting Diastereomer is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate:

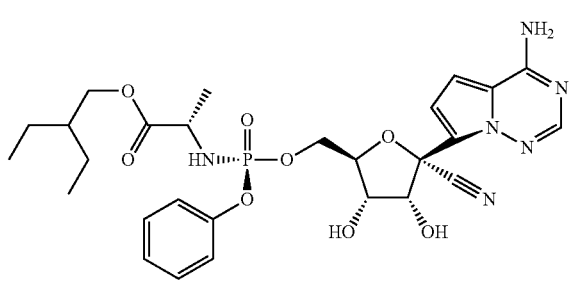 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

$^1$HNMR (400 MHz, CD$_3$OD) δ 8.08 (s, 1H), 7.36-7.28 (m, 3H), 7.23-7.14 (m, 3H), 7.08 (d, J=4.8 Hz, 1H), 4.71 (d, J=5.3 Hz, 1H), 4.45-4.34 (m, 2H), 4.32-4.24 (m, 1H), 4.14 (t, J=5.8 Hz, 1H), 4.08-3.94 (m, 2H), 3.93-3.85 (m, 1H), 1.47 (sep, J=6.2 Hz, 1H), 1.38-1.26 (m, 7H), 0.87 (t, J=7.5 Hz, 6H). $^{31}$PNMR (162 MHz, CD$_3$OD) δ 3.73 (s). HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) t$_R$=5.629 min.

Example 13

(2S)-ethyl 2-((a2R,3S,4R,5R)-5-(4-aminopyrrolo[1,2-f][1,2,4]triazin-7-yl)-5-cyano-3,4-dihydroxytetrahydrofuran-2-yl)methoxy)(phenoxy)phosphorylamino) propanoate (Compound 10)

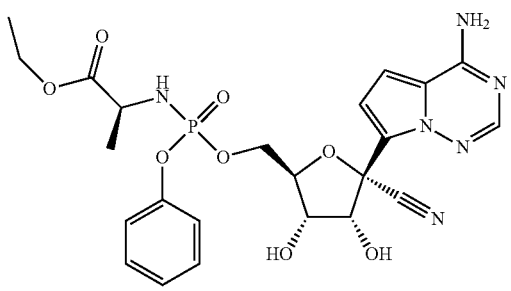 [SMILES: CCOC(=O)[C@H](C)NP(=O)(OC[C@H]1O[C@@](C#N)(c2ccc3c(N)ncnn23)[C@H](O)[C@@H]1O)Oc1ccccc1]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Procedure 1. Preparation via Chloridate A

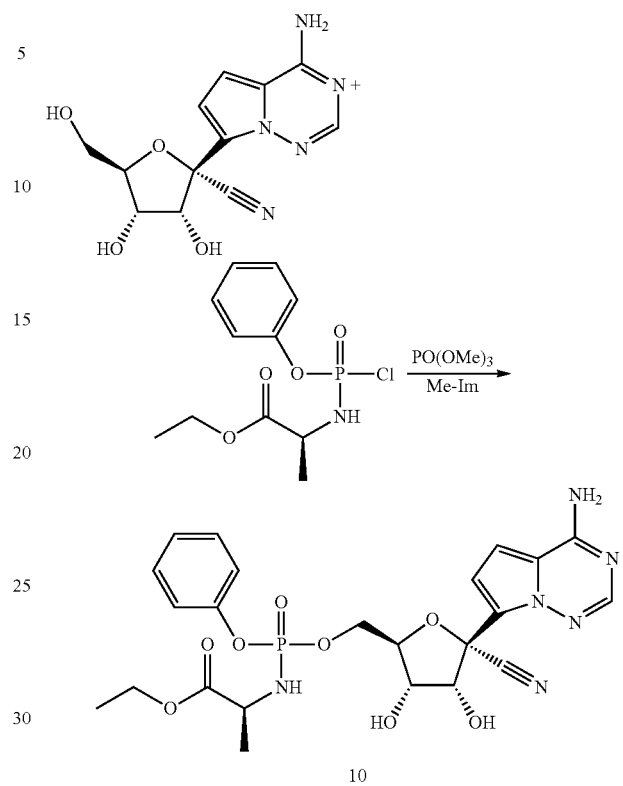

Prepared from Compound 1 and chloridate A using same method as for the preparation of compound 8. $^1$H NMR (300 MHz, CD$_3$OD) δ 7.95 (m, 1H), 7.32-6.97 (m, 7H), 4.78 (m, 1H), 4.43-4.08 (m, 6H), 3.83 (m, 1H), 1.31-1.18 (m, 6H). $^{31}$P NMR (121.4 MHz, CD$_3$OD) δ 3.7. LCMS m/z 547.0 [M+H], 545.0 [M−H].

Procedure 2. Preparation Via Nitro-Benzene Compound L

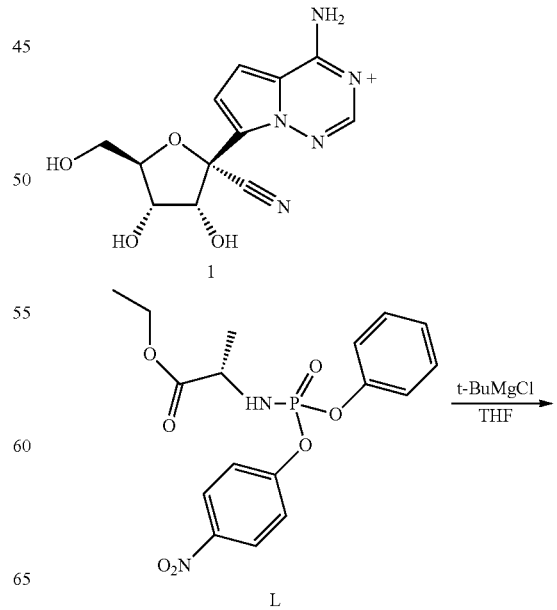

-continued

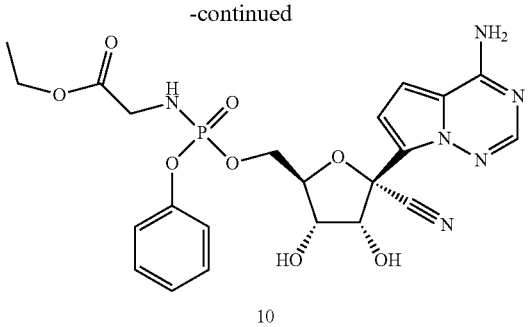

10

Compound 1 (50 mg, 0.17 mmol) was dissolved in NMP-THF (1:1 mL)) and cooled with ice bath. tBuMgCl (0.257 mL, 0.257 mmol) was then added over about 5 min. The resulting mixture was allowed to warm to RT and was stirred for about 30 min. Then a solution of compound L (Prepared according to US20120009147, 74.6 mg, 0.189 mmol) in THF (2 mL) was added. After about 30 min, the reaction mixture was purified by HPLC (acetonitrile 10 to 80% in water) to give compound 29 as a yellow solid. The solid was further purified with silica gel chromatography (MeOH 0 to 20% DCM) to afford compound 29. $^1$H NMR (400 MHz, CD$_3$OD) δ 7.76 (d, J=6.0 Hz, 1H), 7.25-7.14 (m, 2H), 7.11-6.99 (m, 3H), 6.87-6.72 (m, 2H), 4.70 (d, J=5.4 Hz, 1H), 4.39-4.24 (m, 2H), 4.20 (dddd, J=9.7, 7.9, 5.1, 2.8 Hz, 1H), 4.10 (dt, J=12.8, 5.5 Hz, 1H), 4.06-3.91 (m, 2H), 3.72 (ddq, J=14.3, 9.3, 7.1 Hz, 1H), 1.17 (dd, J=7.1, 1.0 Hz, 1H), 1.14-1.06 (m, 5H). $^{31}$P NMR (162 MHz, CD$_3$OD) δ 3.73, 3.68. MS m/z=547 (M+1)$^+$.

Example 15

(2S,2'S)-diethyl 2,2'-((a2R,3S,4R,5R)-5-(4-aminopyrrolo[1,2-][1,2,4]triazin-7-yl)-5-cyano-3,4-dihydroxytetrahydrofuran-2-yl)methoxy)phosphoryl)bis(azanediyl) dipropanoate (Compound 12)

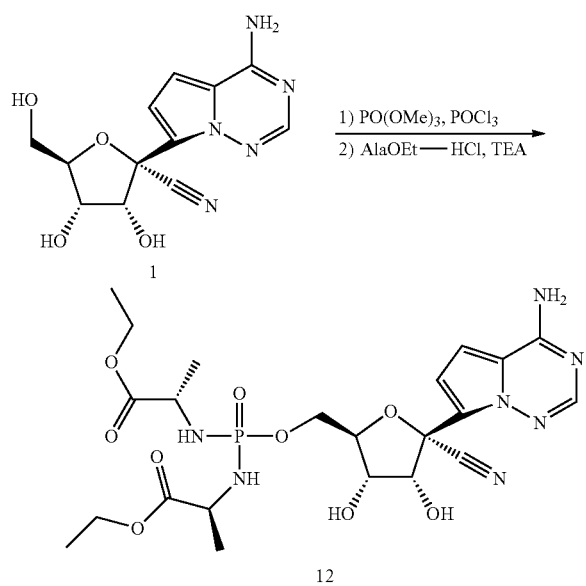

The nucleoside 1 (14.6 mg, 0.05 mmol) was dissolved in anhydrous trimethyl phosphate (0.5 mL) and stirred under N$_2$(g) at RT. POCl$_3$ (9.2 µL, 0.1 mmol) was added and the mixture stirred for about 60 min. Alanine ethyl ester hydrochloride (61 mg, 0.4 mmol) and then Et$_3$N (70 µL, 0.5 mmol) was added. The resultant mixture was stirred for about 15 min. and then additional Et$_3$N (70 µl, 0.5 mmol) was added to give a solution pH of 9-10. The mixture was stirred for about 2 h. and then diluted with EtOAc, washed with saturated aqueous NaHCO$_3$ solution followed by saturated aqueous NaCl solution. The organic layer was dried over anhydrous Na$_2$SO$_4$ and concentrated under reduced pressure. The residue was subjected to preparative HPLC (C$_{18}$ column) to yield the product 12. $^1$H NMR (400 MHz, CD$_3$OD) δ 8.13 (s, 1H), 7.41 (d, J=4.8 Hz, 1H), 7.18 (d, J=4.8 Hz, 1H), 4.78 (d, J=5.6 Hz, 1H), 4.36 (m, 1H), 4.25-4.08 (m, 7H), 3.83 (m, 2H), 1.33-1.23 (m, 12H). $^{31}$P NMR (121.4 MHz, CD$_3$OD) δ 13.8. LCMS m/z 570.0 [M+H], 568.0 [M−H].

Example 18

S,S'-2,2'-((((2R,3S,4R,5R)-5-(4-aminopyrrolo[1,2-f][1,2,4]triazin-7-yl)-5-cyano-3,4-dihydroxytetrahydrofuran-2-yl)methoxy)phosphoryl)bis(oxy)bis(ethane-2,1-diyl) bis(2,2-dimethylpropanethioate) (Compound 15)

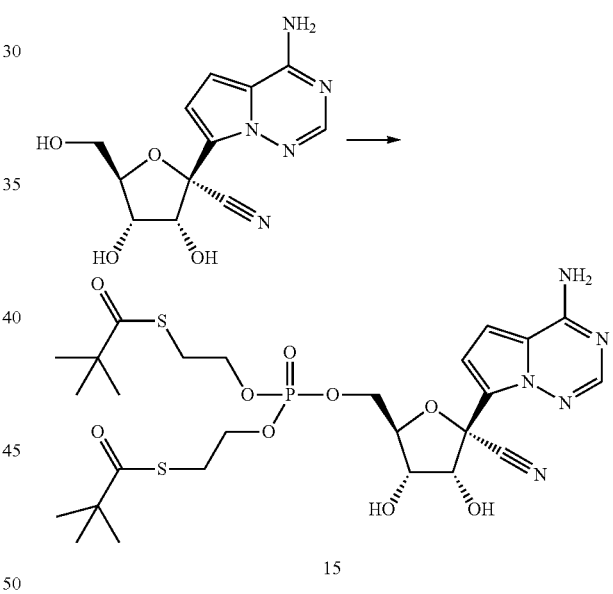

The nucleoside 1 (0.028 g, 0.096 mmol) was dissolved in trimethylphosphate (1 mL). The reaction was stirred under N$_2$(g) and then treated with 1H-tetrazole (0.021 g, 0.29 mmol). The reaction mixture was cooled to 0° C. and the phosphane (Nucleoside Nucleotides, Nucleic acids; 14; 3-5; 1995; 763-766. Lefebvre, Isabelle; Pompon, Alain; Perigaud, Christian; Girardet, Jean-Luc; Gosselin, Gilles; et al.) (87 mg, 0.192 mmol) was added. The reaction was stirred for 2 h. and then quenched with 30% hydrogen peroxide (0.120 mL). The mixture was stirred for 30 min at RT and then treated with saturated aqueous sodium thiosulfate (1 mL). The mixture was stirred for 10 min. and then concentrated under reduced pressure. The residue was subjected to preparative HPLC to isolate the title product 15. $^1$H NMR (300 MHz, CD$_3$CN) δ7.98 (s, 1H), 6.92 (d, 1H), 6.81 (d, 1H), 6.44 (bs, 2H), 4.82 (m, 2H), 4.47 (m, 1H), 4.24 (m, 2H), 4.00

(m, 4H), 3.80 (bs, 1H), 3.11 (m, 4H), 1.24 (s, 9H). $^{31}$P NMR (121.4 MHz, CD$_3$CN) δ −1.85 (s). LCMS m/z 661 [M+H].

Example 20

((2R,3S,4R,5R)-5-(4-aminopyrrolo[1,2-f][1,2,4]triazin-7-yl)-5-cyano-3,4-dihydroxytetrahydrofuran-2-yl)methyl tetrahydrogen triphosphate (Compound 17)

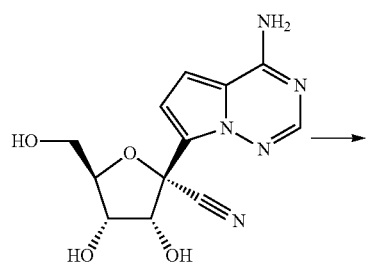

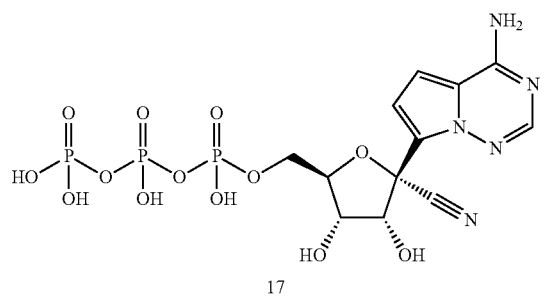

17

Compound 17 was prepared from compound 1 using a similar procedure as previously described (WO2012012776). The product was isolated as the sodium salt. $^1$H NMR (400 MHz, D$_2$O) δ 7.76 (s, 1H), 6.88 (d, J=4.8 Hz, 1H), 6.73 (d, J=4.4 Hz, 1H), 4.86 (d, J=5.2 Hz, 1H), 4.43 (m, 1H), 4.39 (m, 1H), 4.05 (m, 1H), 3.94 (m, 1H). $^{31}$P NMR (121.4 MHz, D$_2$O) δ −5.4 (d, 1P), −10.8 (d, 1P), −21.1 (t, 1P). LCMS m/z 530 [M−H], 531.9 [M+H] Tr=0.22 min. HPLC ion exchange Tr=9.95 min.

Example 20 a. a2R,3S,4R,5R)-5-(4-aminopyrrolo[2,1-f][1,2,4]triazin-7-yl)-5-cyano-3,4-dihydroxytetrahydrofuran-2-yl)methyl phosphate (Compound 33)

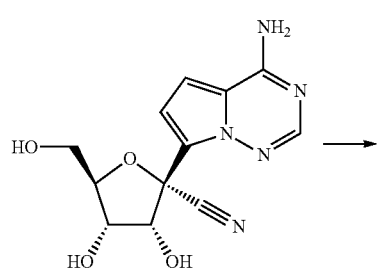

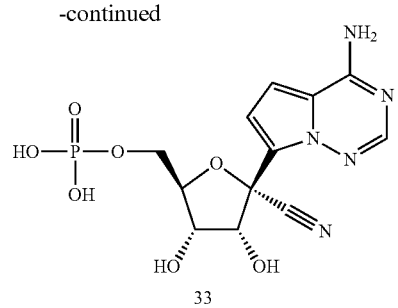

33

A mixture of about 0.05 mmol of compound 1 and about 0.5 mL of trimethylphosphate was sealed in a container for about one to about 48 h. The mixture was cooled to about −10 to about 10° C. and about 0.075 mmol of phosphorus oxychloride is added. After about one to about 24 hours, the reaction was quenched with about 0.5 mL of 1M tetraethylammonium bircarbonate and the desired fractions were isolated by anion exchange chromatography to afford the title compound.

Compound 33 was prepared as the bis-triethylammonium salt from compound 1 as previously described (WO2011150288). $^1$H NMR (400 MHz, D$_2$O) δ 7.82 (s, 1H), 6.91-6.88 (m, 1H), 6.81-6.78 (m, 1H), 4.87-4.84 (m, 1H), 4.40-4.30 (m, 2H), 3.95-3.77 (m, 2H), 3.10-3.00 (m, 6H), 1.20-1.10 (m, 9H). $^{31}$P NMR (162 MHz, D$_2$O) δ 2.33. MS m/z 371.

Example 20 b. a2R,3S,4R,5R)-5-(4-aminopyrrolo[2,1-f][1,2,4]triazin-7-yl)-5-cyano-3,4-dihydroxytetrahydrofuran-2-yl)methyl trihydrogen diphosphate (Compound 34)

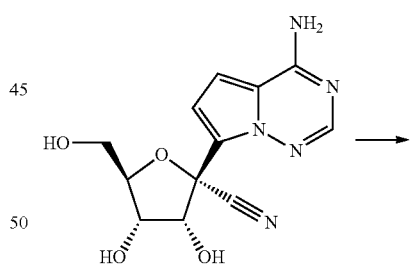

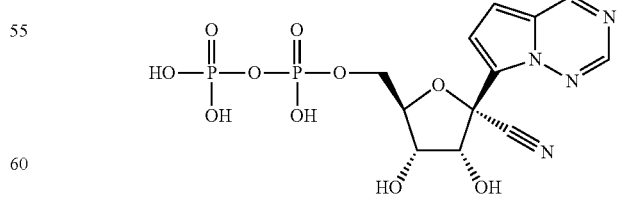

34

Compound 34 was prepared as the tri-lithium salt from compound 1 as previously described (WO2002057425). $^{31}$P NMR (162 MHz, D$_2$O) δ −5.34 (d), −9.75 (d). MS m/z 451.

Example 24

(2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (21)

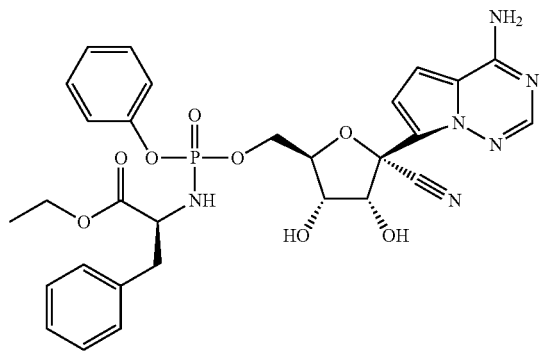 [SMILES: CCOC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate is described below.

Preparation of (S)-ethyl 2-amino-3-phenylpropanoate hydrochloride

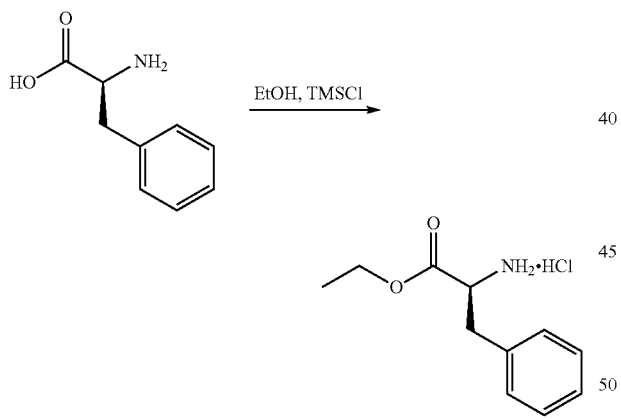

L-Phenylalanine (5 g, 30 mmol) was taken up in EtOH (30 mL). TMSCl (6.915 mL, 54 mmol) was added to the reaction at RT. The reaction vessel was fitted with a reflux condenser and the reaction was placed in an 80° C. bath. The reaction was stirred overnight. The next day the reaction was cooled to RT, concentrated under reduced pressure and the resulting residue was taken up in Et$_2$O. The resulting slurry was filtered and the isolate solids were further washed with Et$_2$O. The washed solids were placed under high vacuum to yield example (S)-ethyl 2-amino-3-phenylpropanoate hydrochloride. $^1$H NMR (400 MHz, DMSO-d$_6$) δ 8.52 (s, 3H), 7.30 (m, 5H), 4.24 (AB$\underline{X}$, J$_{AX}$=7.8 Hz, J$_{BX}$=6.2 Hz, 1H), 4.11 (m, 2H), 3.17, 3.05 (A$\underline{B}$X, J$_{AB}$=−14 Hz, J$_{BX}$=5.8 Hz, J$_{AX}$=7.6 Hz, 2H), 1.09 (t, J=6.8 Hz, 3H).

Preparation of (2S)-ethyl 2-(((4-nitrophenoxy)(phenoxy)phosphoryl)amino)-3-phenylpropanoate (Compound D)

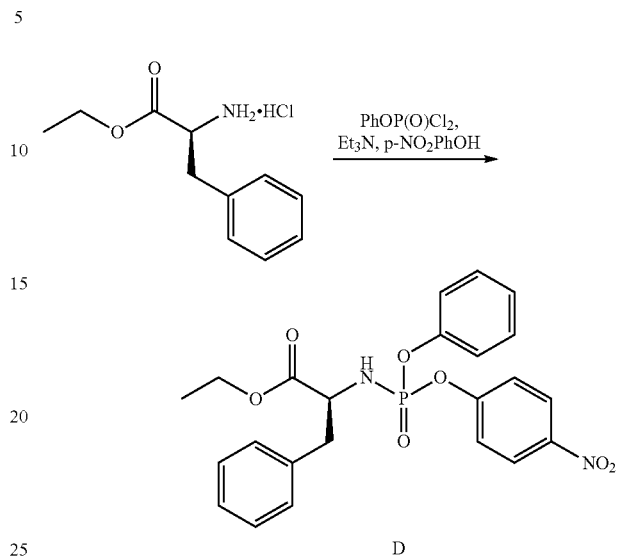

(S)-ethyl 2-amino-3-phenylpropanoate hydrochloride (1.01 g, 4.41 mmol) was dissolved in DCM (50 mL). This solution was cooled to about 0° C. and PhOP(O)Cl$_2$ (0.656 mL, 4.41 mmol) was added, followed by the slow addition of Et$_3$N (1.62 mL, 11.5 mmol) over 5 min. The cold bath was removed and the reaction was allowed to warm to RT and stir over a period of 80 min. p-NO$_2$PhOH (0.583 g, 4.19 mmol) was added, followed by more Et$_3$N (0.3 mL, 2.1 mmol). The reaction progress was monitored by LC/MS. Upon completion of the reaction, it was diluted with Et$_2$O, and the resulting solids were removed by filtration. The filtrate was concentrated and compound D was isolated by silica gel column chromatography (25 g dry load cartridge, 120 g column; eluent: 100% hexanes ramping to 55% EtOAc in hexanes). $^1$H NMR (400 MHz, CD$_3$OD) δ 8.17 (m, 2H), 7.33 (m, 2H), 7.09-7.25 (m, 10H), 4.17 (m, 1H), 4.07 (m, 2H), 3.08 (m, 1H), 2.84 (m, 1H), 1.14 (m, 3H). $^{31}$P NMR (162 MHz, DMSO-d$_6$) δ −1.479 (s), −1.719 (s). MS m/z=471.01 [M+1].

Preparation of (2S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (Compound 21)

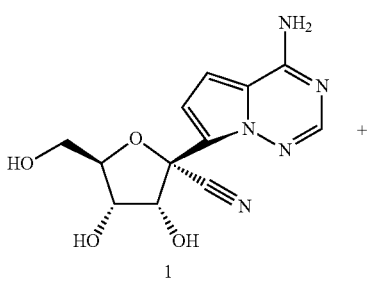

1

+

-continued

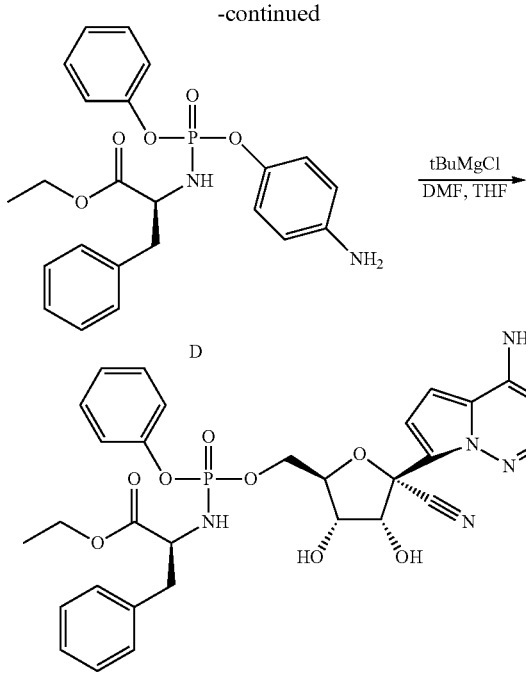

Compound 1 (0.030 g, 0.103 mmol) was dissolved in DMF (1 mL) and then THF (0.5 mL) was added. t-BuMgCl (1M/THF, 154.5 μL, 0.154 μmol) was added to the reaction in a drop-wise manner with vigorous stirring. The resulting white slurry was stirred at RT for about 30 min. A solution of compound D (0.058 g, 0.124 mmol) in THF (1 mL) was added in a drop-wise manner to the reaction at RT. The reaction progress was monitored by LC/MS. When the reaction progressed to 50% conversion, the reaction was cooled in an ice bath and quenched with glacial acetic acid (70 μL). The reaction was concentrated and compound 21 was isolated from the residue by reverse phase HPLC. $^1$H NMR (400 MHz, DMSO-$d_6$) δ 7.91 (d, J=4 Hz, 1H), 7.90 (brs, 2H), 7.09-7.30 (m, 8H), 7.01, (t, J=8.2 Hz, 2H), 6.89 (d, J=4.4 Hz, 1H), 6.82 (t, J=4.4 Hz, 1H), 6.27 (m, 1H), 6.14 (m, 1H), 5.34 (m, 1H), 4.62 (t, J=5.6 Hz, 1H), 4.15 (m, 1H), 3.78-4.01 (m, 6H), 2.92 (m, 1H), 2.78 (m, 1H), 1.04 (m, 3H). $^{31}$P NMR (162 MHz, DMSO-$d_6$) δ 3.69 (s), 3.34 (s). MS m/z=623.0 [M+H].

Example 25

(2S)-ethyl 2-((((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate (22)

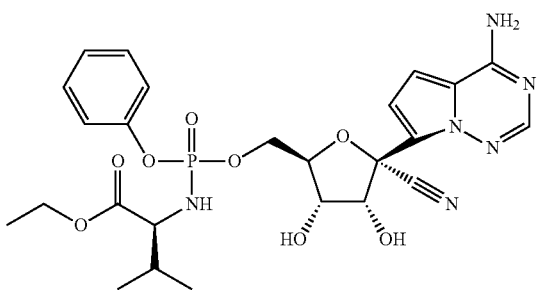 [SMILES: CCOC(=O)[C@@H](NP(=O)(OC[C@H]1O[C@@](C#N)(c2ccc3c(N)ncnn23)[C@H](O)[C@@H]1O)Oc1ccccc1)C(C)C]

The preparation of (2S)-ethyl 2-((((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate is described below.

Preparation of (2S)-ethyl 3-methyl-2-(((4-nitrophenoxy)(phenoxy)phosphoryl)amino) butanoate (Compound E)

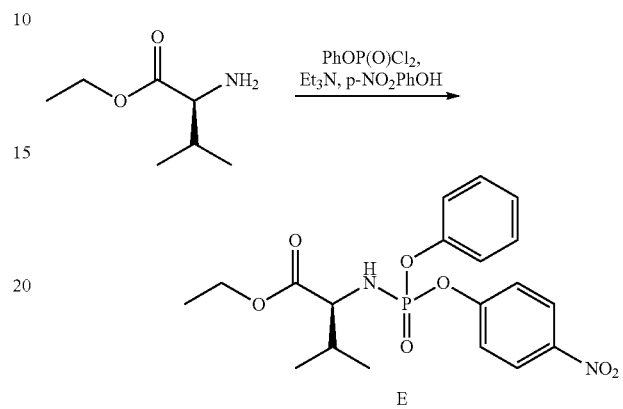

The (S)-ethyl 2-amino-3-methylbutanoate (0.351 g, 1.932 mmol) was dissolved in DCM (17 mL). This solution was cooled in an ice bath and PhOP(O)Cl$_2$ (0.287 mL, 1.932 mmol) was added, followed by the slow addition of Et$_3$N (1.62 mL, 11.4 mmol) over about 5 min. The cold bath was removed and the reaction was allowed to warm to RT and stir over a period of 1 h. p-NO$_2$PhOH (0.255 g, 1.836 mmol) was added, and the reaction progress was monitored by LC/MS. Upon completion of the reaction, the mixture was diluted with Et$_2$O, and the resulting solids were removed by filtration. The filtrate was concentrated and compound E was isolated by silica gel column chromatography (12 g dry load cartridge, 80 g column; eluent: 100% hexanes ramping to 55% EtOAc in hexanes). $^1$H NMR (400 MHz, DMSO-$d_6$) δ 8.30 (d, J=9.2 Hz, 2H), 7.48 (t, J=9.6 Hz, 2H), 7.40 (t, J=7.8 Hz, 2H), 7.20-7.27 (m, 3H), 6.60 (quart, J=11.6 Hz, 1H), 4.01 (m, 2H), 3.61 (m, 1H), 1.93 (m, 1H), 1.11 (m, 3H), 0.79 (m, 6H). $^{31}$P NMR (162 MHz, DMSO-$d_6$) δ −0.342 (s), −0.578 (s). MS m/z=422.9 [M+H].

Preparation of (2 S)-ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-methylbutanoate (Compound 22)

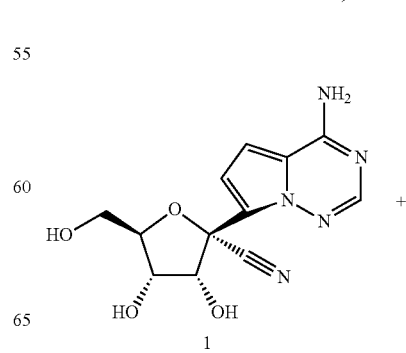

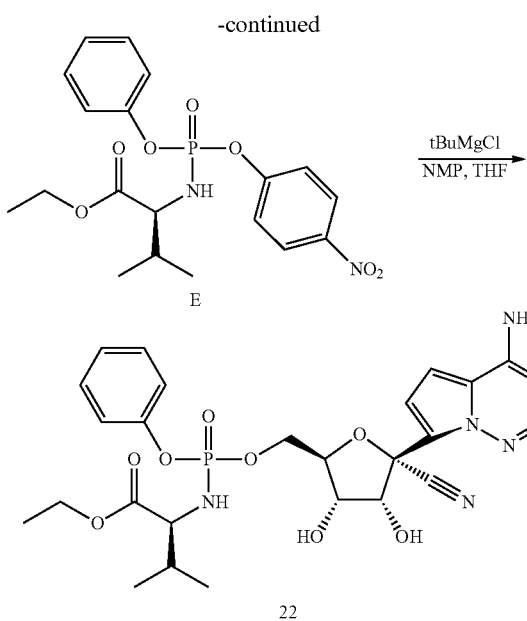

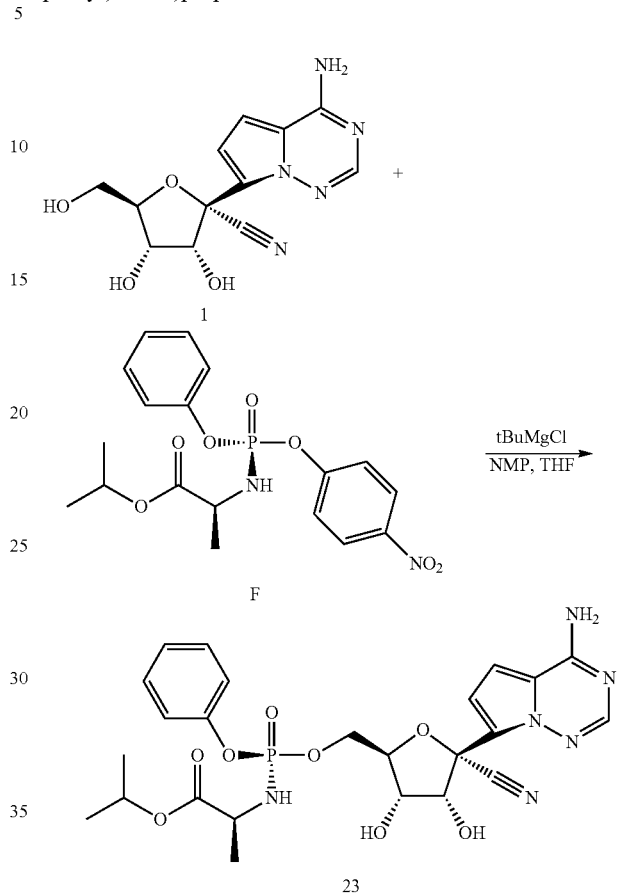

Compound 1 (0.040 g, 0.137 mmol) was dissolved in NMP (1.5 mL) and then THF (0.25 mL) was added. This solution was cooled in an ice bath and t-BuMgCl (1M/THF, 425.7 µL, 0.426 µmol) was added in a drop-wise manner with vigorous stirring. The ice bath was removed and the resulting white slurry was stirred at RT for about 15 min. A solution of compound E (0.081 g, 0.192 mmol) in THF (0.5 mL) was added in a drop-wise manner to the reaction at RT. The reaction progress was monitored by LC/MS. When the reaction progressed to 50% conversion, the reaction was cooled in an ice bath and quenched with glacial acetic acid (70 µL). The reaction was concentrated and compound 22 was semi-purified from the residue by reverse phase HPLC. The semi-pure material was further purified by silica gel column chromatography (12 g dry load cartridge, 40 g column; eluent: 100% EtOAc ramping to 10% MeOH in EtOAc) to yield compound 22. $^1$H NMR (400 MHz, DMSO-d$_6$) δ 7.91 (d, J=1.6 Hz, 1H), 7.88 (brs, 2H), 7.32 (m, 2H), 7.15 (m, 3H), 6.90 (t, J=4.2 Hz, 1H), 6.84 (d, J=4.8 Hz, 1H), 6.26 (dd, J=13.4, 6.2 Hz, 1H), 5.87 (quart. J=11.2 Hz, 1H), 5.35 (m, 1H), 4.64 (m, 1H), 4.25 (m, 2H), 3.93-4.15 (m, 4H), 3.45 (m, 1H), 1.87 (m, 1H), 1.09-1.16 (m, 3H), 0.70-0.83 (m, 6H). $^{31}$P NMR (162 MHz, DMSO-d$_6$) δ 4.59 (s), 4.47 (s). MS m/z=575.02 [M+H].

Example 26

(S)-isopropyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)propanoate (23)

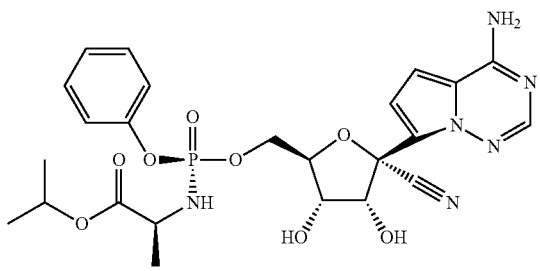 [SMILES: CC(C)OC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-isopropyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate is described below.

Compound 1 (60.0 mg, 206 µmol) was dissolved in NMP (0.28 mL). THF (0.2 mL) was added followed by tert-butyl magnesium chloride (1.0M solution in tetrahydrofuran, 0.309 mL) at RT under an argon atmosphere. After 20 min, a solution of compound F (Prepared according to Cho, A. et al *J. Med. Chem.* 2014, 57, 1812-1825., 81 mg, 206 µmol) in THF (0.2 mL) was added, and the resulting mixture was warmed to about 50° C. After 3 h, the reaction mixture was allowed to cool to RT and was purified directly by preparatory HPLC (Phenominex Synergi 4u Hydro-RR 80 Å 150×30 mm column, 5-100% acetonitrile/water gradient) to afford compound 23. $^1$H NMR (400 MHz, CD$_3$OD) δ 7.86 (s, 1H), 7.34-7.26 (m, 2H), 7.21-7.12 (m, 3H), 6.91 (d, J=4.6 Hz, 1H), 6.87 (d, J=4.6 Hz, 1H), 4.92 (sept, J=6.3 Hz, 1H), 4.80 (d, J=5.4 Hz, 1H), 4.43-4.34 (m, 1H), 4.33-4.24 (m, 1H), 4.18 (t, J=5.6 Hz, 1H), 3.82 (dq, J=9.7, 7.1 Hz, 2H), 1.27 (dd, J=7.1, 1.0 Hz, 3H), 1.18 (dd, J=6.3, 4.8 Hz, 6H). $^{31}$P NMR (162 MHz, CD$_3$OD) δ 3.72 (s). LC/MS: t$_R$=1.39 min, MS m/z=561.11 [M+H]; LC system: Thermo Accela 1250 UHPLC; MS system: Thermo LCQ Fleet; Column: Kinetex 2.6µ. XB—C18 100A, 50×4.6 mm; Solvents: ACN with 0.1% acetic acid, water with 0.1% acetic acid; Gradient: 0 min-2.0 min 2-100% ACN, 2.0 min-3.05 min 100% ACN, 3.05 min-3.2 min 100%-2% ACN, 3.2 min-3.5 min 2% ACN at 2 µl/min. HPLC: t$_R$=2.523 min; HPLC system: Agilent 1100 series.; Column: Gemini 5 µC18 110A, 50×4.6

Example 27

(2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (24)

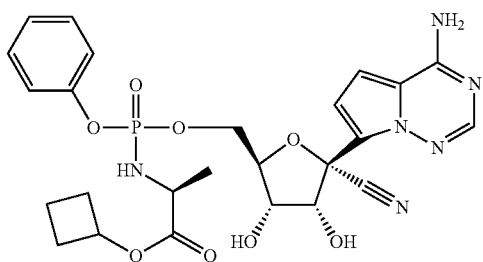 [SMILES: C[C@H](NP(=O)(OC[C@H]1O[C@@](C#N)(c2ccc3c(N)ncnn23)[C@H](O)[C@@H]1O)Oc1ccccc1)C(=O)OC1CCC1]

The preparation of (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

Preparation of (2S)-cyclobutyl 2-(((4-nitrophenoxy)(phenoxy)phosphoryl)amino)propanoate (Compound G)

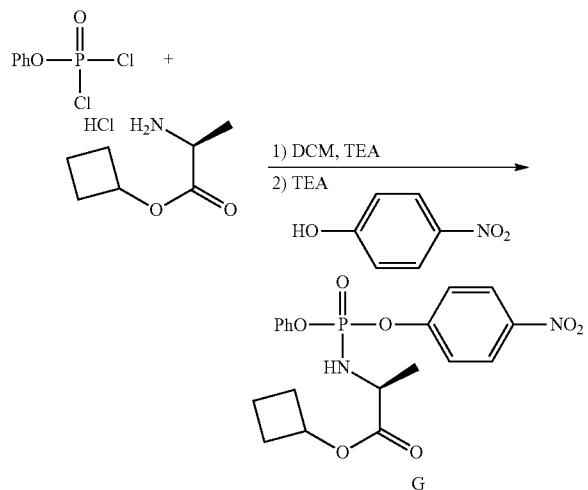

Phenyl dichlorophosphate (1.49 mL, 10 mmol) was dissolved in 10 mL of anhydrous DCM and stirred under atmosphere nitrogen in an ice bath. L-Alanine isobutyl ester hydrochloride (0.9 g, 5 mmol) was added in one portion. Triethylamine (765 µL, 5.5 mmol) was then added dropwise. Reaction stirred for about 1 h. More Triethylamine (765 µL, 5.5 mmol) was added dropwise and the reaction was stirred for about 45 min. p-Nitrophenol (1.25 g, 9 mmol) was added in one portion and stirred for about 30 min. Triethylamine (765 µL, 5.5 mmol) was added and the reaction mixture was stirred for about 2 h. Additional p-nitrophenol (1.25 g, 9 mmol) and triethylamine (765 µL, 5.5 mmol) were then added, and the reaction was stirred for another about 2 h. The reaction mixture was concentrated under reduced pressure. The resulting crude was diluted with EtOAc and washed twice with 5% aqueous citric acid solution, followed with saturated aqueous sodium chloride solution. The organic layer was then dried over anhydrous sodium sulfate and concentrated under reduced pressure. The crude residue was purified with silica gel column (0-20-50% EtOAc in hexanes) to give compound G. $^1$H NMR (400 MHz, CD$_3$OD) δ 8.33-8.23 (m, 2H), 7.52-7.33 (m, 4H), 7.33-7.17 (m, 3H), 4.96-4.85 (m, 1H), 4.07-3.96 (m, 1H), 2.27 (m, 2H), 2.07-1.91 (m, 2H), 1.83-1.70 (m, 1H), 1.70-1.55 (m, 1H), 1.32 (m, 3H). $^{31}$P NMR (162 MHz, CD$_3$OD) δ −1.36, −1.59. MS m/z=420.9 [M+H].

Preparation (2S)-cyclobutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate (Compound 24)

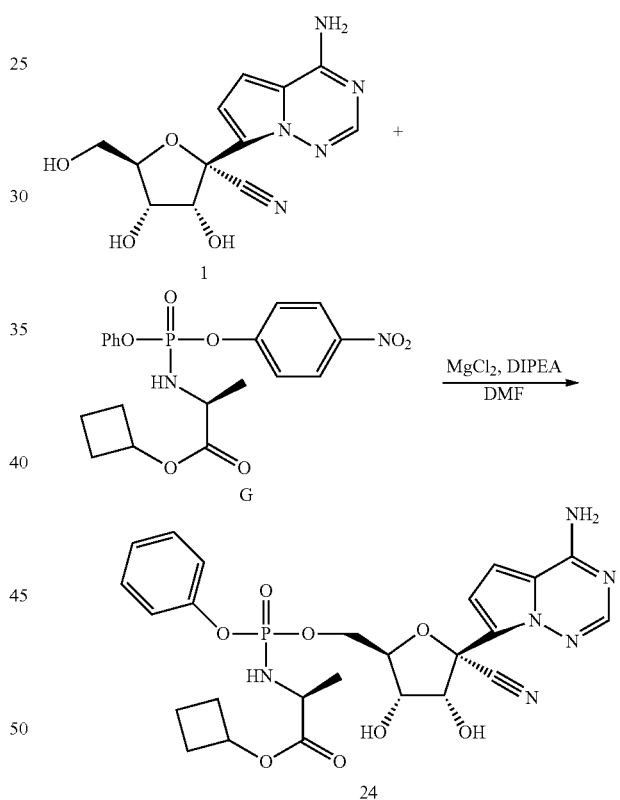

Compound 1 (58 mg, 0.2 mmol) was mixed with compound G (101 mg, 0.24 mmol) in 2 mL of anhydrous DMF. Magnesium chloride (42 mg, 0.44 mmol) was added in one portion. The reaction mixture was heated to about 50° C. DIPEA (87 µL, 0.5 mmol) was added, and the reaction was stirred for about 2 h at about 50° C. The reaction mixture was cooled to room temperature, was diluted with EtOAc and was washed with 5% aqueous citric acid solution followed by saturated aqueous sodium chloride solution. The organic layer was then dried over anhydrous sodium sulfate and concentrated under reduced pressure. The crude residue was purified with silica gel column (0-2-5% MeOH in DCM) to afford compound 24. $^1$H NMR (400 MHz, Methanol-d4) δ 7.85 (m, 1H), 7.34-7.22 (m, 2H), 7.22-7.08 (m, 3H), 6.94-6.84 (m, 2H), 4.95-4.85 (m, 1H), 4.79 (m, 1H), 4.46-4.34 (m, 2H), 4.34-4.24 (m, 1H), 4.19 (m, 1H), 3.81 (m, 1H), 2.27 (m, 2H), 2.01 (m, 2H), 1.84-1.68 (m, 1H), 1.62 (m, 1H), 1.30-1.16 (m, 3H). $^{31}$P NMR (162 MHz, cd$_3$od) δ 3.70, 3.65. MS m/z=573.0 [M+H].

Example 28

(2S)-isopropyl 2-(((a2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (25)

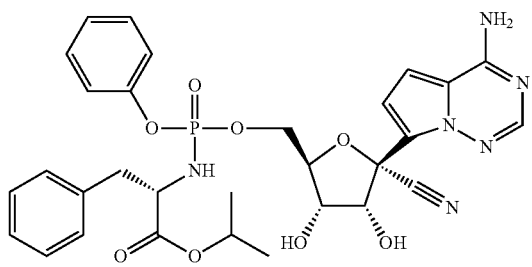 [SMILES: CC(C)OC(=O)[C@H](Cc1ccccc1)NP(=O)(OC[C@H]1O[C@@](C#N)(c2ccc3c(N)ncnn23)[C@H](O)[C@@H]1O)Oc1ccccc1]

The preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate is described below.

Preparation of (2S)-isopropyl 2-(((4-nitrophenoxy)(phenoxy)phosphoryl)amino)-3-phenylpropanoate (Compound H)

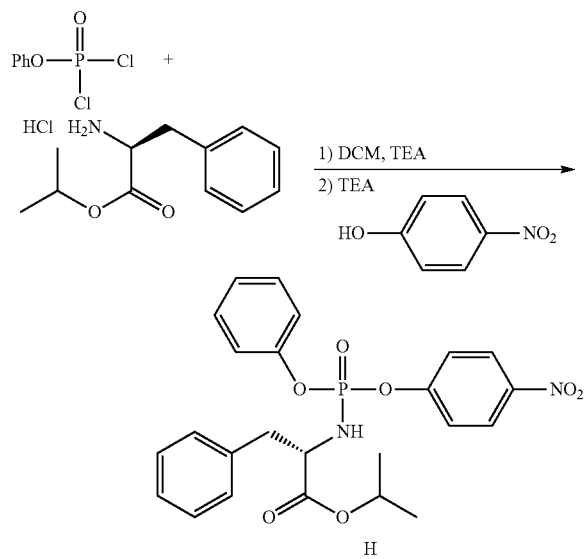

Phenyl dichlorophosphate (718 μL, 4.8 mmol) was dissolved in 10 mL of anhydrous DCM and stirred under a nitrogen atmosphere in an ice bath. L-Phenylalanine isopropyl ester hydrochloride (1 g, 4.1 mmol) was added in one portion. Another 10 mL of anhydrous DCM was added. Triethylamine (736 μL, 5.3 mmol) was added dropwise and the reaction mixture was stirred for about 30 min. More triethylamine (736 μL, 5.3 mmol) was then added dropwise and the reaction mixture was stirred for 30 min. Additional triethylamine (736 μL, 5.3 mmol) was then added dropwise and the reaction mixture was stirred for about 15 min. p-Nitrophenol (600 mg, 4.32 mmol) was then added. The ice bath was then removed and the reaction mixture was allowed to warm to room temperature and stirred for about 2 h. More p-nitrophenol (50 mg) and triethylamine (736 μL, 5.3 mmol) were the added and the reaction mixture was stirred for about 1 h.

The reaction mixture was then concentrated under reduced pressure, and was diluted with EtOAc and washed twice with 5% aqueous citric acid solution, followed with saturated aqueous sodium chloride solution. The organic layer was dried over anhydrous sodium sulfate and was concentrated under reduced pressure. The crude was purified with silica gel column (0-15% EtOAc in hexanes) to give compound H. $^1$H NMR (400 MHz, CDCl$_3$) δ 8.17 (m, 2H), 7.38-7.13 (m, 10H), 7.13-7.02 (m, 2H), 4.95 (m, 1H), 4.31 (m, 1H), 3.69 (m, 1H), 3.02 (dd, J=6.1, 1.8 Hz, 2H), 1.21-1.08 (m, 6H). $^{31}$P NMR (162 MHz, cdcl3) δ −2.96, −2.98. MS m/z=485.0 [M+H].

Preparation of (2S)-isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-3-phenylpropanoate (Compound 25)

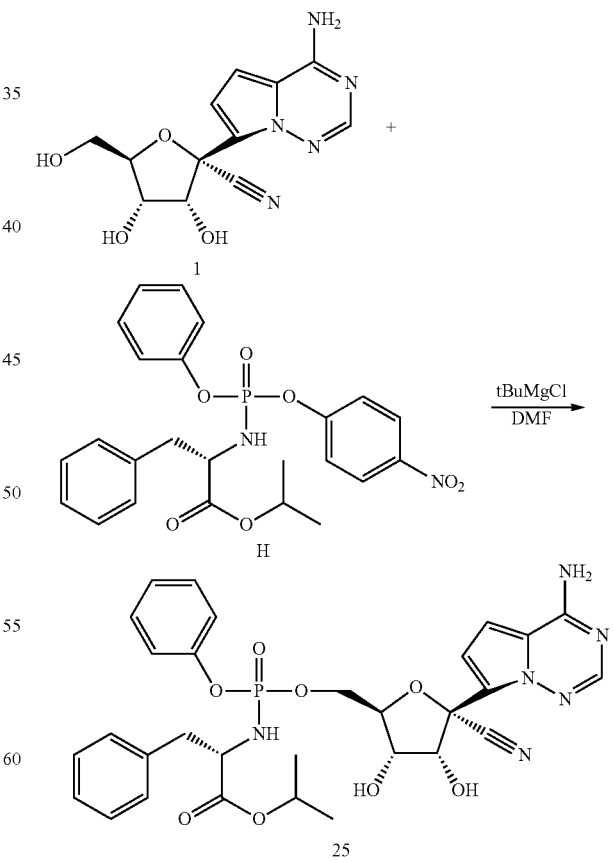

Compound 1 (58 mg, 0.2 mmol) and compound H (116 mg, 0.24 mmol) were mixed and 2 mL of anhydrous DMF was added. The reaction mixture was stirred under a nitrogen atmosphere at room temperature. 1M tBuMgCl in THF (300 μL, 0.3 mmol) was added dropwise over 3 minutes and the reaction mixture was then stirred for about 16 h. The reaction mixture was diluted with EtOAc and washed with 5% aqueous citric acid solution, saturated aqueous sodium bicarbonate solution and then saturated aqueous sodium chloride solution. The organic layer was dried over anhydrous sodium sulfate and concentrated under reduced pressure. The crude residue was purified with silica gel column (0-5% MeOH in DCM) to give compound 25.

$^1$H NMR (400 MHz, CD$_3$OD) δ 7.84 (m, 1H), 7.27-7.08 (m, 8H), 7.08-6.97 (m, 2H), 6.88 (m, 2H), 4.91-4.84 (m, 1H), 4.74 (m, 1H), 4.26 (m, 1H), 4.19-4.04 (m, 2H), 4.04-3.91 (m, 2H), 2.97 (m, 1H), 2.82 (m, 1H), 1.14 (m, 3H), 1.06 (m, 3H). $^{31}$P NMR (162 MHz, CD$_3$OD) δ 3.63, 3.25. MS m/z=637.0 [M+H].

Example 29

(S)-methyl 2-(((S)-(a2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (26)

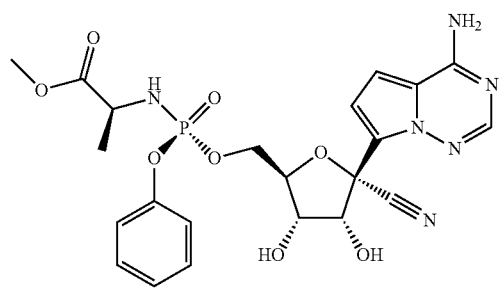 [SMILES: COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-methyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate is described below.

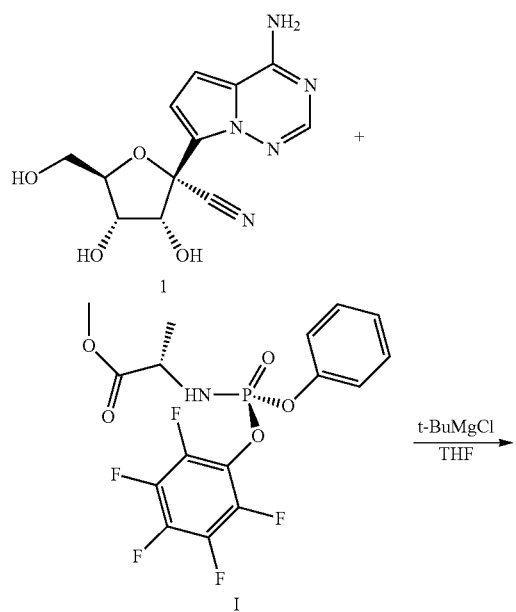

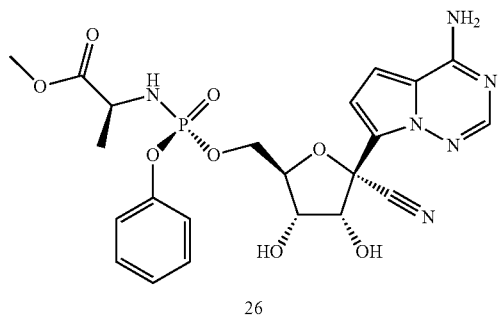

26

Compound 1 (100 mg, 0.34 mmol) was dissolved in THF (2 mL) and cooled with an ice water bath. Then 1M t-BuMgCl (0.52 mL, 0.77 mmol) was added dropwise slowly. The resulting mixture was stirred for about 30 min at room temperature. Then compound I (Prepared according to WO 2012142085, 219 mg, 0.52 mmol) in THF (2 mL) was added over 5 min and the resulting mixture was stirred for about 24 h at room temperature. The reaction mixture was then diluted with EtOAc, cooled under ice-water bath, washed with aq NaHCO$_3$ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give compound 26. $^1$H NMR (400 MHz, CD$_3$OD) δ 7.86 (s, 1H), 7.29 (dd, J=8.6, 7.2 Hz, 2H), 7.21-7.09 (m, 3H), 6.94-6.81 (m, 2H), 4.79 (d, J=5.4 Hz, 1H), 4.38 (ddq, J=10.8, 5.3, 2.7 Hz, 2H), 4.33-4.23 (m, 1H), 4.18 (t, J=5.5 Hz, 1H), 3.86 (dq, J=9.9, 7.1 Hz, 1H), 3.62 (s, 3H), 1.27 (dd, J=7.2, 1.1 Hz, 3H). MS m/z=533 (M+1)$^+$.

Example 30

(S)-neopentyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (27)

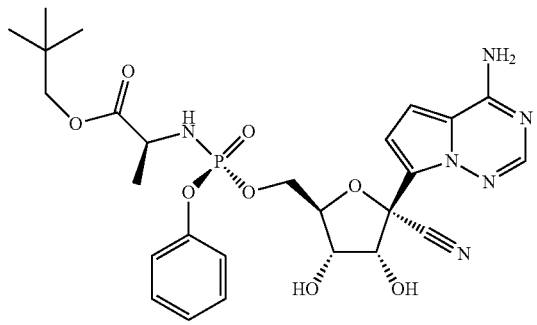 [SMILES: C[C@H](N[P@](=O)(OC[C@H]1O[C@@](C#N)(c2ccc3c(N)ncnn23)[C@H](O)[C@@H]1O)Oc1ccccc1)C(=O)OCC(C)(C)C]

The preparation of (S)-neopentyl 2-(((((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate is described below.

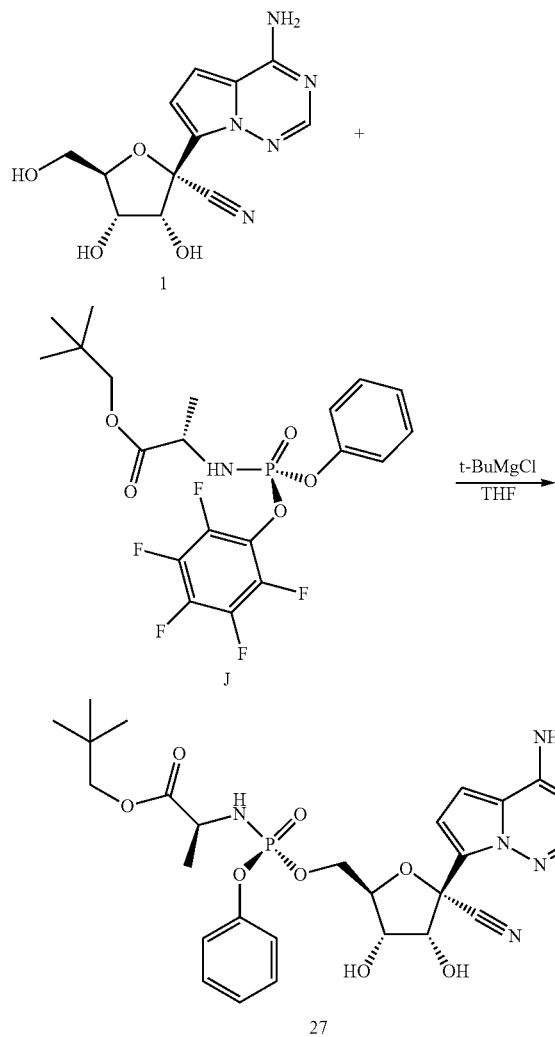

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for about 30 min at room temperature. Then compound J (Prepared according to WO2012075140, 248 mg, 0.52 mmol) was added over about 5 min and the resulting mixture was stirred for about 24 h at room temperature, diluted with EtOAc, cooled under ice-water bath, treated with aq NaHCO₃ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give Compound 27. $^1$H NMR (400 MHz, CD$_3$OD) δ 7.86 (s, 1H), 7.36-7.24 (m, 2H), 7.23-7.10 (m, 3H), 6.96-6.85 (m, 2H), 4.78 (d, J=5.4 Hz, 1H), 4.38 (tdd, J=10.0, 4.9, 2.5 Hz, 2H), 4.32-4.24 (m, 1H), 4.17 (t, J=5.6 Hz, 1H), 3.91 (dq, J=9.8, 7.1 Hz, 1H), 3.81 (d, J=10.5 Hz, 1H), 3.69 (d, J=10.5 Hz, 1H), 1.31 (dd, J=7.2, 1.1 Hz, 3H), 0.89 (s, 9H). MS m/z=589 (M+1)+.

Example 31

(2S)-cyclopentyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (28)

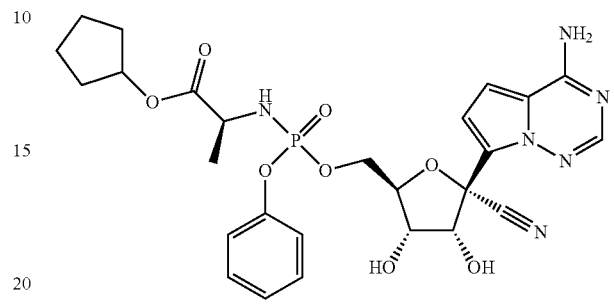

The preparation of (2S)-cyclopentyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate is described below.

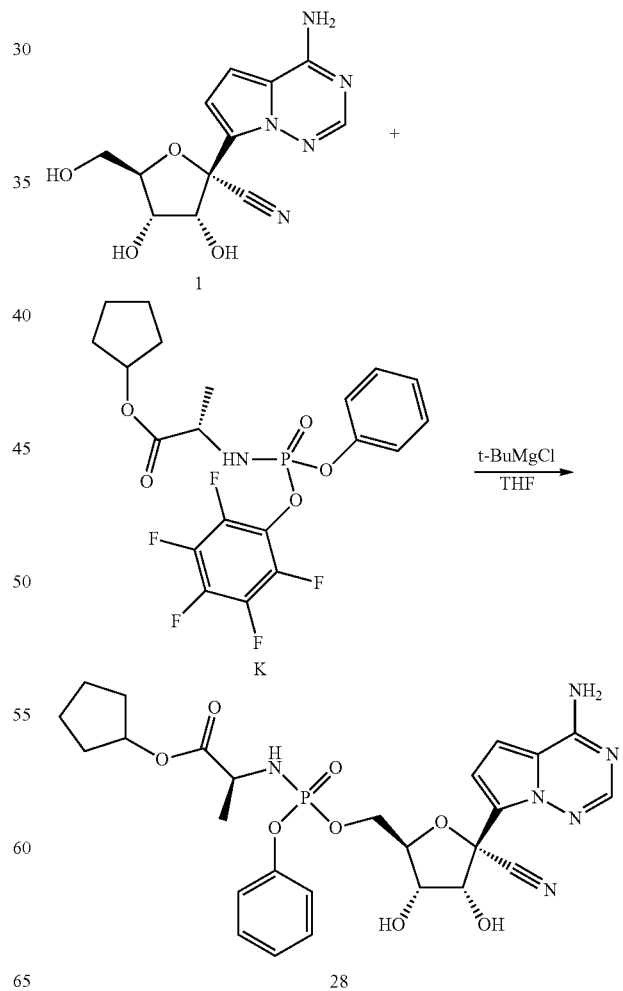

Compound 1 (100 mg, 0.34 mmol) was dissolved in THF (2 mL) and cooled under ice water bath. Then 1M t-BuMgCl (0.52 mL, 0.77 mmol) was added dropwise slowly. The resulting mixture was stirred for about 30 min at room temperature. Then compound K (Prepared according to WO2012075140, 247 mg, 0.52 mmol) in THF (2 mL) was added over about 5 min and the resulting mixture was stirred for about 24 h at room temperature, diluted with EtOAc, cooled under ice-water bath, treated with aq NaHCO₃ (2 mL), washed with brine, dried with sodium sulfate, and concentrated in vacuo. The resulting mixture was purified by silica gel column chromatography (MeOH 0 to 20% in DCM) and prep-HPLC (acetonitrile 10 to 80% in water) to give example 28. $^1$H NMR (400 MHz, CD$_3$OD) δ 7.85 (s, 1H), 7.33-7.22 (m, 2H), 7.14 (tdd, J=7.6, 2.1, 1.1 Hz, 3H), 6.95-6.87 (m, 2H), 5.13-5.00 (m, 1H), 4.78 (d, J=5.4 Hz, 1H), 4.48-4.35 (m, 2H), 4.30 (ddd, J=10.6, 5.7, 3.6 Hz, 1H), 4.19 (t, J=5.4 Hz, 1H), 3.78 (dq, J=9.2, 7.1 Hz, 1H), 1.81 (dtd, J=12.5, 5.9, 2.4 Hz, 2H), 1.74-1.49 (m, 6H), 1.21 (dd, J=7.1, 1.2 Hz, 3H). MS m/z=587 (M+1)⁺.

Example 32

(2S)-cyclohexyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (29)

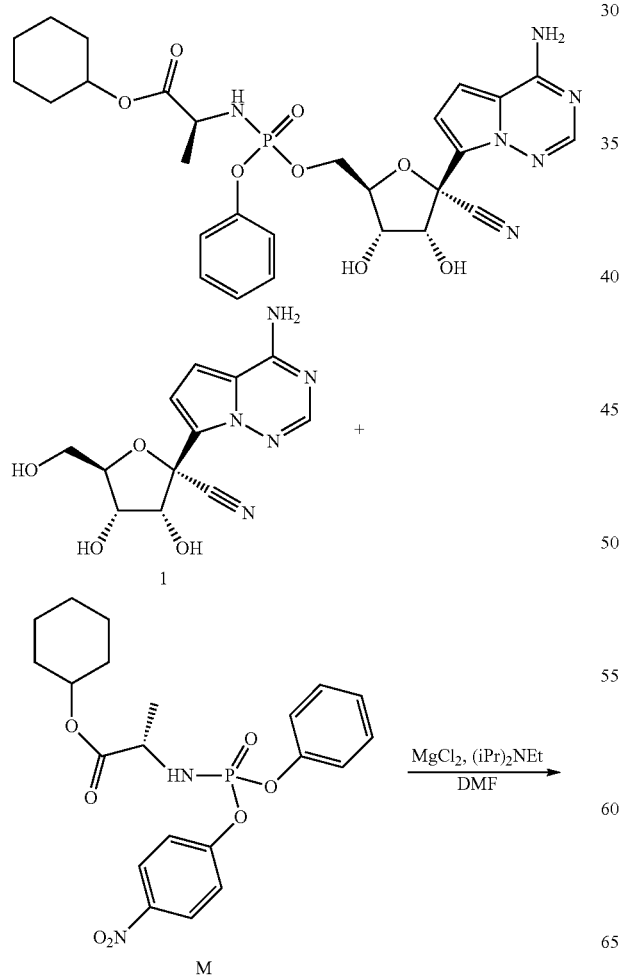

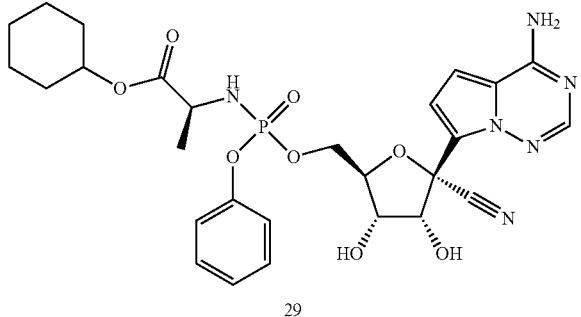

29

To a mixture of compound 1 (50 mg, 0.343 mmol), compound M (Prepared according to US20130143835, 93 mg, 0.209 mmol), and MgCl₂ (24.5 mg, 0.257 mmol) in DMF (1 mL) was added diisopropylethylamine (0.075 mL, 0.43 mmol) dropwise over about 5 min at about 0° C. The resulting mixture was stirred at about 50° C. for about 1 h. The reaction mixture was then cooled with an ice-water bath, treated with 1M citric acid (0.5 mL), and was purified directly by prep-HPLC (ACN 0 to 70% in water) to afford compound 29. $^1$H NMR (400 MHz, CD$_3$OD) δ 7.84 (s, 1H), 7.32-7.23 (m, 2H), 7.18-7.10 (m, 3H), 6.93-6.87 (m, 2H), 4.78 (d, J=5.4 Hz, 1H), 4.67 (td, J=8.7, 4.2 Hz, 1H), 4.48-4.35 (m, 2H), 4.30 (ddd, J=10.8, 5.7, 3.7 Hz, 1H), 4.20 (t, J=5.4 Hz, 1H), 3.88-3.71 (m, 1H), 1.83-1.63 (m, 4H), 1.58-1.46 (m, 1H), 1.46-1.24 (m, 5H), 1.24 (s, 3H). $^{31}$P NMR (162 MHz, CD$_3$OD) δ 3.75. MS m/z=601 (M+1)⁺.

Example 33

Ethyl 2-(((a2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (30)

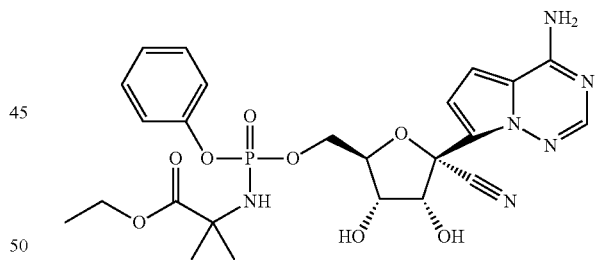

The preparation of ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Ethyl 2-((tert-butoxycarbonyl)amino)-2-methylpropanoate

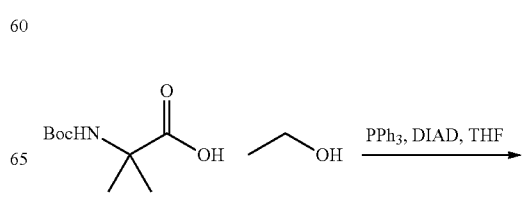

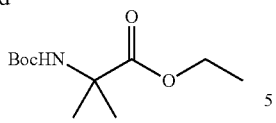

Take up triphenylphosphine (6.18 g, 25.00 mmol) in THF (30 mL). Next charge DIAD (4.92 mL, 25.00 mmol) and stir at room temperature for 10 min. Dissolve 2-((tert-butoxycarbonyl)amino)-2-methylpropanoic acid (5.08 g, 25.00 mmol) in THF (20 mL) and add to the reaction mixture followed by the addition of ethanol (2.19 mL, 37.49 mmol). Allow the reaction to stir at room temperature for about 1 h. The solvents were removed under reduced pressure and the crude was taken up in 1:1 Et$_2$O:Hexanes (120 mL). The solid triphenylphosphine oxide was filtered off and the solvent was removed under reduced pressure. The crude was taken up in minimal CH$_2$Cl$_2$ and purified by silica gel chromatography 0-50% EtOAc/Hex to afford ethyl 2-((tert-butoxycarbonyl)amino)-2-methylpropanoate. $^1$H NMR (400 MHz, Chloroform-d) δ 4.18 (q, J=7.1 Hz, 2H), 1.49 (s, 6H), 1.43 (s, 9H), 1.27 (t, J=7.1 Hz, 3H).

Preparation of Ethyl 2-amino-2-methylpropanoate hydrochloride

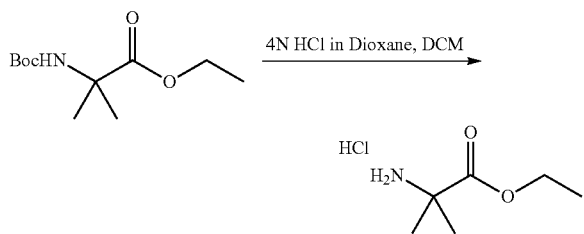

Take up ethyl 2-((tert-butoxycarbonyl)amino)-2-methylpropanoate (2.71 g, 11.72 mmol) in CH$_2$Cl$_2$ (25 mL) and slowly add 4N HCl in dioxane (25 mmol) and stir at room temperature. At 1 h, the reaction was determined to be complete by TLC. The solvents were removed under reduced pressure and the crude was coevaporated with Et$_2$O two times then placed under high vacuum to afford ethyl 2-amino-2-methylpropanoate hydrochloride. $^1$H NMR (400 MHz, DMSO-d$_6$) δ 8.70 (s, 3H), 4.18 (q, J=7.1 Hz, 2H), 1.46 (s, 6H), 1.21 (t, J=7.1 Hz, 3H).

Preparation of Ethyl 2-methyl-2-(((4-nitrophenoxy)(phenoxy)phosphoryl)amino)propanoate (Compound N)

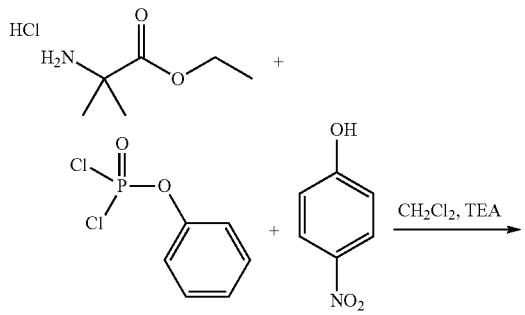

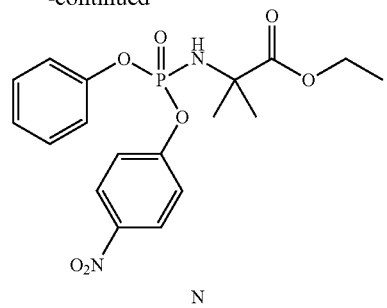

Take up phenyl dichlorophosphate (0.97 mL, 6.50 mmol) and ethyl 2-amino-2-methylpropanoate hydrochloride (1.09 g, 6.50 mmol) in CH$_2$Cl$_2$ (50 mL). Cool the reaction mixture to about 0° C. and slowly add TEA (1.75 mL, 12.45 mmol). Remove the cold bath and allow the reaction mixture to stir at room temperature. After about 2 h, the addition of the amino acid was determined to be complete by $^{31}$P NMR. Charge p-nitrophenol (0.860 g, 6.17 mmol) followed by the addition of TEA (0.87 g, 7.69 mmol). Allow the reaction to stir at room temperature. After about 2 h, the reaction was determined to be complete by LCMS. The reaction was diluted with Et$_2$O and the TEA.HCl salts were filtered off. The crude was concentrated and purified by silica gel chromatography (0-50% EtOAc/Hex) to afford compound N. $^1$H NMR (400 MHz, DMSO-d$_6$) δ 8.37-8.21 (m, 2H), 7.55-7.44 (m, 2H), 7.43-7.33 (m, 2H), 7.30-7.09 (m, 3H), 6.57 (d, J=10.1 Hz, 1H), 3.99 (q, J=7.1 Hz, 2H), 1.39 (s, 6H), 1.08 (t, J=7.1 Hz, 3H). $^{31}$P NMR (162 MHz, DMSO-d$_6$) δ −2.87. LC/MS: t$_R$=1.65 min, MS m/z=408.97 [M+1].; LC system: Thermo Accela 1250 UHPLC; MS system: Thermo LCQ Fleet; Column: Kinetex 2.6μ XB—C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Preparation of ethyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 30)

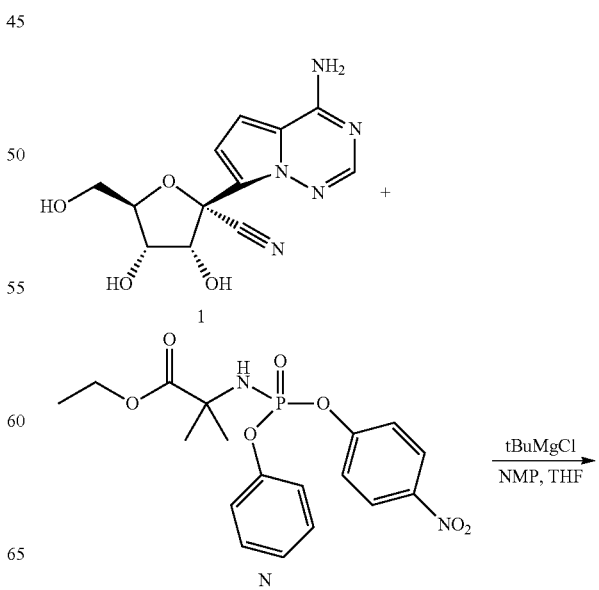

-continued

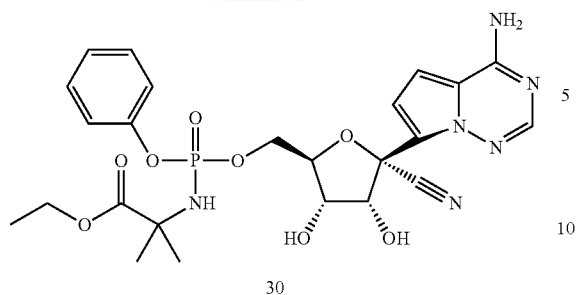

30

Take up compound 1 (66 mg, 0.23 mmol) in NMP (2.0 mL). Cool the mixture to about 0° C. and slowly add tBuMgCl (1.0M in THF, 0.34 mL, 0.34 mmol). Allow the reaction to stir at about 0° C. for about 30 min, then add a solution of compound N (139 mg, 0.34 mmol) dissolved in THF (1.0 mL). Remove the cold bath and place the reaction in about 50° C. preheated oil bath. After about 2 h, the reaction was cooled to room temperature and quenched with acetic acid and methanol. The crude was concentrated and purified by reverse phase HPLC without modifier to afford compound 30. $^1$H NMR (400 MHz, DMSO-$d_6$) δ 7.89 (m, 3H), 7.31 (q, J=8.1 Hz, 2H), 7.22-7.05 (m, 3H), 6.87 (d, J=4.5, 1H), 6.80 (d, J=4.5 Hz, 1H), 6.27 (d, J=11.7, 1H), 5.81 (d, J=9.7, 1H), 5.35 (d, J=5.6 Hz, 1H), 4.64 (dt, J=9.0, 5.6 Hz, 1H), 4.24 (m, 2H), 4.11 (m, 1H), 4.04-3.90 (m, 3H), 1.39-1.23 (m, 6H), 1.10 (t, J=7.1, 3H). $^{31}$P NMR (162 MHz, DMSO-$d_6$) δ 2.45, 2.41. LC/MS: $t_R$=1.03 min, MS m/z=561.03 [M+1]; LC system: Thermo Accela 1250 UHPLC; MS system: Thermo LCQ Fleet; Column: Kinetex 2.6µ XB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 34

Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (31)

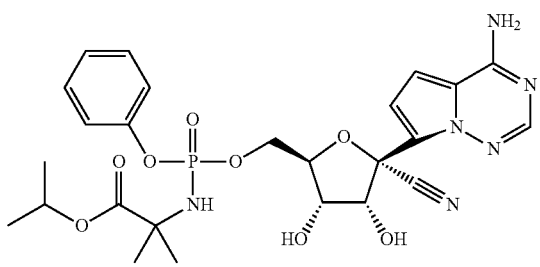 [SMILES: CC(C)OC(=O)C(C)(C)NP(=O)(OC[C@H]1O[C@@](C#N)(c2ccc3c(N)ncnn23)[C@H](O)[C@@H]1O)Oc1ccccc1]

The preparation of Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate is described below.

Preparation of Isopropyl 2-((tert-butoxycarbonyl)amino)-2-methylpropanoate

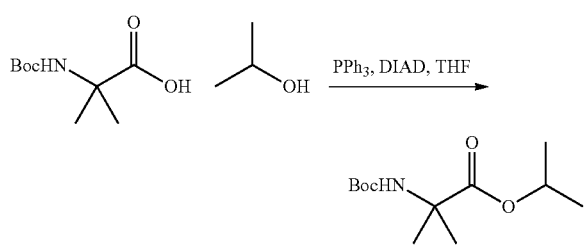

Take up triphenylphosphine (6.17 g, 25.00 mmol) in THF (30 mL). Next charge DIAD (4.92 mL, 25.00 mmol) and stir at room temperature for about 10 min. Dissolve 2-((tert-butoxycarbonyl)amino)-2-methylpropanoic acid (5.07 g, 25.00 mmol) dissolved in THF (20 mL) and add to the reaction mixture followed by the addition of isopropanol (1.91 mL, 25.00 mmol). Allow the reaction to stir at room temperature for about 1 h. The solvents were removed under reduced pressure and the crude was taken up in 1:1 Et$_2$O: Hexanes (120 mL). The solid triphenylphosphine oxide was filtered off and the solvent was removed under reduced pressure. The crude was taken up in minimal CH$_2$Cl$_2$ and purified by silica gel chromatography (0-50% EtOAc/Hex) to afford isopropyl 2-((tert-butoxycarbonyl)amino)-2-methylpropanoate. $^1$H NMR (400 MHz, Chloroform-d) δ 5.03 (p, J=6.2 Hz, 1H), 1.48 (s, 6H), 1.40 (d, J=6.2 Hz, 9H), 1.24 (d, J=6.3 Hz, 6H).

Preparation of Isopropyl 2-amino-2-methylpropanoate hydrochloride

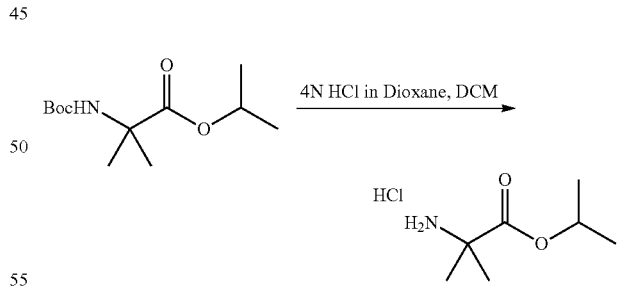

Take up isopropyl 2-((tert-butoxycarbonyl)amino)-2-methylpropanoate (4.09 g, 16.67 mmol) in CH$_2$Cl$_2$ (50 mL) and slowly add 4N HCl in dioxane (50 mmol) and stir at room temperature. At about 1 h, the reaction was determined to be complete by TLC. The solvents were removed under reduced pressure and the crude was coevaporated with Et$_2$O two times then placed under high vacuum to afford isopropyl 2-amino-2-methylpropanoate hydrochloride. $^1$H NMR (400 MHz, DMSO-$d_6$) δ 8.61 (s, 3H), 4.96 (p, J=6.2 Hz, 1H), 1.44 (s, 6H), 1.22 (d, J=6.2 Hz, 6H).

Preparation of Isopropyl2-methyl-2-(((4-nitrophenoxy)(phenoxy)phosphoryl)amino)propanoate (Compound O)

Preparation of Isopropyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)-2-methylpropanoate (Compound 31)

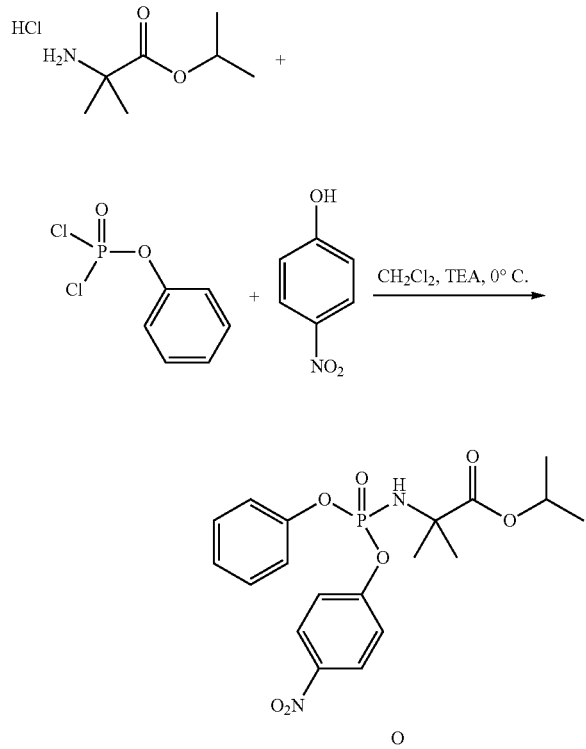

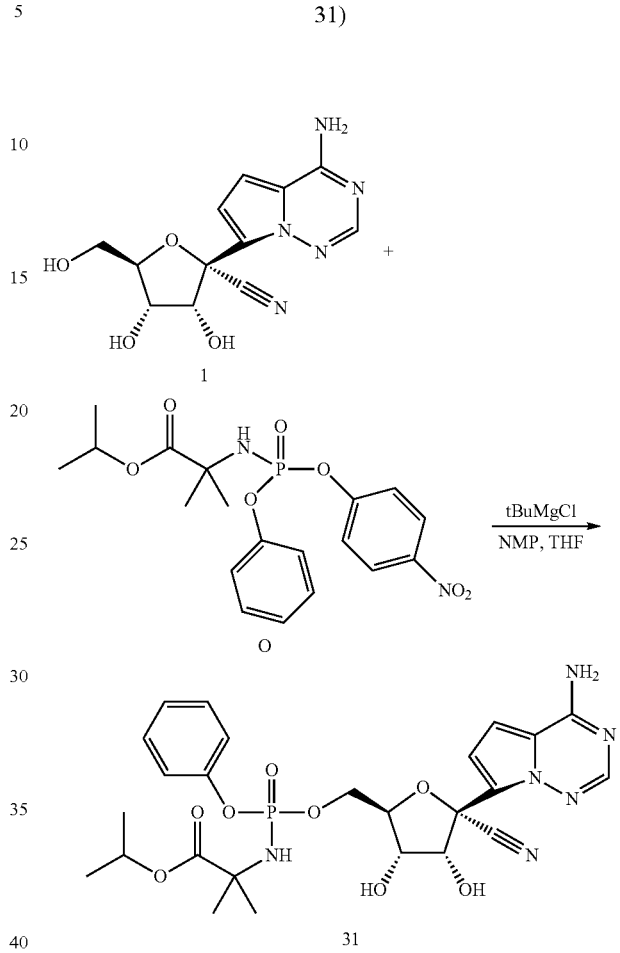

Take up phenyl dichlorophosphate (0.83 mL, 5.58 mmol) and isopropyl 2-amino-2-methylpropanoate hydrochloride (1.01 g, 5.58 mmol) in CH$_2$Cl$_2$ (50 mL). Cool the reaction mixture to 0° C. and slowly add TEA (1.61 mL, 11.45 mmol). Remove the cold bath and allow the reaction mixture to stir at room temperature. After about 2 h, the addition of the amino acid was determined to be complete by $^{31}$P NMR. Charge p-nitrophenol (0.74 g, 5.30 mmol) followed by the addition of TEA (0.81, 5.84 mmol). Allow the reaction to stir at room temperature. After about 2 h, the reaction was determined to be complete by LCMS. The reaction was diluted with Et$_2$O and the TEA.HCl salts were filtered off. The crude was concentrated and purified by silica gel chromatography (0-50% EtOAc/Hex) to afford compound O. $^1$H NMR (400 MHz, DMSO-d$_6$) δ 8.42-8.19 (m, 2H), 7.55-7.43 (m, 2H), 7.39 (dd, J=8.6, 7.2 Hz, 2H), 7.30-7.12 (m, 3H), 6.53 (d, J=10.1 Hz, 1H), 4.82 (hept, J=6.3 Hz, 1H), 1.38 (s, 6H), 1.09 (d, J=6.3, 6H). $^{31}$P NMR (162 MHz, DMSO-d$_6$) δ −2.84. LC/MS: t$_R$=1.73 min, MS m/z=422.92 [M+1]; LC system: Thermo Accela 1250 UHPLC; MS system: Thermo LCQ Fleet; Column: Kinetex 2.6 µXB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Take up compound 1 (66 mg, 0.23 mmol) in NMP (2.0 mL). Cool the mixture to about 0° C. and slowly add tBuMgCl (1.0M in THF, 0.57 mL, 0.57 mmol). Allow the reaction to stir at about 0° C. for about 30 min, then add a solution of compound 0 (143 mg, 0.34 mmol) dissolved in THF (1.0 mL). Remove the cold bath and place the reaction in an about 50° C. preheated oil bath. After about 2 h, the reaction was cooled to room temperature and was quenched with acetic acid and methanol. The crude was concentrated and purified by reverse phase HPLC without modifier to afford compound 31. $^1$H NMR (400 MHz, DMSO-d$_6$) δ 7.88 (m, 3H), 7.30 (td, J=8.5, 7.0 Hz, 2H), 7.20-7.04 (m, 3H), 6.87 (d, J=4.5, 1H), 6.80 (d, J=4.5 Hz, 1H), 6.27 (d, 6.1 Hz, 1H), 5.75 (t, J=9.1 Hz, 1H), 5.34 (d, J=5.7 Hz, 1H), 4.81 (p, J=6.3 Hz, 1H), 4.71-4.50 (m, 1H), 4.23 (m, 2H), 4.11 (m, 1H), 4.03-3.83 (m, 1H), 1.37-1.23 (m, 6H), 1.18-1.04 (m, 6H). $^{31}$P NMR (162 MHz, DMSO) δ 2.47, 2.43. LC/MS: t$_R$=1.08 min, MS m/z=575.06 [M+1]; LC system: Thermo Accela 1250 UHPLC; MS system: Thermo LCQ Fleet; Column: Kinetex 2.6 µXB-C18 100A, 50×3.00 mm; Solvents: Acetonitrile with 0.1% formic acid, Water with 0.1% formic acid; Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min.

Example 35

(S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl) amino)propanoate (32)

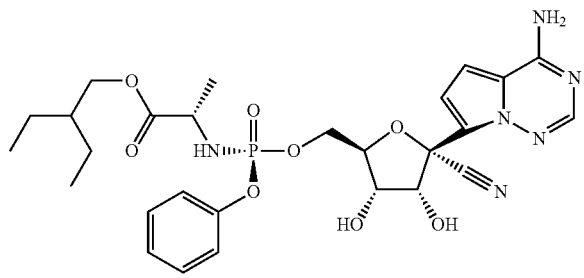 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

The preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate is described below.

Preparation of (3R,4R,5R)-3,4-bis(benzyloxy)-5-((benzyloxy)methyl)dihydrofuran-2(3H)-one

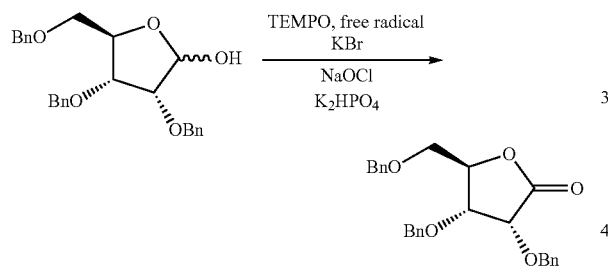

(3R,4R,5R)-3,4-bis(benzyloxy)-5-((benzyloxy)methyl) tetrahydrofuran-2-ol (15.0 g) was combined with MTBE (60.0 mL), KBr (424.5 mg), aqueous $K_2HPO_4$ solution (2.5M, 14.3 mL), and TEMPO (56 mg). This mixture was cooled to about 1° C. Aqueous bleach solution (7.9% wt.) was slowly charged in portions until complete consumption of starting material as indicated through a starch/iodide test. The layers were separated, and the aqueous layer was extracted with MTBE. The combined organic phase was dried over $MgSO_4$ and concentrated under reduced pressure to yield the product as a solid.

Preparation (4-amino-7-iodopyrrolo[2,1-f][1,2,4]triazine)

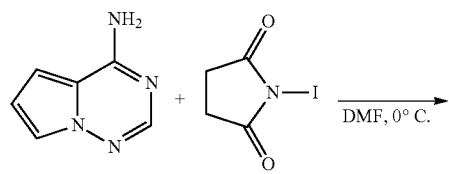

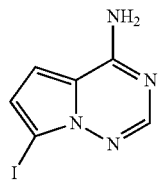

To a cold solution of 4-aminopyrrolo[2,1f][1,2,4]-triazine (10.03 g; 74.8 mmol) in N,N-dimethylformamide (70.27 g), N-iodosuccinimide (17.01 g; 75.6 mmol) was charged in portions, while keeping the contents at about 0° C. Upon reaction completion (about 3 h at about 0° C.), the reaction mixture was transferred into a 1 M sodium hydroxide aqueous solution (11 g NaOH and 276 mL water) while keeping the contents at about 20-30° C. The resulting slurry was agitated at about 22° C. for 1.5 h and then filtered. The solids are rinsed with water (50 mL) and dried at about 50° C. under vacuum to yield 4-amino-7-iodopyrrolo[2,1-f][1,2,4]triazine as a solid. $^1$H NMR (400 MHz, DMSO-d6) δ 7.90 (s, 1H), 7.78 (br s, 2H), 6.98 (d, J=4.4 Hz, 1H), 6.82 (d, J=4.4 Hz, 1H). $^{13}$C NMR (101 MHz, DMSO-d6) δ 155.7, 149.1, 118.8, 118.1, 104.4, 71.9. MS m/z=260.97 [M+H].

Preparation (3R,4R,5R)-2-(4-aminopyrrolo[2,1-f][1,2,4]triazin-7-yl)-3,4-bis(benzyloxy)-5-((benzyloxy)methyl)tetrahydrofuran-2-ol via (4-amino-7-iodopyrrolo[2,1-f][1,2,4]triazine)

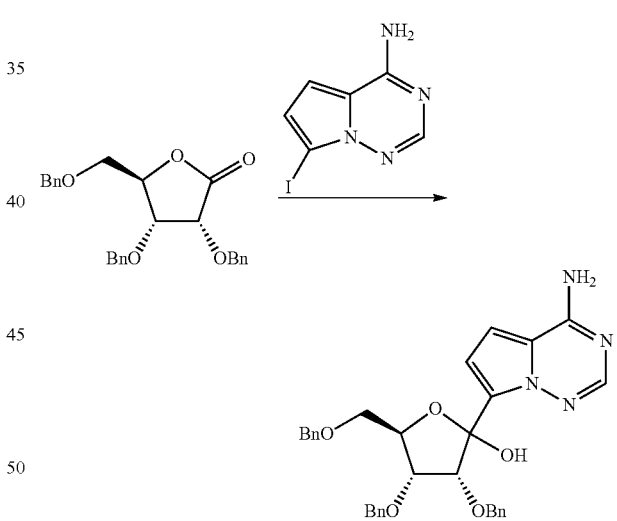

To a reactor under a nitrogen atmosphere was charged iodobase 2 (81 g) and THF (1.6 L). The resulting solution was cooled to about 5° C., and TMSCl (68 g) was charged. PhMgCl (345 mL, 1.8 M in THF) was then charged slowly while maintaining an internal temperature at about ≤5° C. The reaction mixture was stirred at about 0° C. for 30 min, and then cooled to about −15° C. iPrMgCl-LiCl (311 mL, 1.1 M in THF) was charged slowly while maintaining an internal temperature below about −12° C. After about 10 minutes of stirring at about −15° C., the reaction mixture was cooled to about −20° C., and a solution of lactone 1 (130 g) in THF (400 mL) was charged. The reaction mixture was then agitated at about −20° C. for about 1 h and quenched with AcOH (57 mL). The reaction mixture was warmed to about 0° C. and adjusted to pH 7-8 with aqueous NaHCO₃ (5 wt %, 1300 mL). The reaction mixture was then diluted with EtOAc (1300 mL), and the organic and aqueous layers were separated. The organic layer was washed with 1N HCl (1300 mL), aqueous NaHCO₃ (5 wt %, 1300 mL), and brine (1300 mL), and then dried over anhydrous Na₂SO₄ and concentrated to dryness. Purification by silica gel column chromatography using a gradient consisting of a mixture of MeOH and EtOAc afforded the product.

Preparation ((2S)-2-ethylbutyl 2-4(perfluorophenoxy)(phenoxy)phosphoryl)amino)propanoate) (mixture of Sp and Rp)

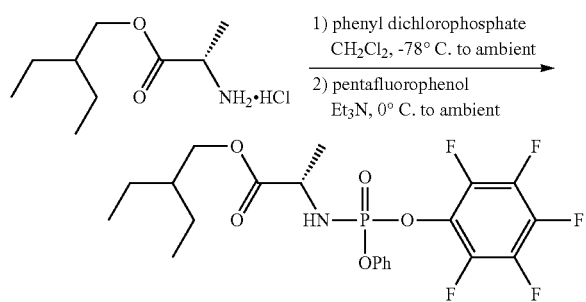

L-Alanine 2-ethylbutyl ester hydrochloride (5.0 g, 23.84 mmol) was combined with methylene chloride (40 mL), cooled to about −78° C., and phenyl dichlorophosphate (3.65 mL, 23.84 mmol) was added. Triethylamine (6.6 mL, 47.68 mmol) was added over about 60 min at about −78° C. and the resulting mixture was stirred at ambient temperature for 3 h. The reaction mixture was cooled to about 0° C. and pentafluorophenol (4.4 g, 23.84 mmol) was added. Triethylamine (3.3 mL, 23.84 mmol) was added over about 60 min. The mixture was stirred for about 3 h at ambient temperature and concentrated under reduced pressure. The residue was dissolved in EtOAc, washed with an aqueous sodium carbonate solution several times, and concentrated under reduced pressure. The residue was purified by silica gel column chromatography using a gradient of EtOAc and hexanes (0 to 30%). Product containing fractions were concentrated under reduced pressure to give (2S)-2-ethylbutyl 2-(((perfluorophenoxy)(phenoxy)phosphoryl)amino) propanoate as a solid. ¹H NMR (400 MHz, Chloroform-d) δ 7.41-7.32 (m, 4H), 7.30-7.17 (m, 6H), 4.24-4.16 (m, 1H), 4.13-4.03 (m, 4H), 4.01-3.89 (m, 1H), 1.59-1.42 (m, 8H), 1.40-1.31 (m, 8H), 0.88 (t, J=7.5 Hz, 12H). ³¹P NMR (162 MHz, Chloroform-d) δ −1.52. ¹⁹F NMR (377 MHz, Chloroform-d) δ −153.63, −153.93 (m), −160.05 (td, J=21.9, 3.6 Hz), −162.65 (qd, J=22.4, 20.5, 4.5 Hz). MS m/z=496 [M+H].

Preparation ((2S)-2-ethylbutyl 2-(((perfluorophenoxy)(phenoxy)phosphoryl)amino)propanoate)

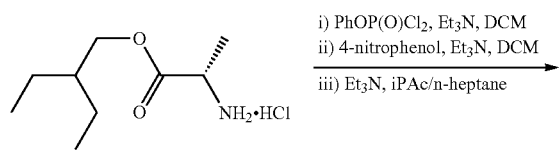

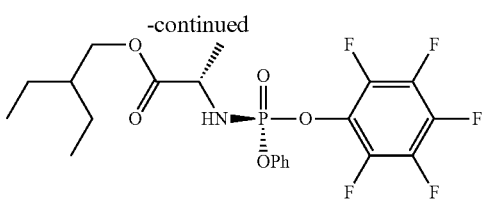

L-alanine-2-ethylbutylester hydrochloride (40.10 g, 0.191 mmol) was dissolved in dichloromethane (533 g) and the solution was cooled with stirring to about −15° C. under N₂(g). Phenyl dichlorophosphate (40.32 g, 0.191 mol) was added followed by slow addition of triethylamine (41.58 g, 0.411 mmol) and the reaction mixture was stirred at about −15° C. for about 1.5 h. Pentafluorophenol (35.14 g, 0.191 mol) was added, followed by triethylamine (19.23 g, 0.190 mol) and the reaction mixture was stirred for about 2 h. The reaction mixture was warmed to about 0° C. and 0.5 M HCl (279.19 g) was added. The mixture was warmed to about 22° C. and the organic layer was separated and washed with 5% KHCO₃ aqueous solution (281 g), then water (281 g). An aliquot of the organic layer (453.10 g of the 604.30 g solution) was concentrated to about 120 mL volume, isopropyl acetate (157 g) was added and the solution was concentrated to dryness. The residue was dissolved in isopropyl acetate (158 g). The resulting solution was concentrated to about 120 mL volume and the temperature was adjusted to about 45° C. n-Heptane (165 g) was added and the mixture was cooled to 22° C. over about 1 h. n-Heptane (167 g) was added and the mixture was cooled to about 0° C. Triethylamine (2.90 g, 0.0287 mol) was added and the mixture was stirred at 0° C. for about 17 h. The mixture was filtered, the solids were rinsed with n-heptane (145 g) and the solids were dried under vacuum at about 40° C. for about 15 h to provide 2-ethylbutyl ((S)-(penthafluorophenoxy)(phenoxy)phosphoryl)-L-alaninate.

Preparation 2-ethylbutyl ((S)-(4-nitrophenoxy)(phenoxy)phosphoryl)-L-alaninate

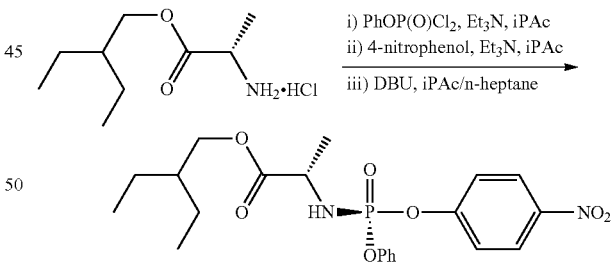

A slurry of L-alanine-2-ethylbutylester hydrochloride (20.08 g, 95.8 mmol) and isopropyl acetate (174 g) was cooled with stirring to about −20° C.). Phenyl dichlorophosphate (20.37 g, 96.5 mmol) was added, followed by slow addition of triethyl amine (20.97 g, 207.2 mmol) and the mixture was stirred at about −20° C. for about 1 h. 4-Nitrophenol (13.23 g, 95.1 mmol) was added, followed by slow addition of triethylamine (10.01 g, 98.8 mmol) and the reaction mixture was stirred for about 1.5 h. The reaction mixture was warmed to about 0° C. and 0.5 M HCl (140 g) was added. The organic layer was separated and washed with 5% Na₂CO₃ (2×100 g) and 10% NaCl (2×100 g). The organic layer was then concentrated to about 80 mL volume and isopropylacetate (4 g) was added, followed by n-heptane (110 g). Product seed crystals (0.100 g) were added followed by a second portion of n-heptane (110 g) and the mixture was cooled to about 0° C. 1,8-Diazabicycloundec-7-ene (1.49 g, 9.79 mmol) was added and the mixture was stirred at about 0° C. for about 21 h. The resultant solids were filtered and washed first with n-heptane (61 g) and then with H$_2$O (2×100 g). The solids were stirred with H$_2$O (200 g) for about 1.5 h, filtered, and rinsed with H$_2$O (3×100 g), then n-heptane (61 g). The obtained solids were dried under vacuum at about 40° C. for about 19 h to provide 2-ethylbutyl ((S)-(4-nitrophenoxy)(phenoxy)phosphoryl)-L-alaninate.

Preparation of Title Compound (mixture of Sp and Rp)

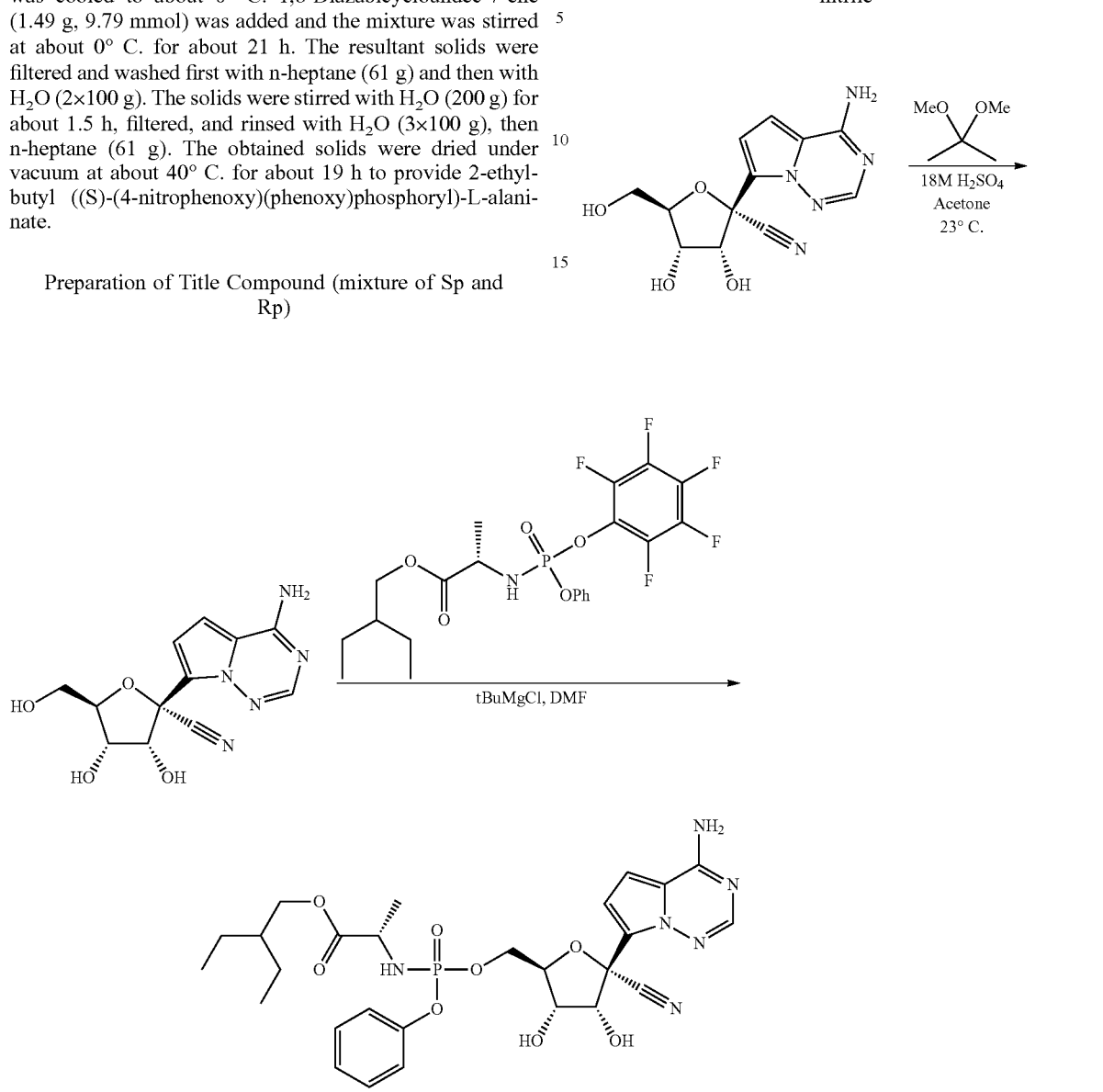

The nucleoside (29 mg, 0.1 mmol) and the phosphonamide (60 mg, 0.12 mmol) and N,N-dimethylformamide (2 mL) were combined at ambient temperature. Tert-Butyl magnesium chloride (1M in THF, 0.15 mL) was slowly added. After about 1 h, the reaction was diluted with ethyl acetate, washed with aqueous citric acid solution (5% wt.), aqueous saturated NaHCO$_3$ solution and saturated brine solution. The organic phase was dried over Na$_2$SO$_4$ and concentrated under reduced pressure. The residue was purified by silica gel column chromatography using a gradient of methanol and CH$_2$Cl$_2$ (0 to 5%). Product containing fractions were concentrated under reduced pressure to provide the product.

Preparation of (3 aR,4R,6R,6aR)-4-(4-aminopyrrolo [2,1-f][1,2,4]triazin-7-yl)-6-(hydroxymethyl)-2,2-dimethyltetrahydro furo[3,4-d][1,3]dioxole-4-carbonitrile -continued

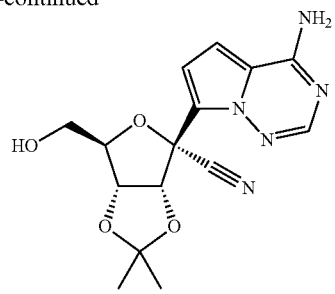

To a mixture of (2R,3R,4S,5R)-2-(4-aminopyrrolo[2,1-f] [1,2,4]triazin-7-yl)-3,4-dihydroxy-5-(hydroxymethyl)tetrahydrofuran-2-carbonitrile (5.8 g, 0.02 mol), 2,2-dimethoxypropane (11.59 mL, 0.09 mol) and acetone (145 mL) at ambient temperature was added sulfuric acid (18M, 1.44 mL). The mixture was warmed to about 45° C. After about 30 min, the mixture was cooled to ambient temperature and sodium bicarbonate (5.8 g) and water 5.8 mL) were added. After 15 min, the mixture was concentrated under reduced pressure. The residue was taken up in ethyl acetate (150 mL) and water (50 mL). The aqueous layer was extracted with ethyl acetate (2×50 mL). The combined organic phase was dried over sodium sulfate and concentrated under reduced pressure to give crude (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile. $^1$H NMR (400 MHz, CD$_3$OD) δ 7.84 (s, 1H), 6.93 (d, J=4.6 Hz, 1H), 6.89 (d, J=4.6 Hz, 1H), 5.40 (d, J=6.7 Hz, 1H), 5.00 (dd, J=6.7, 3.3 Hz, 1H), 4.48-4.40 (m, 1H), 3.81-3.72 (m, 2H), 1.71 (s, 3H), 1.40 (s, 3H). MS m/z=332.23 [M+1].

Preparation of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile TsOH salt

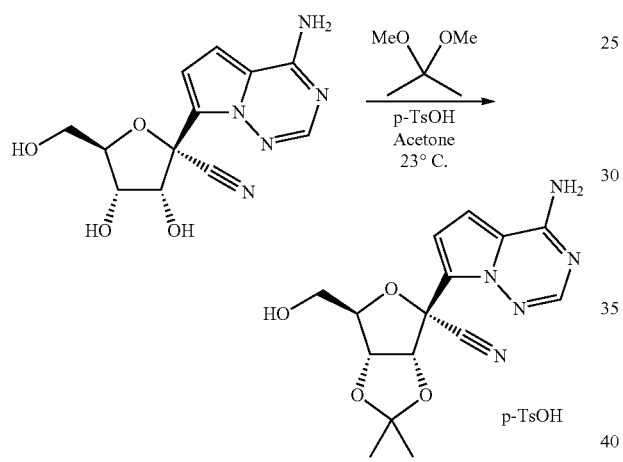

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (5.0 g, 17.2 mmol, 1.0 equiv.), 2,2-dimethoxypropane (10.5 mL, 86 mmol, 5.0 equiv.) and acetone (25 mL) at ambient temperature was added p-tolylsulfonic acid (3.59 g, 1.1 equiv.). The mixture was stirred at ambient temperature. After about 30 min, isopropyl acetate (25 mL) was added over about one hour. The resulting slurry was filtered and rinsed with 2:1 heptane:isopropyl acetate (25 ml). The product was dried under vacuum at about 40° C.

Preparation of (3aR,4R,6R,6aR)-4-(4-aminopyrrolo[2,1-f][1,2,4]triazin-7-yl)-6-(hydroxymethyl)-2,2-dimethyltetrahydrofurol[3,4-d][1,3]dioxole-4-carbonitrile

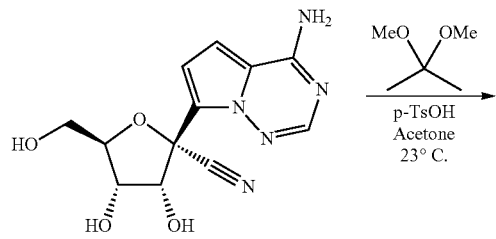

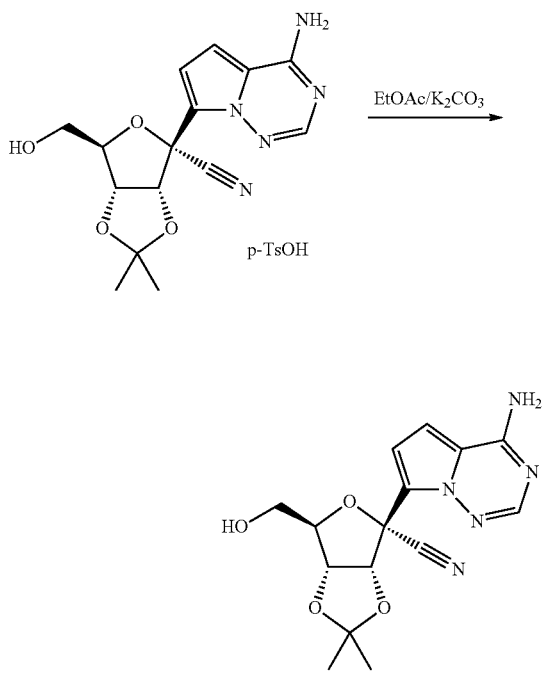

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (5 g, 17.2 mmol, 1.0 equiv.), 2,2-dimethoxypropane (10.5 mL, 86 mmol, 5.0 equiv.) and acetone (25 mL) at ambient temperature was added p-tolylsulfonic acid (3.59 g, 1.1 equiv.). The mixture was stirred at ambient temperature. After 30 min, isopropyl acetate (25 mL) was added over one hour. The resulting slurry was filtered and rinsed with 2:1 heptane:isopropyl acetate (25 ml). The product was dried under vacuum at 40° C. The isolated solid was added to a reactor and 5% K$_2$CO$_3$ solution (50 ml) and ethyl acetate (50 mL) were added. The layers were separated, and the aqueous layer washed with ethyl acetate (25 ml). The combined organic layers were washed with water (25 ml), then concentrated to ca.25 ml. The reactor was refilled with isopropyl acetate (25 ml) and concentrated to ca. 25 ml. The reactor was again refilled with isopropyl acetate (25 ml) and concentrated to 25 ml. The resulting solution was seeded, producing a thick slurry. To this was added heptane (25 ml) over one hour. The resulting slurry was filtered and rinsed with 2:1 heptane:isopropyl acetate (25 ml). The product was dried under vacuum at 40° C. ( ) (2R,3R,4S,5R)-2-(4-aminopyrrolo[2,14][1,2,4]triazin-7-yl)-3,4-dihydroxy-5-(hydroxymethyl)tetrahydrofuran-2-carbonitrile. $^1$H NMR (400 MHz, CD$_3$OD) δ 7.84 (s, 1H), 6.93 (d, J=4.6 Hz, 1H), 6.89 (d, J=4.6 Hz, 1H), 5.40 (d, J=6.7 Hz, 1H), 5.00 (dd, J=6.7, 3.3 Hz, 1H), 4.48-4.40 (m, 1H), 3.81-3.72 (m, 2H), 1.71 (s, 3H), 1.40 (s, 3H). MS m/z=332.23 [M+1].

Preparation of (2S)-2-ethylbutyl 2-(((((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate

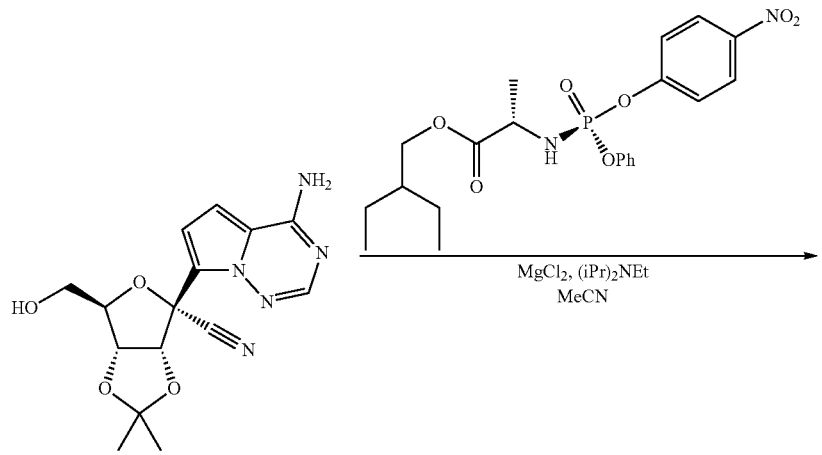

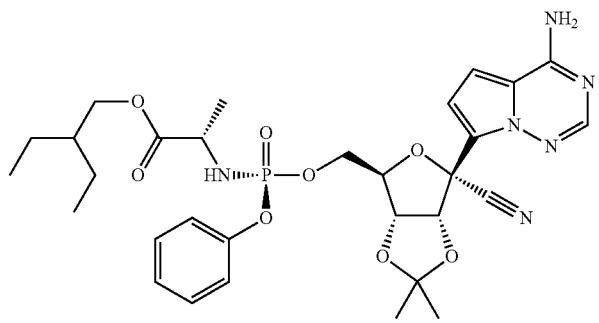

Acetonitrile (100 mL) was combined with (2S)-2-ethylbutyl 2((4-nitrophenoxy)(phenoxy)phosphoryl)-amino)propanoate (9.6 g, 21.31 mmol), the substrate alcohol (6.6 g, 0.02 mol),), magnesium chloride ((1.9 g, 19.91 mmol) at ambient temperature. The mixture was agitated for about 15 min and N,N-diisopropylethylamine (8.67 mL, 49.78 mmol) was added. After about 4 h, the reaction was diluted with ethyl acetate (100 mL), cooled to about 0° C. and combined with aqueous citric acid solution (5% wt., 100 mL). The organic phase was washed with aqueous citric acid solution (5% wt., 100 mL) and aqueous saturated ammonium chloride solution (40 mL), aqueous potassium carbonate solution (10% wt., 2×100 mL), and aqueous saturated brine solution (100 mL). The organic phase was dried with sodium sulfate and concentrated under reduced pressure to provide crude product. $^1$H NMR (400 MHz, CD$_3$OD) δ 7.86 (s, 1H), 7.31-7.22 (m, 2H), 7.17-7.09 (m, 3H), 6.93-6.84 (m, 2H), 5.34 (d, J=6.7 Hz, 1H), 4.98 (dd, J=6.6, 3.5 Hz, 1H), 4.59-4.50 (m, 1H), 4.36-4.22 (m, 2H), 4.02 (dd, J=10.9, 5.7 Hz, 1H), 3.91 (dd, J=10.9, 5.7 Hz, 1H), 3.83 (dq, J=9.7, 7.1 Hz, 1H), 1.70 (s, 3H), 1.50-1.41 (m, 1H), 1.39 (s, 3H), 1.36-1.21 (m, 7H), 0.86 (t, J=7.4 Hz, 6H). MS m/z=643.21 [M+1].

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (Compound 32)

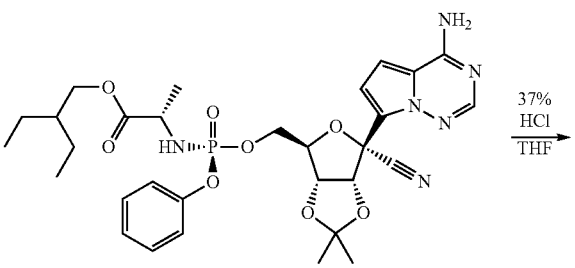

37% HCl / THF

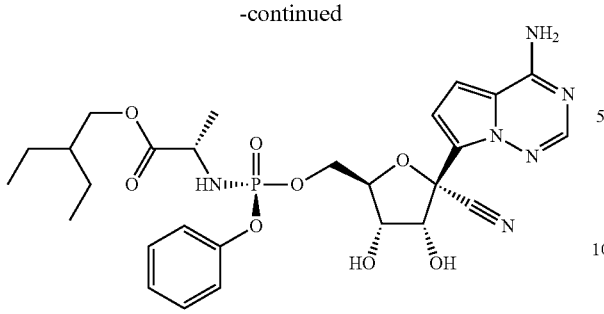

The crude acetonide (12.85 g) was combined with tetrahydrofuran (50 mL) and concentrated under reduced pressure. The residue was taken up in tetrahydrofuran (100 mL), cooled to about 0° C. and concentrated HCl (20 mL) was slowly added. The mixture was allowed to warm to ambient temperature. After consumption of the starting acetonide as indicated by HPLC analysis, water (100 mL) was added followed by aqueous saturated sodium bicarbonate solution (200 mL). The mixture was extracted with ethyl acetate (100 mL), the organic phase washed with aqueous saturated brine solution (50 mL), dried over sodium sulfated and concentrated under reduced pressure. The residue was purified by silica gel column chromatography using a gradient of methanol and ethyl acetate (0 to 20%). Product containing fractions were concentrated under reduced pressure to provide the product.

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (Compound 32)

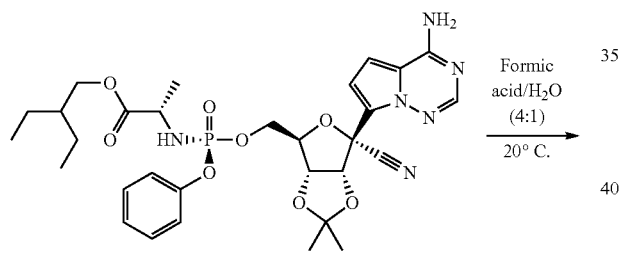

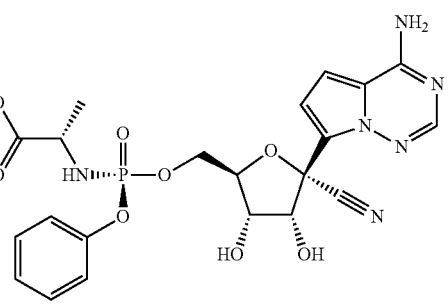

To a vial containing (S)-2-ethylbutyl 2-(((S)-(((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methoxy)(phenoxy)phosphoryl)amino)propanoate (30 mg, 0.05 mmol) was added an 80% aqueous formic acid solution (1.5 mL). After 18 h at about 20° C. complete conversion was confirmed by HPLC and LC-MS. MS (m/z)=603(M+1)$^+$.

Preparation of (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate (Compound 32) via Direct Coupling

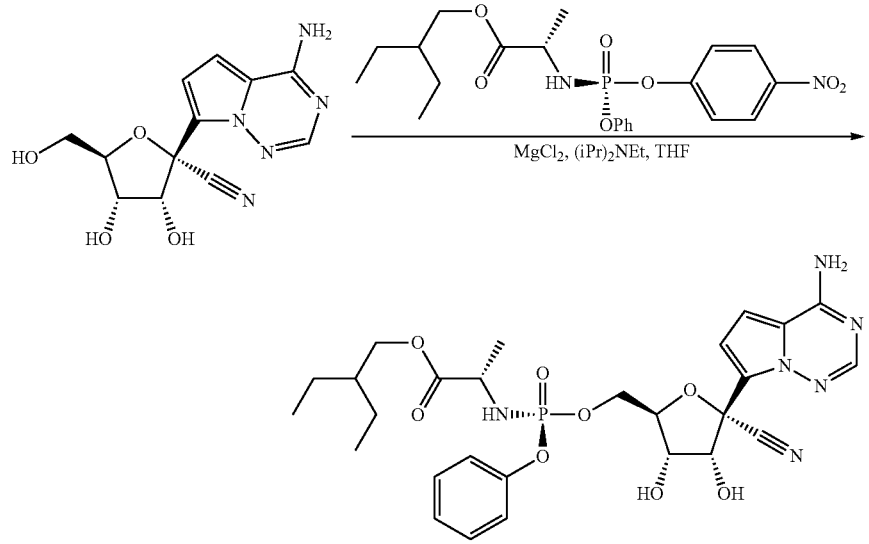

117

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (0.5 g, 2 mmol), (S)-2-ethylbutyl 2-(((S)-(4-nitrophenoxy)(phenoxy)phosphoryl)amino)propanoate (0.9 g, 2 mmol), and MgCl$_2$ (0.2 g, 2 mmol), was charged N,N-dimethylacetamide (10 mL). The resulting mixture was warmed to about 30° C. with constant stirring. N,N-Diisopropylethylamine (0.7 mL, 4 mmol) was then added slowly, and the reaction mixture was stirred for about 6 h. Water (10 mL) was charged H$_2$O, followed by 2-MeTHF (10 mL), and the organic and aqueous phases were separated. The aqueous layer was then back-extracted with 2-MeTHF (10 mL). The organic layers were combined, and washed with 10 wt % citric acid solution (10 mL), followed by 10 wt % K$_2$CO$_3$ solution (10 mL), and H$_2$O (10 mL). A small amount of brine was added to resolve emulsions in the water wash before the layers were separated. The organic layer was evaporated to dryness to afford 0.65 g of a foam. iPrOAc (2.6 mL) was added then added, and the mixture was warmed to about 40° C. to achieve dissolution. The solution was cooled to about 20° C., and the mixture was stirred for about 3 days. The solids were isolated by filtration, and the filter cake was washed with a small amount of iPrOAc. The solids were dried to afford (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate.

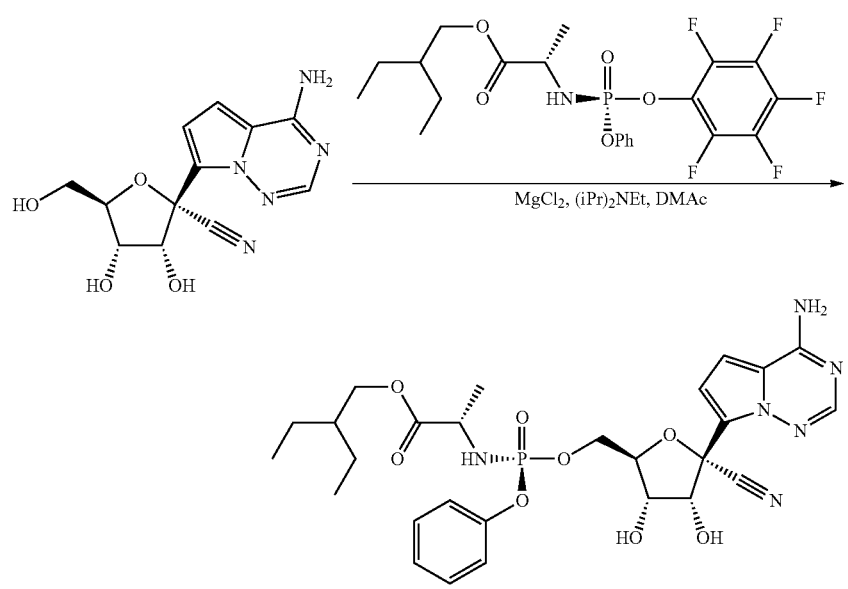

To a mixture of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (0.2 g, 0.7 mmol), (S)-2-ethylbutyl 2-(((S)-(perfluorophenoxy)(phenoxy)phosphoryl)amino)propanoate (0.3 g, 0.7 mmol), and MgCl$_2$ (0.1 g, 1 mmol), was charged N,N-dimethylacetamide (4 mL). The resulting mixture was warmed to about 30° C. with constant stirring. N,N-Diisopropylethylamine (0.3 mL, 2 mmol) was then added slowly, and the reaction mixture was stirred for 5 h. Conversion to the product was confirmed through UPLC analysis.

118

Preparation of (3R,4R,5R)-2-(4-aminopyrrolo[2,1-f][1,2,4]triazin-7-yl)-3,4-bis((tert-butyldimethylsilyl)oxy)-5-((((tert-butyldimethylsilyl)oxy)methyl)tetrahydrofuran-2-ol 1. TMSCl, PhMgCl, 0° C.
2. iPrMgCl, -15° C.
3. LaCl$_3$·2LiCl, -15° C.

THF, -20° C.

-continued

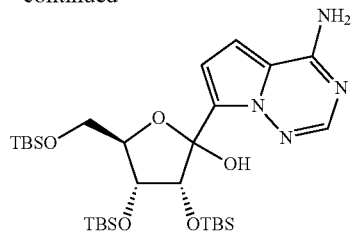

A solution of 7-iodopyrrolo[2,1-f][1,2,4]triazin-4-amine (13.9 g, 53.5 mmol) was prepared in THF (280 mL). The solution was cooled to about 0° C., and TMSCl (13.6 mL, 107 mmol) was added. The reaction mixture was stirred for about 20 min, and then PhMgCl (2 M in THF; 53.5 mL, 56.8 mmol) was added while maintaining an internal temperature below about 5° C. The reaction mixture was agitated at about 0° C. for about 30 min, and then cooled to about −20° C. iPrMgCl-LiCl (1.3 M in THF, 43.1 mL, 56 mmol) was then added while maintaining an internal temperature below about −15° C. The reaction mixture was agitated for about 30 min at about −20° C.

In a separate flask, a solution of (3R,4R,5R)-3,4-bis((tert-butyldimethylsilyl)oxy)-5-(((tert-butyldimethylsilyl)oxy)methyl)dihydrofuran-2(3H)-one (25.0 g, 50.9 mmol, 0.83 equiv) was prepared in LaCl$_3$-2LiCl (0.6 M in THF, 85 mL, 50.9 mmol). The solution was then transferred to the Grignard solution while maintaining an internal temperature below −20° C. The resulting reaction mixture was agitated at about −20° C. for about 4 h.

The reaction was quenched with 1 M HCl (140 mL), and the mixture warmed to ambient temperature. EtOAc (140 mL) was added, and the organic and aqueous phases were separated. The water layer was extracted with EtOAc (200 mL). The combined EtOAc layers were extracted sequentially with saturated aqueous NaHCO$_3$ (2×200 mL), water (200 mL), and brine (200 mL). The organic layer was concentrated, and then purified by silica gel chromatography (30% EtOAc/hexane) to afford (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol. $^1$H NMR (300 MHz, CDCl$_3$) δ 8.15-7.88 (m, 1H), 7.51 (d, J=4.8 Hz, 0.5H), 7.02-6.92 (m, 0.5H), 6.65-6.57 (m, 1H), 5.66-5.24 (m, 3H), 4.49-3.50 (m, 4H), 0.97-0.78 (26H), 0.65 (s, 1.5H), 0.19-0.00 (m, 15.5H), −0.22 (s, 1H), −0.55 (s, 1H). MS m/z=626 (M+H).

Preparation of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile

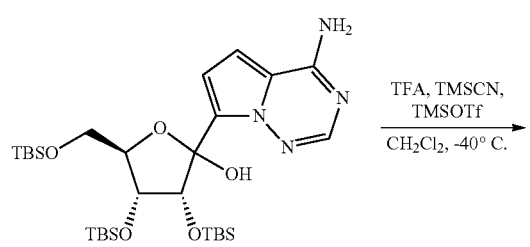

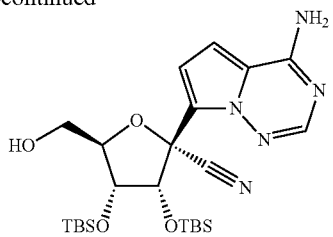

A solution of (3R,4R,5R)-2-(4-aminopyrrolo[2,14][1,2,4]triazin-7-yl)-3,4-bis((tert-butyldimethylsilyl)oxy)-5-(((tert-butyldimethylsilyl)oxy)methyl)tetrahydrofuran-2-ol (1.50 g, 2.40 mmol) in CH$_2$Cl$_2$ (15 mL) was cooled to about −40° C. Trifluoroacetic acid (0.555 mL, 7.20 mmol) was added keeping the temperature below −20° C. In a separate flask, trimethylsilyl trifluoromethanesulfonate (2.60 mL, 14.4 mmol) was added to 5 ml of CH$_2$Cl$_2$ (5 mL) at about 15° C., followed by trimethylsilyl cyanide (1.92 mL, 14.4 mmol), and the solution was cooled to about −30° C. The cooled solution was added to the solution of (3R,4R,5R)-2-(4-aminopyrrolo[2,1-f][1,2,4]triazin-7-yl)-3,4-bis((tert-butyldimethylsilyl)oxy)-5-(((tert-butyldimethylsilyl)oxy)methyl)tetrahydrofuran-2-ol while keeping the temperature below −25° C. The reaction mixture was stirred for 15 min at about −30° C. The reaction was quenched with triethylamine (3.34 mL, 24.0 mmol) and the mixture was warmed to about 0° C. Water (50 mL) was added while keeping the temperature below about 20° C. When the addition was complete the mixture was stirred for 15 min at room temperature. The layers were separated and the organic layer was washed sequentially with KOH (20 mL), water (20 mL), and brine (20 mL). The organic layer was dried over Na$_2$SO$_4$, concentrated, and then purified by silica gel chromatography (30% EtOAc/hexane) to afford the product as a 3.8:1 mixture of diastereomers). The mixture was purified further by prep-HPLC (ACN 0 to 95% in water) to afford the product as a single diastereomer. $^1$H NMR (400 MHz, DMSO-d6) δ 8.14-7.92 (m, 2H), 7.89 (s, 1H), 6.95 (d, J=4.8 Hz, 1H), 6.88 (d, J=4.4 Hz, 1H), 5.27 (d, J=4.6 Hz, 1H), 5.10 (dd, J=7.7, 4.6 Hz, 1H), 4.31 (dd, J=4.7, 1.4 Hz, 1H), 4.12 (ddd, J=5.9, 4.1, 1.4 Hz, 1H), 3.80-3.69 (m, 1H), 3.56 (td, J=7.8, 3.9 Hz, 1H), 0.93 (s, 9H), 0.75 (s, 9H), 0.11 (s, 3H), 0.09 (s, 3H), −0.15 (s, 3H), −0.62 (s, 3H). MS m/z=520 (M+H).

Preparation of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy) phosphoryl)amino)propanoate

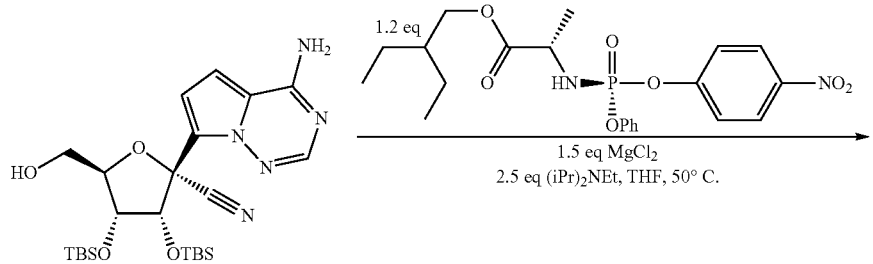

-continued

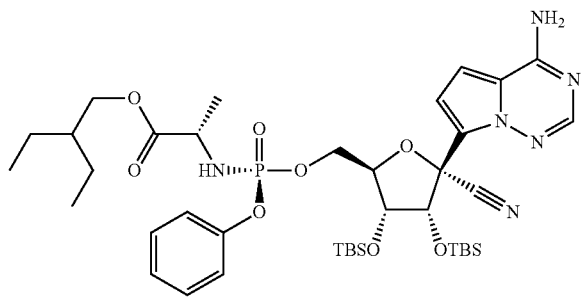

To a mixture of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile (16 mg, 0.03 mmol), (S)-2-ethylbutyl 2-(((S)-(4-nitrophenoxy)(phenoxy)phosphoryl)amino)propanoate (17 mg, 0.04 mmol), and MgCl$_2$ (4 mg, 0.05 mmol), was charged THF (0.3 mL). The resulting mixture was warmed to about 50° C. with constant stirring. N,N-Diisopropylethylamine (0.013 mL, 0.08 mmol) was then added, and the reaction mixture was stirred for 21 h. Conversion to the product was confirmed through UPLC and LC-MS analysis. MS m/z=831 (M+H).

solution of (S)-2-ethylbutyl 2-(((S)-(perfluorophenoxy)(phenoxy)phosphoryl)amino)propanoate (22 mg, 0.04 mmol) in THF (0.15 mL). The reaction mixture was warmed to 5° C., and stirred for 16 h. The reaction was quenched with MeOH, concentrated, and then purified by silica gel chromatography (EtOAc/hexanes) to afford the product. 1H NMR (400 MHz, CDCl$_3$) δ 7.97 (s, 1H), 7.38-7.29 (m, 2H), 7.25-7.21 (m, 2H), 7.21-7.13 (m, 1H), 7.11 (d, J=4.6 Hz, 1H), 6.65 (d, J=4.6 Hz, 1H), 5.88 (br s, 2H), 5.35 (d, J=4.4 Hz, 1H), 4.49-4.41 (m, 1H), 4.41-4.35 (m, 1H), 4.32-4.26 (m, 1H), 4.24 (dd, J=4.5, 1.7 Hz, 1H), 4.10-3.99 (m, 2H),

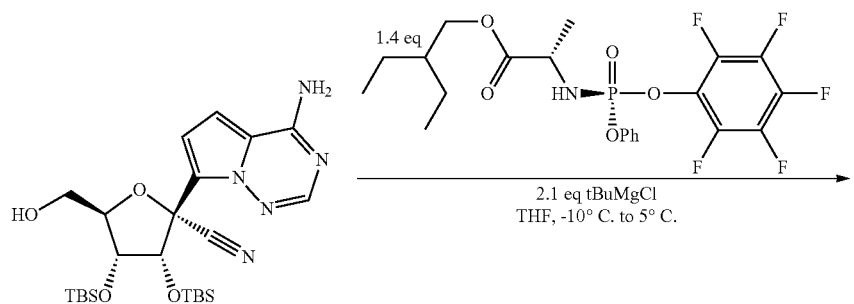

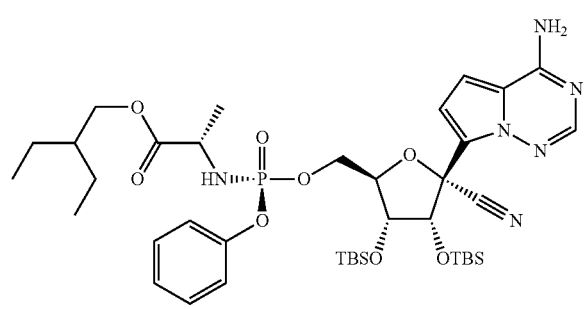

A solution of (2R,3R,4R,5R)-2-(4-aminopyrrolo[2,1-f][1,2,4]triazin-7-yl)-3,4-bis((tert-butyldimethylsilyl)oxy)-5-(hydroxymethyl)tetrahydrofuran-2-carbonitrile (16 mg, 0.03 mmol) in THF (0.3 mL) was cooled to −10° C. tBuMgCl was added dropwise (0.07 mL, 0.07 mmol), followed by a 3.96 (dd, J=10.9, 5.7 Hz, 1H), 3.80-3.72 (m, 1H), 1.48 (h, J=6.2 Hz, 1H), 1.39-1.28 (m, 7H), 0.96 (s, 9H), 0.85 (t, J=7.5 Hz, 6H), 0.80 (s, 9H), 0.08 (s, 3H), 0.07 (s, 3H), −0.13 (s, 3H), −0.56 (s, 3H). 31P NMR (162 MHz, CDCl3) δ 2.74 (s). MS m/z=831 (M+H).

Preparation of (S)-2-ethylbutyl 2-(((S)-(((2R,3S,4R, 5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino) propanoate

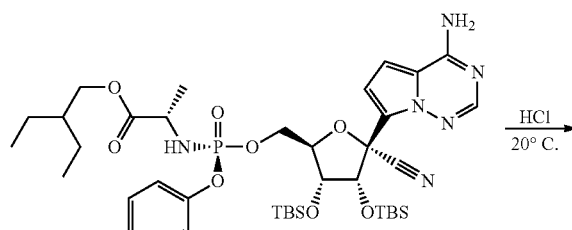

A crude solution of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy)phosphoryl)amino)propanoate was cooled to about 0° C. and conc HCl (0.05 mL, 0.62 mmol) was slowly added. The reaction mixture was stirred for about 72 hours at about 20° C. Conversion to the product was confirmed through UPLC and LC-MS analysis. MS m/z=603 (M+H).

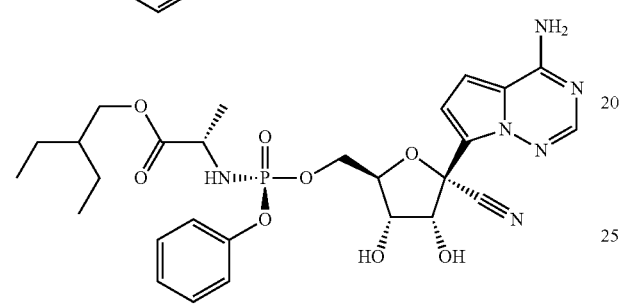

A solution of (S)-2-ethylbutyl 2-(((S)-(((2R,3R,4R,5R)-5-(4-aminopyrrolo[2,1-f][1,2,4]triazin-7-yl)-3,4-bis((tert-butyldimethylsilyl)oxy)-5-cyanotetrahydrofuran-2-yl)methoxy)(phenoxy)phosphoryl)amino)propanoate in a fluoride or acid can deprotect to a solution of (S)-2-ethylbutyl 2-(((S)-(((2R,3S,4R,5R)-5-(4-aminopyrrolo[2,1-f][1, 2,4]triazin-7-yl)-5-cyano-3,4-dihydroxytetrahydrofuran-2-yl)methoxy)(phenoxy)phosphoryl)amino)propanoate. Representative fluorides include, but are not limited to TBAF, KF, pyridinium hydrofluoride, triethylammonium hydrofluoride, hydrogen fluoride, hydrochloric acid, toluenesulfonic acid, or any other suitable fluoride source. Representative acids include, but are not limited to those found in Greene, T. W.; Wuts, P. G. M. *Protective Groups. In Organic Synthesis,* 4th Ed., John Wiley & Sons: New York, 2006.

Example 35 a. ((a2R,3S,4R,5R)-5-(4-aminopyrrolo[2,1-f][1,2,4] triazin-7-yl)-5-cyano-3,4-dihydroxytetrahydrofuran-2-yl)methoxy)oxidophosphoryl)alaninate (Compound 35)

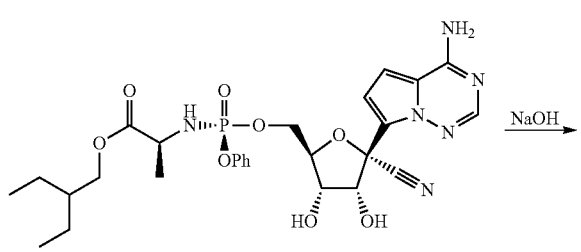

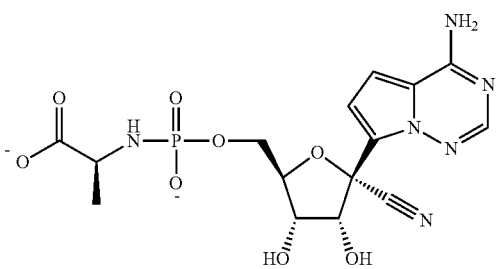

35

2-ethylbutyl ((S)-(((2R,3S,4R,5R)-5-(4-aminopyrrolo[2, 14][1,2,4]triazin-7-yl)-5-cyano-3,4-dihydroxytetrahydrofuran-2-yl)methoxy)(phenoxy)phosphoryl)-L-alaninate (130 mg, 0.216 mmol) was dissolved in mixture of acetonitrile (6 mL) and water (2 mL). Aqueous sodium hydroxide solution (2N, 0.5 mL) was added dropwise over 5 min at rt and the reaction mixture was stirred. After 2 h, the resulting mixture was concentrated under reduced pressure and the residue was purified by HPLC on a C18 column eluting with water to afford the desired product as the bis-sodium salt. $^1$H NMR (400 MHz, D$_2$O) δ 7.79 (s, 1H), 6.86 (d, J=4.7 Hz, 1H), 6.80 (d, J=4.7 Hz, 1H), 4.86 (d, J=5.4 Hz, 1H), 4.40-4.34 (m, 1H), 4.30 (dd, J=5.3, 3.0 Hz, 1H), 3.75 (qdd, J=11.6, 4.5, 3.1 Hz, 2H), 3.20 (dq, J=8.6, 7.1 Hz, 1H), 0.86 (d, J=7.0 Hz, 3H). $^{31}$P NMR (162 MHz, D$_2$O) δ 7.30. LCMS m/z 442.95 [M+H]. HPLC (2-98% MeCN—H$_2$O gradient with 0.1% TFA modifier over 8.5 min, 1.5 mL/min, Column: Phenomenex Kinetex C18, 2.6 um 100 Å, 4.6×100 mm) $t_R$=2.694 min.

B. Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

fully replicating reporter viruses expressing luciferase or green fluorescent protein (GFP) (Uebelhoer, L. S., 2014. AVR; Hoenen, T., 2013. AVR). All studies were conducted in biosafety level-4 containment (BSL-4) at the Centers for Disease Control and Prevention (CDC). Ebola virus antiviral assays were conducted in primary human microvascular endothelial cells immortalized with the telomerase catalytic protein (HMVEC-TERT) and in Huh-7 cells (Shao, R., 2004, BBRC). Nipah virus antiviral activity was measured in HMVEC-TERT and Hela cells.

Antiviral assays were conducted in 96well plates. Eight to ten concentrations of compound were diluted in 3-fold serial dilution increments in media and 100 uL/well of each dilution was transferred in triplicate onto plates containing preseeded cell monolayers. The plates were transferred to BSL-4 containment and the appropriate dilution of virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader by direct fluorescence for GFP reporter viruses or after subsequent addition of luciferase substrate for luciferase reporter viruses. For virus yield assays, media from infected cells was removed and a portion was used to

| Virus | Cell line | Plate format | Cell number | MOI (pfu/cell) | Incubation (Days) | Read out | Values |
|---|---|---|---|---|---|---|---|
| EBOV (Zaire) | Hela | 384 | 4000 | 0.5 | 2 | HCS | EC50 |
| EBOV (Zaire) | HFF-1 | | | 2 | | HCS | |
| EBOV-GFP | Huh-7 | 96 | 10000 | 0.1 | 4 | GFP | |
| EBOV-GFP | HMVEC-TERT | | | | | GFP | |
| EBOV-LUC | Huh-7 | | | | | LUC | |
| MARV-GFP | Huh-7 | | | | | GFP | |
| NiV | Hela | | | | | CPE | |
| NiV-GFP | HMVEC-TERT | | | | | GFP | |
| NiV-LUC | HMVEC-TERT | | | | | LUC | |

EBOV: Ebola virus strain Zaire
EBOV-GFP: Ebola reporter virus expressing green fluorescent protein
EBOV-LUC: Ebola reporter virus expressing luciferase
MARV-GFP: Marburg virus expressing green fluorescent protein
NiV: Nipah virus
NiV-GFP: Nipah reporter virus expressing green fluorescent protein
NiV-LUC: Nipah reporter virus expressing luciferase
HCS: High content imaging (immuno-staining of ebolavirus GP-protein)
GFP: Green fluorescent protein
LUC: Luciferase
CPE Cytopathic effects measured by cell titer glo (CTG) reagent
Hela: Hela epithelial cell (cervical carcinoma)
HFF-1: Human foreskin fibroblast
Huh-7: Hepatocyte
HVMEC-TERT: Human microvascular endothelial cells i mmortalized with the telomerase catalytic protein Example 36

Ebola Virus Antiviral Activity and Cytotoxicity Assays

Antiviral activity of Compound 1 and Compound 9 was measured against Ebola virus (EBOV), Marburg virus (MARV) (Table 2), and Nipah virus (NiV) (Table 3) using fully replicating reporter viruses expressing luciferase or green fluorescent protein (GFP) (Uebelhoer, L. S., 2014. AVR; Hoenen, T., 2013. AVR). Further antiviral activity of Compound 1 and Compound 9 was measured against Ebola virus (EBOV), Marburg virus (MARV) (Table 2-a), using quantify viral RNA by reverse transcription quantitative polymerase chain reaction (RT-qPCR). The remaining media was serially diluted and the amount of infectious virus was measured by using the diluted media to infect fresh cell monolayers to determine the tissue culture infectious dose that caused 50% cytopathic effects (TCID50) using Cell TiterGlo reagent (Promega, Madison, Wis.). For virus cytopathic effect (CPE) assays, viability of infected cells was measure using Cell TiterGlo reagent.

The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 37

EBOV-GFP HMVEC-TERT Cells

HMVEC-TERT cells were seeded in 96 well plates. Eight to ten concentrations of compound were diluted in 3-fold serial dilution increments in media and 100 uL/well of each dilution was transferred in triplicate onto 96 well plates containing preseeded HMVEC-TERT monolayers. The plates were transferred to BSL-4 containment and the appropriate dilution of EBOV-GFP virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader by direct fluorescence to measure GFP expression from the reporter virus. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 38

EBOV-GFP Huh-7 Cells

Huh-7 cells were seeded in 96 well plates. Eight to ten concentrations of compound were diluted in 3-fold serial dilution increments in media and 100 uL/well of each dilution was transferred in triplicate onto 96 well plates containing preseeded Huh-7 monolayers. The plates were transferred to BSL-4 containment and the appropriate dilution of EBOV-GFP virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader by direct fluorescence to measure GFP expression from the reporter virus. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 39

EBOV-Luc Huh-7 Cells

Huh-7 cells were seeded in 96well plates. Eight to ten concentrations of compound were diluted in 3-fold serial dilution increments in media and 100 uL/well of each dilution was transferred in triplicate onto plates containing preseeded cell monolayers. The plates were transferred to BSL-4 containment and the appropriate dilution of the EBOV-Luc virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader after subsequent addition of luciferase substrate. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 40

MARV-GFP Huh-7 Cells

Huh-7 cells were seeded in 96 well plates. Eight to ten concentrations of compound were diluted in 3-fold serial dilution increments in media and 100 uL/well of each dilution was transferred in triplicate onto 96 well plates containing preseeded Huh-7 monolayers. The plates were transferred to BSL-4 containment and the appropriate dilution of MARV-GFP virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader by direct fluorescence to measure GFP expression from the reporter virus. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 41

Ebola Huh-7 (RNA)

Huh-7 cells were seeded in 96 well plates. Eight to ten concentrations of compound were diluted in 3-fold serial dilution increments in media and 100 uL/well of each dilution was transferred in triplicate onto plates containing preseeded Huh-7 cell monolayers. The plates were transferred to BSL-4 containment and the appropriate dilution of EBOV virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, media from infected cells was removed and a portion was used to quantify viral RNA by reverse transcription quantitative polymerase chain reaction (RT-qPCR). The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 42

Ebola Huh-7 (Yield)

Huh-7 cells were seeded in 96 well plates. Eight to ten concentrations of compound were diluted in 3-fold serial dilution increments in media and 100 uL/well of each dilution was transferred in triplicate onto plates containing preseeded Huh-7 cell monolayers. The plates were transferred to BSL-4 containment and the appropriate dilution of EBOV virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, media from infected cells was removed and diluted in 10-fold serial dilutions. The amount of infectious virus was measured by using the diluted media to infect fresh cell monolayers to determine the tissue culture infectious dose that caused 50% cytopathic effects (TCID50) using Cell TiterGlo reagent (Promega, Madison, Wis.). The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 43

Ebola HeLa Cells

The antiviral activity of selected compounds was measured against ebolavirus (EBOV) strain Zaire conducted in biosafety level-4 containment (BSL-4) at the US Army Medical Research Institute for Infections Disease (USAMRIID). Hela cells were seeded in 384 well plates at 5000 cells/well. The antiviral activity of each compound was measured in quadruplicate. Eight to ten concentrations of compound were added directly to the cell cultures using the HP300 digital dispenser in 3-fold serial dilution increments 2 h prior to infection. The plates were transferred to BSL-4 containment and the appropriate dilution of virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 2 days in a tissue culture incubator. After the incubation, the cells were fixed in formalin solution and virus replication was measured by quantifying Ebola glycoprotein levels after immunostaining and high content imaging using the Perkin Elmer Opera confocal microscopy instrument. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 44

Ebola Macrophage Cultures

The antiviral activity of selected compounds was measured against ebolavirus (EBOV) strain Zaire conducted in biosafety level-4 containment (BSL-4) at the US Army Medical Research Institute for Infections Disease (USAMRIID). Macrophage cultures were isolated from fresh human PBMCs and differentiated in the presence of 5 ng/ml GM-CSF and 50 uM B-mercaptoethanol. The media was changed every 2 days and cells that adhered to the tissue culture plate after 7 days were removed with 0.5M EDTA in 1×PBS, concentrated by centrifugation at 200×g for 10 minutes and plated in 384 well assay plates at 40,000 cells/well. The antiviral activity of each compound was measured in quadruplicate. Eight to ten concentrations of compound were added directly to the cell cultures using the HP300 digital dispenser in 3-fold serial dilution increments 2 h prior to infection. The plates were transferred to BSL-4 containment and the appropriate dilution of virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 2 days in a tissue culture incubator. After the incubation, the cells were fixed in formalin solution and virus replication was measured by quantifying Ebola glycoprotein levels after immunostaining and high content imaging using the Perkin Elmer Opera confocal microscopy instrument. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 45

Nipah-GFP HMVEC-TERT Cells

HMVEC-TERT cells were seeded in 96 well plates. Eight to ten concentrations of compound were diluted in 3-fold serial dilution increments in media and 100 uL/well of each dilution was transferred in triplicate onto 96 well plates containing preseeded HMVEC-TERT monolayers. The plates were transferred to BSL-4 containment and the appropriate dilution of NiV-GFP virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader by direct fluorescence to measure GFP expression from the reporter virus. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 46

NiV-Luc HMVEC-TERT

HMVEC-TERT cells were seeded in 96well plates. Eight to ten concentrations of compound were diluted in 3-fold serial dilution increments in media and 100 uL/well of each dilution was transferred in triplicate onto plates containing preseeded cell monolayers. The plates were transferred to BSL-4 containment and the appropriate dilution of the Niv-Luc virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, virus replication was measured in an Envision plate reader after subsequent addition of luciferase substrate. The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 47

NiV Hela (Yield)

Hela cells were seeded in 96 well plates. Eight to ten concentrations of compound were diluted in 3-fold serial dilution increments in media and 100 uL/well of each dilution was transferred in triplicate onto plates containing preseeded Hela cell monolayers. The plates were transferred to BSL-4 containment and the appropriate dilution of Niv virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 4 days in a tissue culture incubator. After the incubation, media from infected cells was removed and diluted in 10-fold serial dilutions. The amount of infectious virus was measured by using the diluted media to infect fresh cell monolayers to determine the tissue culture infectious dose that caused 50% cytopathic effects (TCID50) using Cell TiterGlo reagent (Promega, Madison, Wis.). The percentage inhibition was calculated for each tested concentration relative to the 0% and 100% inhibition controls and the $EC_{50}$ value for each compound was determined by non-linear regression as the effective concentration of compound that inhibited virus replication by 50%.

Example 48

Niv Hela (RNA)

Huh-7 cells were seeded in 96 well plates. Eight to ten concentrations of compound were diluted in 3-fold serial dilution increments in media and 100 uL/well of each dilution was transferred in triplicate onto plates containing preseeded Hela cell monolayers. The plates were transferred to BSL-4 containment and the appropriate dilution of Niv virus stock, previously determined by titration and prepared in cell culture media, was added to test plates containing cells and serially diluted compounds. Each plate included three wells of infected untreated cells and three wells of uninfected cells that served as 0% and 100% virus inhibition control, respectively. Following the infection, test plates were incubated for 3 to 4 days in a tissue culture incubator. After the incubation, media from infected cells was removed and a portion was used to quantify viral RNA by reverse transcription quantitative polymerase chain reaction (RT-qPCR). The percentage inhibition was calculated for each tested concentration relative to the 0% and 100% inhibition controls and the $EC_{50}$ value for each compound was determined by non-linear regression as the effective concentration of compound that inhibited virus replication by 50%.

TABLE 2

Ebola and Marburg virus antiviral assays

| | $EC_{50}$ (nM) Assay | | | | | | | |
|---|---|---|---|---|---|---|---|---|
| | Reporter Virus | | | Virus | RNA | Yield | Antigen expression (high content imaging) | |
| | EBOV-GFP | | EVOV-Luc | MARV-GFP | | | Ebola | |
| | Cell line | | | | | | | |
| | HMVEC-TERT | Huh-7 | Huh-7 | Huh-7 | Huh-7 | | Hela | Macrophage |
| Compound 1 | 771 | 1492 | 3126 | 1726 | ND | ND | >20,000 | >20,000 |
| Compound 9 | 121 | 90 | ND | ND | 1 | 1029 | 290 | 501 |
| (R)-Diastereomer of Compound 9 | 62 | 70 | ND | ND | ND | ND | | |
| (S)-Diastereomer of Compound 9 (Compound 32) | 40 | 81 | ND | ND | ND | ND | | |
| Compound 10 | | | | | | | | |
| Compound 15 | 630 | 271 | ND | ND | ND | ND | | |
| Compound 21 | 905 | | | | | | | 270 |
| Compound 22 | ND | ND | ND | ND | ND | ND | | |
| Compound 23 | 458 | | | | | | 1650 | 243, 350 |
| Compound 24 | | | | | | | | |
| Compound 25 | | | | | | | | |
| Compound 26 | 283 | | | | | | 970, 1180 | 1180 |
| Compound 27 | 82 | | | | | | 182 | |
| Compound 28 | 102 | | | | | | 975 | 120 |

TABLE 2-continued

Ebola and Marburg virus antiviral assays

| | EC$_{50}$ (nM) Assay | | | | | | |
|---|---|---|---|---|---|---|---|
| | Reporter Virus | | Virus | RNA | Yield | Antigen expression (high content imaging) | |
| | EBOV-GFP | EVOV-Luc | MARV-GFP | | | Ebola | |
| | | | Cell line | | | | |
| | HMVEC-TERT | Huh-7 | Huh-7 | Huh-7 | Huh-7 | Hela | Macrophage |
| Compound 29 | | | | | | | |
| Compound 30 | | | | | | | |
| Compound 31 | 11061 | | | | | >20,000 | 1230 |

EBOV-GFP: Ebola virus expressing the GFP reporter gene
EBOV-Luc: Ebola virus expressing he luciferase reporter gene
MARV-GFP: Marburg virus expressing the GFP reporter gene
Ebola: Ebolavirus strain 2014

TABLE 2-a

Ebola and Marburg virus antiviral assays

| | EC$_{50}$ (nM) Assay | | | | | | |
|---|---|---|---|---|---|---|---|
| | Reporter Virus | | Virus | RNA | Yield | Antigen expression (high content imaging) | |
| | EBOV-GFP | EVOV-Luc | MARV-GFP | | | Ebola | |
| | | | Cell line | | | | |
| | HMVEC-TERT | Huh-7 | Huh-7 | Huh-7 | Huh-7 | Hela | Macrophage |
| Compound 1 | 771 | 1492 | 3126 | 1726 | ND | ND | >20,000 | >20,000 |
| Compound 9 | 121 | 90 | ND | ND | 1 | 1029 | 290, 270 | 501, 70 |
| (R)-Diastereomer of Compound 9 | 62 | 70 | ND | ND | ND | ND | 210 | 112 |
| (S)-Diastereomer of Compound 9 (Compound 32) | 40 | 81 | ND | ND | ND | ND | 100 | 87 |
| Compound 10 | | | | | | | 3200 | |
| Compound 15 | 630 | 271 | ND | ND | ND | ND | 520 | 501 |
| Compound 21 | 905, 473 | | | | | | | 270 |
| Compound 22 | ND | ND | ND | ND | ND | ND | 11570 | |
| Compound 23 | 458 | | | | | | 1650, 1845 | 243, 350, 297 |
| Compound 24 | | | | | | | 785 | |
| Compound 25 | | | | | | | 6720 | |
| Compound 26 | 283 | | | | | | 970, 1180, 1103 | 1180, 1290 |
| Compound 27 | 82 | | | | | | 182 | |
| Compound 28 | 102 | | | | | | 975, 682 | 120 |
| Compound 29 | | | | | | | 275 | |
| Compound 30 | 11061 | | | | | | >20000 | 1230 |
| Compound 31 | | | | | | | >20,000, >10000 | |

EBOV-GFP: Ebola virus expressing the GFP reporter gene
EBOV-Luc: Ebola virus expressing he luciferase reporter gene
MARV-GFP: Marburg virus expressing the GFP reporter gene
Ebola: Ebolavirus strain 2014

TABLE 3

| Nipah and Hendra virus antiviral assays | | | | |
|---|---|---|---|---|
| Assay | EC$_{50}$ (nM) Reporter Virus | | CPE | Yield |
| Virus | NiV GFP | NiV Luc | NiV | |
| Cell line | HMVEC-TERT | | Hela | |
| Compound 1 | 13420 | 3500 | 1484 | 1000 |
| Compound 9 | 60 | 30 | ND | ND |

NiV GFP: Nipah virus expressing the GFP reporter gene
NiV-Luc: Nipah virus expressing the luciferase reporter gene
NiV: Nipah virus All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A compound:

or a pharmaceutically acceptable salt thereof.

2. A pharmaceutical composition comprising a therapeutically effective amount of a compound of the formula:

or a pharmaceutically acceptable salt thereof.

3. A pharmaceutical composition comprising the compound of claim 1, or a pharmaceutically acceptable salt thereof, and one or more pharmaceutically acceptable carriers and optionally other therapeutic agents.

4. The pharmaceutical composition according to claim 3 wherein the other therapeutic agents is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S, 3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and mixtures thereof.

5. The pharmaceutical composition according to claim 4 wherein the other therapeutic agents is ZMapp.

6. A method of treating a Filoviridae infection in a human in need thereof comprising administering a therapeutically effective amount of a compound or a pharmaceutically acceptable salt thereof of claim 1 or a pharmaceutical composition of any one of claims 3 to 5.

7. The method of claim 6 wherein the Filoviridae infection is an ebolavirus infection.

8. The method of claim 6 wherein the Filoviridae infection is a Marburg virus infection.

* * * * *